(12) United States Patent
Ashwell et al.

(10) Patent No.: US 7,812,051 B2
(45) Date of Patent: Oct. 12, 2010

(54) PHARMACEUTICAL COMPOSITIONS OF β-LAPACHONE AND β-LAPACHONE ANALOGS WITH IMPROVED TUMOR TARGETING POTENTIAL

(75) Inventors: Mark A. Ashwell, Carlisle, MA (US); Chiang J. Li, West Roxbury, MA (US); Manish Tandon, Framingham, MA (US); Yanbin Liu, Acton, MA (US); Jean-Marc LaPierre, Pelham, NH (US); Zhiwei Jiang, Stow, MA (US)

(73) Assignee: ArQule, Inc., Woburn, MA (US)

( * ) Notice: Subject to any disclaimer, the term of this patent is extended or adjusted under 35 U.S.C. 154(b) by 685 days.

(21) Appl. No.: 11/201,097

(22) Filed: Aug. 11, 2005

(65) Prior Publication Data

US 2006/0034796 A1 Feb. 16, 2006

Related U.S. Application Data

(60) Provisional application No. 60/600,373, filed on Aug. 11, 2004.

(51) Int. Cl.
*A61K 31/352* (2006.01)
*C07D 311/92* (2006.01)

(52) U.S. Cl. .................. 514/454; 514/455; 424/423; 549/389

(58) Field of Classification Search .................. 424/423; 514/454; 549/389
See application file for complete search history.

(56) References Cited

U.S. PATENT DOCUMENTS

| | | | |
|---|---|---|---|
| 4,963,565 A | 10/1990 | Gangadharam | |
| 5,120,843 A | 6/1992 | McCall et al. | |
| 5,210,239 A | 5/1993 | Abe et al. | |
| 5,385,942 A | 1/1995 | Abe et al. | |
| 5,534,536 A | 7/1996 | Ohuchida et al. | 514/397 |
| 5,674,900 A | 10/1997 | Ubillas et al. | |
| 5,763,625 A | 6/1998 | Boothman et al. | |
| 5,780,514 A | 7/1998 | Gutteridge et al. | |
| 5,783,598 A | 7/1998 | Boyd et al. | |
| 5,824,700 A | 10/1998 | Frydman et al. | |
| 5,840,900 A | 11/1998 | Greenwald et al. | |
| 5,880,131 A | 3/1999 | Greenwald et al. | |
| 5,969,163 A | 10/1999 | Frydman et al. | |
| 5,977,163 A | 11/1999 | Li et al. | |
| 6,245,807 B1 | 6/2001 | Pardee et al. | |
| 6,376,470 B1 | 4/2002 | Greenwald et al. | |
| 6,458,974 B1 | 10/2002 | Jiang et al. | |
| 6,608,076 B1 | 8/2003 | Greenwald et al. | |
| 6,962,944 B2 | 11/2005 | Jiang et al. | |
| 7,074,824 B2 | 7/2006 | Jiang et al. | |
| 2002/0169135 A1 | 11/2002 | Pardee et al. | |
| 2003/0091639 A1 | 5/2003 | Jiang et al. | |
| 2004/0071775 A1 | 4/2004 | Jiang et al. | |
| 2004/0087610 A1 | 5/2004 | Pardee et al. | |
| 2004/0266857 A1 | 12/2004 | Jiang et al. | |
| 2006/0034796 A1 | 2/2006 | Ashwell et al. | |
| 2006/0035963 A1 | 2/2006 | Ashwell et al. | |

FOREIGN PATENT DOCUMENTS

| | | |
|---|---|---|
| EP | 0040506 | 11/1981 |
| JP | 05124969 | 5/1993 |
| WO | WO 94/04145 | 3/1994 |
| WO | WO 95/05200 | 2/1995 |
| WO | WO-9633988 A1 | 10/1996 |
| WO | WO 97/41093 | * 11/1997 |
| WO | WO 00/61142 | 10/2000 |
| WO | WO 00/66175 | 11/2000 |
| WO | WO 00/66175 A3 | 11/2000 |
| WO | WO 01/26693 A2 | 4/2001 |
| WO | WO 01/70275 A2 | 9/2001 |
| WO | WO 02/058694 A2 | 8/2002 |
| WO | WO 03/011224 A2 | 2/2003 |
| WO | WO 03/011224 A3 | 2/2003 |
| WO | WO 03/053473 A2 | 7/2003 |
| WO | WO 03/090710 A1 | 11/2003 |
| WO | WO-2004006849 A2 | 1/2004 |
| WO | WO 2004/045557 A2 | 6/2004 |
| WO | WO 2004/045557 A3 | 6/2004 |
| WO | WO 2005/082356 A2 | 9/2005 |

(Continued)

OTHER PUBLICATIONS

Villar-Garea et al., Procaine is a DNA-demethylating Agent with Growth-inhibitory Effects in Human Cancer Cells, Cancer Research, 2003, 63, p. 4984-4989.*

(Continued)

*Primary Examiner*—Frederick Krass
*Assistant Examiner*—Darryl C Sutton
(74) *Attorney, Agent, or Firm*—Mintz Levin Cohn Ferris Glovsky and Popeo, P.C.; Ivor R. Elrifi, Esq.; Matthew Pavao, Esq.

(57) ABSTRACT

The present invention relates to polymer-modified quinone-containing and carbonyl-containing therapeutic agents, including polymer-modified β-lapachone compounds, and methods of treating cancer by administering the polymer-modified therapeutic agents to a subject. Polymer-modification of therapeutic agents, such as β-lapachone compounds, provides effective transport of polymer-modified therapeutic agents to tumor cells or tumor tissues by exploiting the EPR effect in tumor tissues.

2 Claims, 9 Drawing Sheets

FOREIGN PATENT DOCUMENTS

| WO | WO 2005/082357 A1 | 9/2005 |
| --- | --- | --- |
| WO | WO 2006/020719 A2 | 2/2006 |
| WO | WO 2006/020722 A2 | 2/2006 |
| WO | WO-2006128120 A2 | 11/2006 |
| WO | WO 03/090710 | * 11/2009 |

OTHER PUBLICATIONS

Pawliszyn, J., Sampling and Sample Preparation for Field and Laboratory, 2002, Elsevier, p. 618.*

Di Chenna et al., "Preparation and Cytotoxicity Toward Cancer Cells of Mono(arylimino) Derivatives of β-Lapachone", *Journal of Medicinal Chemistry*, 44:2486-2489 (2001).

International Search Report for International Application No. PCT/US2005/028445.

Kumi-Diaka, et al., "Potential Mechanism of Phytochemical-induced Apoptosis in Human Prostrate Adenocarcinoma Cells: Therapeutic Synergy in Genistein and β-Lapochone Combination Treatment", *Cancer Cell Treatment International*, 4:5 (2004).

Ohya et al., "Synthesis and Cytotoxic Activity of Conjugates of Monomethoxy-Poly(ethylene glycol) End-capped with Doxorubicin via Ester, Amide, or Schiff's Base Bond", *Journal of Bioactive and Compatible Polymers*, 10:51-66 (1995).

Partial International Search Results for PCT Application No. PCT/US2005/028438.

Powis et al., "Molecular Pharmacology and Antitumor Activity of Palmarumycin-based Inhibitors of Thioredoxin Reductase", *Molecular Cancer Therapeutics*, 5(3):630-636 (2006).

Ashraf et al., "Comparative Effects of Intraduodenal Psyllium and Senna on Canine Small Bowel Motility", *Aliment Pharmacol. Ther*, 8:329-336 (1994).

Bailey et al., "Involvement of DT-Diaphorase (EC 1.6.99.2) in the DNA Cross-Linking and Sequence Selectivity of the Bioreductive Anti-Tumour Agent EO9", *British Journal of Cancer*, 76(12):1596-1603 (1997).

Begleiter et al., "Induction of DT-Diaphorase in Cancer Chemoprevention and Chemotherapy", *Oncol. Res.*, 9:371-382 (1997).

Boorstein et al., "Coordinate Inhibition of DNA Synthesis and Thymidylate Synthase Activity Following DNA Damage and Repair", *Biochem. Biophys. Commun.*, 117(1):30-36 (1983).

Boothman et al., "Potentiation of Halogenated Pyrimidine Radiosensitizers in Human Carcinoma Cells by β-Lapachone (3,4-Dihydro-2,2-dimethyl-2$H$-naphtho[1,2-$b$]pyran-5,6-dione), a Novel DNA Repair Inhibitor", *Cancer Res.*, 47:5361-5366 (1987).

Choe et al., "Anticancer Drug Delivery Systems: $N^4$-Acyl Poly(Ethyleneglycol) Prodrugs of Ara-C. I. Efficacy in Solid Tumors", *Journal of Controlled Release*, 79:41-53 (2002).

Choe et al., "Anticancer Drug Delivery Systems: Multi-Loaded $N^4$-Acyl Poly(Ethylene Glycol) Prodrugs of Ara-C. II. Efficacy in Ascites and Solid Tumors", *Journal of Controlled Release*, 79:55-70 (2002).

Chuang et al., "Oxidative Free Radical Reaction of 2-Phenylthio-1,4-Naphthoquinones Initiated by Manganese(III) Acetate", *Heterocycles*, 43(10):2215-2221 (1996).

Chung et al., "Acceleration of the Alcohol Oxidation Rate in Rats with Aloin, a Quinone Derivative of Aloe", *Biochem. Pharmacol.*, 52:1461-1468 (1996).

Clarys et al., "Efficacy of Topical Treatment of Pigmentation Skin Disorders with Plant Hydroquinone Glucosides as Assessed by Quantitative Color Analysis", *J. Dermatol.*, 25:412-414 (1998).

Conover et al., "Camptothecin Delivery Systems: Enhanced Efficacy and Tumor Accumulation of Camptothecin Following its Conjugation to Polyethylene Glycol via a Glycine Linker", *Cancer Chemother Pharmacol.*, 42(4):407-414 (1998).

Conover et al., "Camptothecin Delivery Systems: the Utility of Amino Acid Spacers for the Conjugation of Camptothecin with Polyethylene Glycol to Create Prodrugs", *Anticancer Drug Design*, 14(6):499-506 (1999).

Cortelli et al., "Clinical and Brain Bioenergetics Improvement with Idebenone in a Patient with Leber's Hereditary Optic Neuropathy: a Clinical and $^{31}$P-MRS Study", *J. Neurol. Sci.*, 148:25-31 (1997).

Driscoll et al. "Structure-Antitumor Activity Relationships Among Quinone Derivatives", *Cancer Chemot. Reports Part 2*, 4(2):1-362 (1974).

Duncan, Ruth, "The Dawning Era of Polymer Therapeutics", *Nature Reviews*, 2:347-360 (2003).

Etrych et al., "New HPMA Copolymers Containing Doxorubicin Bound Via pH-Sensitive Linkage: Synthesis and Preliminary In Vitro and In Vivo Biological Properties", *Journal of Controlled Release*, 73:89-102 (2001).

Etrych et al., "Synthesis of HPMA Copolymers Containing Doxorubicin Bound via a Hydrazone Linkage. Effect of Spacer on Drug Release and In Vitro Cytotoxicity", *Macromolecular Bioscience*, 2(1):43-52 (2002).

Frydman et al., "Induction of DNA Topoisomerase II-Mediated DNA Cleavage by β-Lapachone and Related Naphthoquinones", *Cancer Res.*, 57:620-627 (1997).

Gantchev et al., "Inhibition of the Topoisomerase II-DNA Cleavable Complex by the *ortho*-Quinone Derivative of the Antitumor Drug Etoposide (VP-16)", *Biochem. Biophys. Res. Comm.*, 237(1):24-27 (1997).

Gehrhardt et al., "Soluble Polymers in Organic Chemistry 5. Preparation of Carboxyl- and Amino-Terminal Polyethylene Glycol of Low Molecular Weight", *Polymer Bull.*, 18:487-493 (1987).

Gonçalves et al., "Evaluation of the Toxicity of 3-Allyl-β-Lapachone Against *Trypa-Nosoma Cruzi* Bloodstream Forms", *Mol. Biochem. Parasitology*, 1:167-176 (1980).

Greenwald et al., "Drug Delivery System. 2. Camptothecin 20-*O*-Poly (Ethylene Glycol) Ester Transport Forms", *J. Med. Chem.*, 39(10):1938-1940 (1996).

Greenwald et al., "Drug Delivery Systems: Water Soluble Taxol 2'-Poly(ethylene glycol) Ester Prodrugs-Design and In Vivo Effectiveness", *J. Med. Chem.*, 39(2):424-431 (1996).

Greenwald et al., "Camptothecin-20-PEG Ester Transport Forms: the Effect of Spacer Groups on Antitumor Activity", *Bioorganic & Medicinal Chemistry*, 6:551-562 (1998).

Greenwald et al., "Drug Delivery Systems Employing 1,4- or 1,6-Elimination: Poly(Ethylene Glycol) Prodrugs of Amine-Containing Compounds", *J. Med. Chem.*, 42(18):3657-3667 (1999).

Greenwald et al., "Drug Delivery Systems Based on Trimethyl Lock Lactonization: Poly(Ethylene Glycol) Prodrugs of Amino-Containing Compounds", *J. Med. Chem.*, 43(3):475-487 (2000).

Greenwald et al., "Controlled Release of Proteins from Their Poly(ethylene Glycol) Conjugates: Drug Delivery Systems Employing 1,6-Elimination", *Bioconj. Chem.*, 14(2):395-403 (2003).

Greish et al., "Copoly(styrene-maleic acid)- Pirarubicin Micelles: High Tumor-Targeting Efficiency with Little Toxicity", *Bioconjugate Chem.*, 16(1):230-236 (2005).

Huang et al., "β-Lapachone Induces Cell Cycle Arrest and Apoptosis in Human Colon Cancer Cells" *Mol. Med.*, 5:711-720 (1999).

Krapcho et al., "Heterosubstituted Anthracene-9,10-dione Analogues. The Synthesis and Antitumor Evaluation of 5,8-Bis[(aminoalkyl)amino]Naphtho[2,3-$b$]Thiophene-4,9-diones", *J. Med. Chem.*, 33(9):2651-2655 (1990).

Krishnan et al., "Novel Mechanisms of DNA Topoisomerase II Inhibition by Pyranonaphthoquinone Derivatives-Eleutherin, α Lapachone, and β Lapachone", *Biochem Pharm*, 60:1367-1379 (2000).

Kurokawa, "The Reaction of Cadalene and Eudaline with Sulfur", *Bulletin of The Chemical Society of Japan*, 43(5):1454-1459 (1970).

Lai, et al., "β-Lapachone Induced Cell Death in Human Hepatoma (HepA2) Cells", *Histol Histopathol.*, 13:89-97 (1998).

Li et al., "Induction of Apoptosis by β-Lapachone in Human Prostate Cancer Cells", *Cancer Res.*, 55:3712-3715 (1995).

Li et al., "β-Lapachone, a Novel DNA Topoisomerase I Inhibitor with a Mode of Action Different from Camptothecin", *J. Biol. Chem.*, 268(30):22463-22468 (1993).

Li et al., "Potent Inhibition of Tumor Survival in vivo by β-Lapachone Plus Taxol: Combining Drugs Imposes Different Artificial Checkpoints", *Proc. Natl. Acad. Sci. USA*, 96(23):13369-13374 (1999).

Li, "Release of Mitochondrial Cytochrome C in Both Apoptosis and Necrosis Induced by β-Lapachone in Human Carcinoma Cells", *Mol. Med.*, 5:232-239 (1999).

Li et al., "Potent Induction of Apoptosis by β-Lapachone in Human Multiple Myeloma Cell Lines and Patient Cells", *Mol. Med.*, 6(12):1008-1015 (2000).

Mahadik et al., "Oxidative Injury and Potential Use of Antioxidants in Schizophrenia", *Prostaglandins Leukot. Essent. Fatty Acids*, 55(1 &2):45-54 (1996).

Matsumura et al., "A New Concept for Macromolecular Therapeutics in Cancer Chemotherapy: Mechanism of Tumoritropic Accumulation of Proteins and the Antitumor Agent Smancs", *Cancer Res.*, 46(12 Pt 1):6387-6392 (1986).

Mordente et al., "Antioxidant Properties of 2,3-Dimethoxy-5-methyl-6-(10-hydroxydecyl)-1,4-Benzoquinone (Idebenone)", *Chem. Res. Toxicol,.* 11:54-63 (1998).

Muller-Lissner, "Adverse Effects of Laxatives: Fact and Fiction", *Pharmacol.*, 47 (Suppl. 1):138-145 (1993).

Nanji et al., "Association Between Endothelial Cell Proliferation and Pathologic Changes in Experimental Alcoholic Liver Disease", *Toxicol. Appl. Pharmacol.*, 140:101-107 (1996).

Ochoa et al., *Proceedings of Am. Soc. of Clinical Oncology*, 19:(Abstract 770), (2000).

Pink et al., "NAD(P)H:Quinone Oxidoreductase Activity is the Principal Determinant of β-Lapachone Cytotoxicity", *J. Biol Chem.*, 275(8):5416-5424 (2000).

Planchon et al., "β-Lapachone-Mediated Apoptosis in Human Promyelocytic Leukemia (HL-60) and Human Prostate Cancer Cells: A p53-Independent Response", *Cancer Res.*, 55(17):3706-3711 (1995).

Portela et al., "Redox Cycling of β-Lapachone and Related o-Naphthoquinones in the Presence of Dihydrolipoamide and Oxygen", *Biochem Pharm*, 51:275-283 (1996).

Rao et al., "A Comparative Study of the Redox-Cycling of a Quinone (Rifamycin S) and a Quinonimine (Rifabutin) Antibiotic by Rat Liver Microsomes", *Free Radic. Biol. Med.*, 22(3):439-446 (1997).

Reinicke et al., "Development of β-Lapachone Prodrugs for Therapy Against Human Cancer Cells with Elevated NAD(P)H:Quinone Oxidoreductase 1 Levels", *Clin. Cancer. Res.*, 11(8):3055-64 (2005).

Rowinsky et al., "Phase I and Pharmacologic Study of High Doses of the Topoisomerase I Inhibitor Topotecan with Granulocyte Colony-Stimulating Factor in Patients with Solid Tumors", *Journal of Clinical Oncology*, 14(4):1224-1235 (1996).

Sartomer Website printed on May 24, 2006 (4 pages).

Schaffner-Sabba et al., "β-Lapachone: Synthesis of Derivatives and Activities in Tumor Models", *J. Med. Chem.*, 27:990-994 (1984).

Singh et al., "Capsaicin (8-Methyl-N-Vanillyl-6-Nonenamide) Is a Potent Inhibitor of Nuclear Transcription Factor-κB Activation by Diverse Agents", *The Journal of Immunol.*, 157:4412-4420 (1996).

Suggs et al., "Facile Hydrolysis and Formation of Amide Bonds by N-Hydroxyethylation of α-Amino Acids", *Tetrahedron Letters.*, 38(13):2227-2230 (1997).

Suginome et al., "One-Step Synthesis of 2,3-Dihydronaphtho[2,3-b]thiophene-4,9-diones by a New Regioselective [3+2] Photoaddition of Photogenerated 2-Mercapto-1,4-naphthoquinone with Alkenes", *J. Chem. Soc. Chem. Commun.*, 9:807-809 (1993).

Tapia et al., "Synthesis of 3,4-Dihydro-4-hydroxy-9-methoxy-2H-naphtho[2,3-b]thiopyranoquinone", *Tetrahedron Letters*, 38(1):153-154 (1997).

Tapia et al., "Synthesis of 2H-Naphtho[2,3-*b*]Thiopyranoquinones and Density Functional Study for the Diels-Alder Reaction of a Benzothiopyranoquinone", *Heterocycles*, 53(3):585-598 (2000).

Tonholo et al., "Electrochemical Properties of Biologically Active Heterocyclic Naphthoquinones", *J. Braz. Chem. Soc.*, 9(2):163-169 (1998).

Veronese et al., "Preparation, Physico-Chemical and Pharmacokinetic Characterization of Monomethoxypoly(Ethylene Glycol)-Derivatized Superoxide Dismutase", *Journal of Controlled Release*, 10:145-154 (1989).

Weller et al., "Topoisomerase-I Inhibitors for Human Malignant Glioma:Differential Modulation of p53, p21, bax and bcl-2 Expression and of CD95-Mediated Apoptosis by Camptothecin and β-Lapachone", *Int. J. Cancer*, 73:707-714 (1997).

Wuerzberger et al., "Induction of Apoptosis in MCF-7:WS8 Breast Cancer Cells by β-Lapachone", *Cancer Res.*, 58:1876-1885 (1998).

Yamaoka et al., "Distribution and Tissue Uptake of Poly(Ethylene Glycol) with Different Molecular Weights After Intravenous Administration to Mice", *Journal of Pharmaceutical Sciences*, 83(4):601-606 (1994).

Bradshaw et al., "Preclinical evaluation of amino acid prodrugs of novel antitumor 2-(4-amino-3-methylphenyl)benzothiazoles", *Mol. Cancer Ther.*, 1(4):239-246 (2002).

Hooker, S.C., "The constitution of lapachol and its derivatives. Part V. The structure of Paterno's 'Isolapachone'", *J. Am. Chem. Soc.*, 58(7):1190-1197 (1936).

* cited by examiner

PHARMACEUTICAL COMPOSITIONS OF β-LAPACHONE AND β-LAPACHONE ANALOGS WITH IMPROVED TUMOR TARGETING POTENTIAL

RELATED APPLICATION

The present application claims the benefit of U.S. Provisional Application No. 60/600,373, filed Aug. 11, 2004. The present application also claims priority to PCT Application No. PCT/US2005/028445, filed Aug. 11, 2005, which PCT application is herein incorporated by reference in its entirety.

FIELD OF THE INVENTION

The present invention relates to improved compositions and methods for delivering therapeutic agents bearing carbonyl or quinone functionalities and improved methods for treating cancer. One embodiment of the invention relates to improved β-lapachone compositions and methods of using such compositions for the treatment of cancer.

BACKGROUND OF THE INVENTION

The delivery of therapeutic agents to specific tissues or sites within a body presents a variety of challenges, particularly where local delivery of a high dose of an insoluble therapeutic agent to a specific tissue is desired. While it has been recognized that modification of therapeutic agents by conjugation to soluble polymers may aid in their localized delivery, this technique has required the presence, or introduction, of functionalities into the therapeutic agent to accommodate a linkage to the polymer vehicle. Where it is necessary to introduce functionality into a therapeutic agent by chemical modification to accommodate a linkage, characteristics of the therapeutic agent such as potency, half-life, and metabolism may be altered. There is continuing need for polymer conjugates that can solublize and deliver therapeutic agents to specific tissues without requiring functionalization of the therapeutic agent to accommodate linkage to the polymer vehicle. Moreover, targeting of therapeutics to specific tissues via linkage to a polymeric delivery vehicle may result in diminished side effects.

There are insufficient means for conjugation of therapeutic agents via quinone and carbonyl functionalities to polymeric vehicles that can release the therapeutic agent unaltered under in vivo conditions. It may be advantageous to solubilize and deliver such carbonyl-containing and quinone-containing therapeutic agents to specific tissues by conjugation with suitable polymer vehicles. Therapeutic agents containing carbonyl or quinone functionalities that might advantageously be delivered by suitable polymeric vehicles include lobeline, acebutolol, methyprylon, haloperidol, molindone, naloxone, oxycodone, methadone, ketanserin, tolmetin, ketoprofen, nabumetone, canrenone, canrenonate, mebendazole, oxolinic acid, tetracycline, chlortetracycline, oxytetracycline, demeclocycline, doxycycline, minocycline, daunorubicin, doxorubicin, mitoxantrone, plicamycin, mitomycin, indan-1,3-dione, anisindione, testosterone (and related C-17 esters, e.g., propionate, enanthate, cypionate), dihydrotesterone, cyproterone acetate, estrone, progesterone, medroxyprogesterone acetate, hydroxyprogesterone caproate, norethindrone, norethynodrel, megestrol acetate, norgestrel, mifepristone, methandrostenolone, oxandrolone, testolactone, cyproterone acetate, prednisone, prednisolone, betamethasone, dexamethasone, other 3-, 17-, or 20-ketosteroids (e.g., dehydroepiandorsterone, androstenedione, cortisol, cortisone, aldosterone, etc.), and particularly β-lapachone compounds.

β-lapachone (3,4-dihydro-2,2-dimethyl-2H-naphtho[1,2-b]pyran-5,6-dione), a quinone, is derived from lapachol (a naphthoquinone) which can be isolated from the lapacho tree (*Tabebuia avellanedae*), a member of the catalpa family (Bignoniaceae). Lapachol and β-lapachone (with numbering) have the following chemical structures:

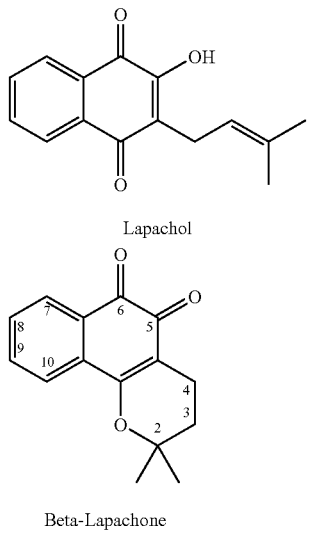

Lapachol

Beta-Lapachone

β-lapachone, as well as its intermediates, derivatives and analogs thereof, are described in Li, C. J. et al., (1993) *J. Biol. Chem.*, 268(30): 22463-22468.

As a single agent, β-lapachone has demonstrated significant antineoplastic activity against human cancer cell lines at concentrations typically in the range of 1-10 μM ($IC_{50}$). Cytotoxicity has been demonstrated in transformed cell lines derived from: patients with promyelocytic leukemia (Planchon et al., (1996) *Cancer Res.*, 55: 3706-3711), prostate (Li, C. J., et al., (1995) *Cancer Res.*, 55: 3712-3715), malignant glioma (Weller, M. et al., (1997) *Int. J. Cancer*, 73: 707-714), hepatoma (Lai, C. C., et al., (1998) *Histol Histopathol*, 13: 89-97), colon (Huang, L., et al., (1999) *Mol Med*, 5: 711-720), breast (Wuertzberger, S. M., et al., (1998) *Cancer Res.*, 58: 1876), ovarian (Li, C. J. et al., (1999) *Proc. Natl. Acad. Sci. USA*, 96(23): 13369-13374), pancreatic (Li, Y., et al., (2000) *Mol Med*, 6: 1008-1015; Li, Y., (1999) *Mol Med*, 5: 232-239), and multiple myeloma cell lines, including drug-resistant lines (Li, Y., (2000) *Mol Med*, 6: 1008-1015). No cytotoxic effects were observed on normal fresh or proliferating human peripheral blood mononuclear cells (PBMC) (Li, Y., (2000) *Mol Med*, 6: 1008-1015).

β-lapachone appears to work by inducing unscheduled expression of checkpoint molecules, e.g., E2F, independent of DNA damage and cell cycle stages. Several studies have shown that β-lapachone activates checkpoints and induces cell death in cancer cells from a variety of tissues without affecting normal cells from these tissues (U.S. Patent Application Publication No. 2002/0169135). In normal cells with their intact regulatory mechanisms, such an imposed expression of a checkpoint molecule results in a transient expression pattern and causes little consequence. In contrast, cancer and pre-cancer cells have defective mechanisms, which result in unchecked and persistent expression of unscheduled checkpoint molecules, e.g., E2F, leading to selective cell death in cancer and pre-cancer cells.

β-lapachone has been shown to be a DNA repair inhibitor that sensitizes cells to DNA-damaging agents including radiation (Boothman, D. A. et al., *Cancer Res*, 47 (1987) 5361; Boorstein, R. J., et al., *Biochem. Biophys. Commun.*, 117 (1983) 30). β-lapachone has also shown potent in vitro inhibition of human DNA Topoisomerases I (Li, C. J. et al., *J. Biol. Chem.*, 268 (1993) 22463) and II (Frydman, B. et al., *Cancer Res.*, 57 (1997) 620) with novel mechanisms of action. Unlike topoisomerase "poisons" (e.g., camptothecin, etoposide, doxorubicin) which stabilize the covalent topoisomerase-DNA complex and induce topoisomerase-mediated DNA cleavage, β-lapachone interacts directly with the enzyme to inhibit catalysis and block the formation of cleavable complex (Li, C. J. et al., *J. Biol. Chem.*, 268 (1993) 22463), or β-lapachone interacts with the complex itself, causing religation of DNA breaks and dissociation of the enzyme from DNA (Krishnan, P. et al., *Biochem Pharm*, 60 (2000) 1367). β-lapachone and its derivatives have also been synthesized and tested as anti-viral and anti-parasitic agents (Goncalves, A. M., et al., *Mol. Biochem. Parasitology*, 1 (1980) 167-176; Schaffner-Sabba, K., et al., *J. Med. Chem.*, 27 (1984) 990-994).

More specifically, β-lapachone appears to work by disrupting DNA replication, causing cell-cycle delays in G1 and/or S phase, inducing cell death in a wide variety of human carcinoma cell lines without DNA damage and independent of p53 status (Li, Y. Z. et al. (1999); Huang, L. et al.). Topoisomerase I is an enzyme that unwinds the DNA that makes up the chromosomes. The chromosomes must be unwound in order for the cell to use the genetic information to synthesize proteins; β-lapachone keeps the chromosomes wound tight, so that the cell cannot make proteins. As a result, the cell stops growing. Because cancer cells are constantly replicating and circumvent many mechanisms that restrict replication in normal cells, they are more vulnerable to topoisomerase inhibition than are normal cells.

Another possible intracellular target for β-lapachone in tumor cells is the enzyme NAP(P)H:quinone oxidoreductase (NQO1). Biochemical studies suggest that reduction of β-lapachone by NQO1 leads to a "futile cycling" between the quinone and hydroquinone forms with a concomitant loss of reduced NADH or NAD(P)H (Pink, J. J. et al., *J. Biol. Chem.*, 275 (2000) 5416). The exhaustion of these reduced enzyme cofactors may be a critical factor for the activation of cell death pathways after β-lapachone treatment. Reinicke et al. reach a similar conclusion using mono(arylimino) derivatives of β-lapachone (Reinicke et al., *Clin. Cancer. Res.* 11(8) (2005) 3055-64).

As a result of these findings, β-lapachone is actively being developed for the treatment of cancer and tumors. In WO 00/61142, for example, there is disclosed a method and composition for the treatment of cancer, which comprises the administration of an effective amount of a first compound, a G1 or S phase drug, such as a β-lapachone, in combination with a G2/M drug, such as a taxane derivative. Additionally, U.S. Pat. No. 6,245,807 discloses the use of β-lapachone, amongst other β-lapachone derivatives, for use in the treatment of human prostate disease.

In addition to β-lapachone, a number of β-lapachone analogs having anti-proliferative properties have been disclosed in the art, such as those described in PCT International Application PCT/US93/07878 (WO 94/04145), and U.S. Pat. No. 6,245,807, in which a variety of substituents may be attached at positions 3- and 4- on the β-lapachone compound. PCT International Application PCT/US00/10169 (WO 00/61142), discloses β-lapachone, which may have a variety of substituents at the 3-position as well as in place of the methyl groups attached at the 2-position. U.S. Pat. Nos. 5,763,625, 5,824, 700, and 5,969,163 disclose analogs with a variety of substituents at the 2-, 3- and 4-positions. Furthermore, a number of journals report β-lapachone analogs with substituents at one or more of the following positions: 2-, 3-, 8- and/or 9-positions. See, e.g., Sabba et al., (1984) *J Med Chem* 27:990-994 (substituents at the 2-, 8- and 9-positions); Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions).

Moreover, structures having sulfur-containing heterorings in the "α" and "β" positions of lapachone have been reported (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2): 163-169; and Krapcho A P et al., (1990) *Journal of Medicinal Chemistry* 33(9):2651-2655). More particularly, hetero β-lapachone analogs are disclosed in PCT/US2003/037219, which published as WO 04/045557.

One obstacle to the development of pharmaceutical formulations comprising β-lapachone or β-lapachone analogs for pharmaceutical use is the low solubility of β-lapachone compounds in pharmaceutically acceptable solvents. β-lapachone compounds are generally highly insoluble in water and have only limited solubility in common solvent systems used for pharmaceutical administration, specifically for intravenous delivery of drugs. As a result, there is a need for improved formulations of β-lapachone compounds for pharmaceutical administration, which are both safe and readily bioavailable to the subject to which the formulation is administered. Importantly, there is an additional need to provide compositions that target tumor tissue with anti-cancer agents such as β-lapachone in such a manner that reduces the potential side effects due to the agent being released at unwanted sites. This invention describes systems for the delivery of therapeutic agents having carbonyl or quinone functionalities, including β-lapachone compounds, to tumors in a manner that diminishes unwanted side effects. As the polymeric compositions and methods described herein bind carbonyl-containing or quinone-containing therapeutic agents through a cleavable linkage to the carbonyl or quinone functionalities, they can advantageously deliver the therapeutic agents without the introduction of additional functionalities that may alter the structure, function, activity, or metabolism of the released therapeutic agents.

SUMMARY OF THE INVENTION

The present invention provides for compositions comprising a carboxyl-containing polymer associated, via a linking agent of formula (I), with one or more carbonyl-containing or quinone-containing therapeutic agents, wherein said linking agent of formula (I) is associated with said one or more carbonyl-containing or quinone-containing therapeutic agents by an imine bond;

wherein said linking agent of formula (I) is of the form

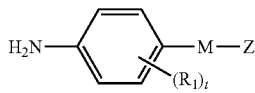

wherein
- M is selected from the group consisting of: —($C_1$-$C_8$) alkyl-, —($CH_2$)$_q$—O—($CH_2$)$_r$—, —C(=O)—O—($CH_2$)$_r$—, —($C_3$-$C_7$)cycloalkyl-, -aryl-C(=O)—O—($CH_2$)$_r$—, —C(=O)—O-aryl-($CH_2$)$_r$—, -heteroaryl-C(=O)—O—($CH_2$)—, and —C(=O)—O-heteroaryl-($CH_2$)$_r$—;
- Z is —OH, a protected amine, or a protected hydroxyl;
- each $R_1$ is independently selected from the group consisting of: hydrogen, halogen, and —($C_1$-$C_4$) alkyl;
- q is from 0-6;
- r is from 2-6; and
- t is from 0-4.

The present invention also provides for pharmaceutical compositions comprising a therapeutically effective amount of the foregoing composition comprising a carboxyl-containing polymer associated, via a linking agent of formula (I), with one or more carbonyl-containing or quinone-containing therapeutic agents, wherein said linking agent of formula (I) is associated with said one or more carbonyl-containing or quinone-containing therapeutic agents by an imine bond. In addition, the present invention also contemplates and provides for methods of treating cancer comprising administering to a subject in need thereof the foregoing pharmaceutical composition comprising a carboxyl-containing polymer associated, via a linking agent of formula (I), with one or more carbonyl-containing or quinone-containing therapeutic agents, wherein said linking agent of formula (I) is associated with said one or more carbonyl-containing or quinone-containing therapeutic agents by an imine bond.

The present invention provides for compositions comprising a carboxyl-containing polymer associated, via a linking agent of formula (I), with β-lapachone, wherein said linking agent of formula (I) is associated with said β-lapachone by an imine bond. The present invention also provides for a pharmaceutical composition comprising a therapeutically effective amount of a composition comprising a carboxyl-containing polymer associated, via a linking agent of formula (I), with β-lapachone, wherein said linking agent of formula (I) is associated with said β-lapachone by an imine bond. In addition, the present invention also contemplates and provides for methods of treating cancer comprising administering to a subject in need thereof any of the foregoing compositions comprising a carboxyl-containing polymer associated, via a linking agent of formula (I), with β-lapachone, wherein said linking agent of formula (I) is associated with said β-lapachone by an imine bond.

The present invention provides for compositions comprising a carboxyl-containing polymer associated, via a linking agent of formula (II), with one or more quinone-containing therapeutic agents, wherein said linking agent of formula (II) is associated with said one or more quinone-containing therapeutic agents by a quinol-ester;

wherein said linking agent of formula (II) is of the form

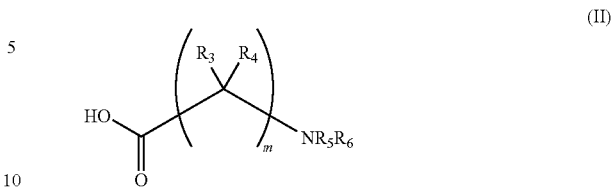

where
- each $R_3$ and $R_4$ are independently selected from the group consisting of hydrogen, —($C_1$-$C_8$) alkyl, —O—($C_1$-$C_8$) alkyl, —($C_1$-$C_4$) alkyl-aryl, aryl, and heteroaryl;
- $R_5$ is selected from the group consisting of hydrogen, —($C_1$-$C_8$) alkyl, —($C_1$-$C_8$) fluoroalkyl, aryl, and heteroaryl;
- $R_6$ is selected from the group consisting of tert-butoxycarbonyl and CBZ; and
- m is from 1 to 8;
- alternatively, when m is 1, $R_4$ and $R_5$ may be taken together with the carbon and nitrogen atoms bearing them to form a 4 to 7 membered nitrogen-containing heterocycle.

The present invention also provides for pharmaceutical compositions comprising a therapeutically effective amount of the foregoing composition comprising a carboxyl-containing polymer associated, via a linking agent of formula (II), with one or more quinone-containing therapeutic agents, wherein said linking agent of formula (II) is associated with said one or more quinone-containing therapeutic agents by a quinol-ester. In addition, the present invention also contemplates and provides for methods of treating cancer comprising administering to a subject in need thereof the foregoing pharmaceutical composition comprising a carboxyl-containing polymer associated, via a linking agent of formula (II), with one or more quinone-containing therapeutic agents, wherein said linking agent of formula (II) is associated with said one or more quinone-containing therapeutic agents by a quinol-ester.

The present invention provides for compositions comprising a carboxyl-containing polymer associated, via a linking agent of formula (II), with β-lapachone, wherein said linking agent of formula (II) is associated with said β-lapachone by a quinol-ester. The present invention also provides for a pharmaceutical composition comprising a therapeutically effective amount of the foregoing composition comprising a carboxyl-containing polymer associated, via a linking agent of formula (II), with β-lapachone, wherein said linking agent of formula (II) is associated with said β-lapachone by a quinol-ester. In addition, the present invention also contemplates and provides for methods of treating cancer comprising administering to a subject in need thereof the foregoing pharmaceutical composition comprising a carboxyl-containing polymer associated, via a linking agent of formula (II), with β-lapachone, wherein said linking agent of formula (II) is associated with said β-lapachone by a quinol-ester.

The present invention provides for compositions comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage;

wherein said linking agent of formula (III) is of the form

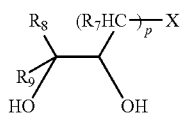

(III)

where
X is a hydroxyl, a protected hydroxyl or a protected amine;
each of $R_7$ and $R_8$ is independently selected from the group consisting of hydrogen, and $(C_1\text{-}C_4)$ alkyl;
$R_9$ is H; and
p is 1-4.

The present invention also provides for pharmaceutical compositions comprising a therapeutically effective amount of the foregoing composition comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage. In addition, the present invention also contemplates and provides for methods of treating cancer comprising administering to a subject in need thereof the foregoing pharmaceutical composition comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage.

The present invention provides for compositions comprising a carboxyl-containing polymer associated, via a linking agent of formula (III), with β-lapachone, wherein said linking agent of formula (III) is associated with said β-lapachone by a ketal linkage. The present invention also provides for a pharmaceutical composition comprising a therapeutically effective amount of the foregoing composition comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage. In addition, the present invention also contemplates and provides for methods of treating cancer comprising administering to a subject in need thereof the foregoing pharmaceutical composition comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage.

The present invention provides for methods of preparing a polymer-modified therapeutic agent comprising the steps of:
(i) providing a linking agent of formula (I):

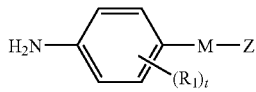

wherein
M is a spacer group selected from the group consisting of:
—$(C_1\text{-}C_8)$ alkyl-, —$(CH_2)_q$—O—$(CH_2)_r$—, —C(=O)—O—$(CH_2)_r$—, —$(C_3\text{-}C_7)$cycloalkyl-, -aryl-C(=O)—O—$(CH_2)_r$—, —C(=O)—O-aryl-$(CH_2)_r$—, -heteroaryl-C(=O)—O—$(CH_2)_r$—, and —C(=O)—O-heteroaryl-$(CH_2)_r$—;
Z is —OH, a protected amine, or a protected hydroxyl;
each $R_1$ is independently selected from the group consisting of: hydrogen, halogen, and —$(C_1\text{-}C_4)$ alkyl;
q is from 0-6;
r is from 2-6; and
t is from 0-4;
(ii) providing a quinone-containing therapeutic agent or a carbonyl-containing therapeutic agent;
(iii) contacting said linking agent of formula (I) with said quinone-containing therapeutic agent or said carbonyl-containing therapeutic agent under conditions for the formation of an imine bond there between, resulting in the formation of a linker conjugated therapeutic agent bearing a Z group;
(iv) providing a carboxyl-containing polymer; and
(v) contacting said carboxyl-containing polymer with said linker conjugated therapeutic agent under conditions wherein when said Z group is a hydroxyl Z forms an ester bond with said carboxyl-containing polymer, or wherein when said Z group is an amine Z forms an amide bond with a carboxyl group of said carboxyl-containing polymer.

In addition, the present invention provides for the products of the foregoing method. Moreover, in an embodiment, the present invention contemplates and provides for the products of the foregoing method wherein the quinone-containing therapeutic agent is mitomycin C, doxorubicin, actinomycin D (dactinomycin), or β-lapachone.

The present invention provides for methods of preparing a polymer-modified therapeutic agent comprising the steps of:
(i) providing a linking agent of formula (II)

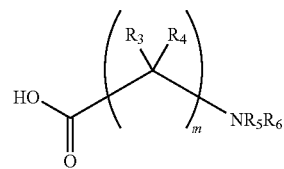

(II)

where
each $R_3$ and $R_4$ are independently selected from the group consisting of hydrogen, —$(C_1\text{-}C_8)$ alkyl, —O—$(C_1\text{-}C_8)$ alkyl, —$(C_1\text{-}C_4)$ alkyl-aryl, aryl, and heteroaryl;
$R_5$ is selected from the group consisting of hydrogen, —$(C_1\text{-}C_8)$ alkyl, —$(C_1\text{-}C_8)$ fluoroalkyl, aryl, and heteroaryl;
$R_6$ is selected from the group consisting of -tert-butoxycarbonyl and CBZ; and
m is from 1 to 8;
alternatively, when m is 1, $R_4$ and $R_5$ may be taken together with the carbon and nitrogen atoms bearing them to form a 4 to 7 membered nitrogen-containing heterocycle;
(ii) providing a quinone-containing therapeutic agent;
(iii) providing an alkyl carboxylic acid of the formula $R_2$COOH, wherein $R_2$ is $(C_1\text{-}C_8)$ alkyl, cycloalkyl, aryl, heterocycle, heteroaryl, aryl-alkyl, or alkylaryl, and wherein said alkyl and cycloalkyl groups within $R_2$ may be substituted with one or more substituents independently selected from the group consisting of —H and —F, and wherein said aryl groups within $R_2$ may be substituted with one or more substituents independently selected from the group consisting of —H and halogen;

(iv) contacting said linking agent of formula (II) with said quinone-containing therapeutic agent and said alkyl carboxylic acid of formula $R_2COOH$ under conditions for the formation of a quinol-ester linker conjugated therapeutic agent;
(v) converting $R_6$ to hydrogen by deprotection to form a deprotected quinol-ester linker conjugated therapeutic agent bearing an amine group;
(vi) providing a carboxyl-containing polymer; and
(vii) contacting said carboxyl-containing polymer with said deprotected quinol-ester linker conjugated therapeutic agent bearing an amine group under conditions where said amine group forms an amide bond with a carboxyl group of said carboxyl-containing polymer.

In addition, the present invention provides for the products of the foregoing method. Moreover, in an embodiment, the present invention contemplates and provides for the products of the foregoing method wherein the quinone-containing therapeutic agent is mitomycin C, doxorubicin, actinomycin D (dactinomycin), or β-lapachone.

The present invention provides for methods of preparing a polymer-modified therapeutic agent comprising the steps of:
(i) providing a linking agent of formula (III)

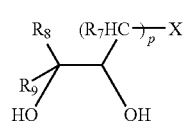

(III)

where
X is a hydroxyl, a protected hydroxyl or a protected amine;
each of $R_7$ and $R_8$ is independently selected from the group consisting of hydrogen, and $(C_1-C_4)$ alkyl;
$R_9$ is H; and
p is 1-4;
(ii) providing a quinone-containing or carbonyl-containing therapeutic agent;
(iii) contacting said linking agent of formula (III) with said quinone-containing or said carbonyl-containing therapeutic agent under conditions for the formation of a ketal linker conjugated therapeutic agent;
(iv) where X is a protected hydroxyl or a protected amine, converting it to an amine of the form $-NH_2$ by deprotection to form a deprotected ketal linker conjugated therapeutic agent;
(v) providing a carboxyl-containing polymer; and
(vi) contacting said carboxyl-containing polymer with said ketal linker conjugated therapeutic agent or said deprotected ketal linker conjugated therapeutic agent under conditions wherein when X is a hydroxyl, X forms an ester bond with said carboxyl-containing polymer, or wherein when X is $-NH_2$ X forms an amide bond with said carboxyl-containing polymer.

In addition, the present invention provides for the products of the foregoing method. Moreover, in an embodiment, the present invention contemplates and provides for the products of the foregoing method wherein the quinone-containing therapeutic agent is mitomycin C, doxorubicin, actinomycin D (dactinomycin), or β-lapachone.

CERTAIN EMBODIMENTS

The present invention provides for certain embodiments of carboxyl-containing polymers wherein said carboxyl-containing polymer is a PGA polymer, and said carboxyl-containing polymer comprises one or more residues of the form

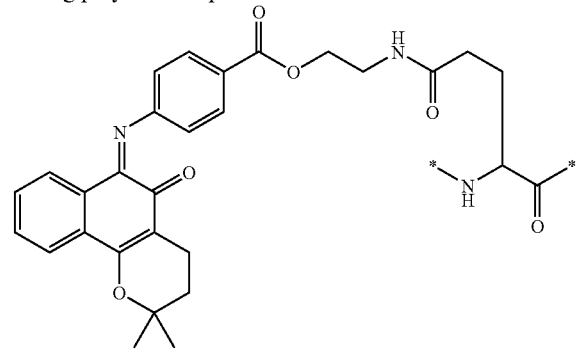

where "*" indicates the points of attachment to other residues of said PGA polymer.

The present invention provides for certain embodiments of carboxyl-containing polymers wherein said carboxyl-containing polymer is a PGA polymer, and said carboxyl-containing polymer comprises one or more residues of the form

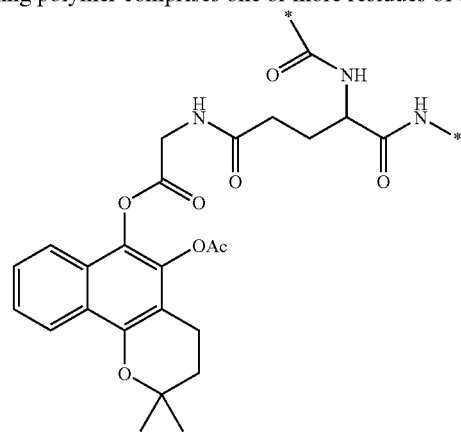

where "*" indicates the points of attachment to other residues of said PGA polymer.

The present invention provides for certain embodiments of carboxyl-containing polymers wherein said carboxyl-containing polymer is a PGA polymer and said carboxyl-containing polymer comprises one or more residues of the form

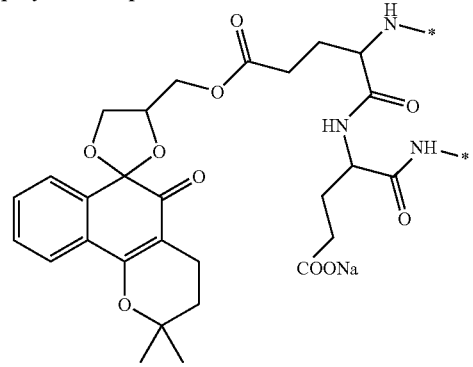

where "*" indicates the points of attachment to other residues of said PGA polymer.

The present invention also provides for the following embodiments:

Embodiment 1

A composition comprising a carboxyl-containing polymer associated, via a linking agent of formula (I), with one or more carbonyl-containing or quinone-containing therapeutic agents, wherein said linking agent of formula (I) is associated with said one or more carbonyl-containing or quinone-containing therapeutic agents by an imine bond;

wherein said linking agent of formula (I) is of the form $$H_2N-\underset{(R_1)_t}{\underset{|}{\bigcirc}}-M-Z$$

wherein
- M is selected from the group consisting of: $-(C_1-C_8)$alkyl-, $-(CH_2)_q-O-(CH_2)_r-$, $-C(=O)-O-(CH_2)_r-$, $-(C_3-C_7)$cycloalkyl-, -aryl-$C(=O)-O-(CH_2)_r-$, $-C(=O)-O$-aryl-$(CH_2)_r-$, -heteroaryl-$C(=O)-O-(CH_2)_r-$, and $-C(=O)-O$-heteroaryl-$(CH_2)_r-$;
- Z is —OH, a protected amine, or a protected hydroxyl;
- each $R_1$ is independently selected from the group consisting of: hydrogen, halogen, and $-(C_1-C_4)$ alkyl;
- q is from 0-6;
- r is from 2-6; and
- t is from 0-4.

Embodiment 2

The composition of embodiment 1, wherein said one or more carbonyl-containing or quinone-containing therapeutic agents is β-lapachone.

Embodiment 3

The composition of embodiment 1, wherein said carboxyl-containing polymer is a PEG-dicarboxylic acid, SMA, PGA or PAA polymer.

Embodiment 4

The composition of embodiment 1, wherein said one or more carbonyl-containing or quinone-containing therapeutic agents is β-lapachone, and said carboxyl-containing polymer is a PEG-dicarboxylic acid, SMA, PGA or PAA polymer.

Embodiment 5

The composition of embodiment 4, wherein said carboxyl-containing polymer is a PGA polymer, and said carboxyl-containing polymer comprises one or more residues of the form where "*" indicates the points of attachment to other residues of said PGA polymer.

Embodiment 6

A pharmaceutical composition comprising a therapeutically effective amount of a composition of any of embodiments 1-5.

Embodiment 7

The pharmaceutical composition of embodiment 6, further comprising one or more pharmaceutically acceptable excipients.

Embodiment 8

The pharmaceutical composition of embodiment 6, wherein said pharmaceutical composition is a lyophilized powder.

Embodiment 9

The pharmaceutical composition of embodiment 6, wherein said pharmaceutical composition is a formulation for oral administration.

Embodiment 10

The pharmaceutical composition of embodiment 6, wherein said pharmaceutical composition is a formulation for parenteral administration.

Embodiment 11

The pharmaceutical composition of embodiment 6, wherein said pharmaceutical composition is a formulation for intravenous administration.

Embodiment 12

A method of treating cancer comprising administering to a subject in need thereof the pharmaceutical composition of embodiment 6.

Embodiment 13

The method of treating cancer of embodiment 12, wherein said cancer is lung cancer, breast cancer, colon cancer, ovarian cancer, prostate cancer, multiple myeloma or malignant melanoma.

Embodiment 14

The method of treating cancer of embodiment 12, wherein said pharmaceutical composition is administered orally.

Embodiment 15

The method of treating cancer of embodiment 12, wherein said pharmaceutical composition is administered parenterally.

Embodiment 16

The method of treating cancer of embodiment 12, wherein said pharmaceutical composition is administered intravenously.

Embodiment 17

The method of treating cancer of embodiment 12, further comprising administering a second anti-cancer agent.

Embodiment 18

A composition comprising a carboxyl-containing polymer associated, via a linking agent of formula (I), with β-lapachone, wherein said linking agent of formula (I) is associated with said β-lapachone by an imine bond.

Embodiment 19

The composition of embodiment 18, wherein said carboxyl-containing polymer is a PEG-dicarboxylic acid, SMA, PGA or PAA polymer.

Embodiment 20

A pharmaceutical composition comprising a therapeutically effective amount of a composition of either embodiment 18 or embodiment 19.

Embodiment 21

The pharmaceutical composition of embodiment 20, further comprising one or more pharmaceutically acceptable excipients.

Embodiment 22

The pharmaceutical composition of embodiment 20, wherein said pharmaceutical composition is a lyophilized powder.

Embodiment 23

The pharmaceutical composition of embodiment 20, wherein said pharmaceutical composition is a formulation for oral administration.

Embodiment 24

The pharmaceutical composition of embodiment 20, wherein said pharmaceutical composition is a formulation for parenteral administration.

Embodiment 25

The pharmaceutical composition of embodiment 20, wherein said pharmaceutical composition is a formulation for intravenous administration.

Embodiment 26

A method of treating cancer comprising administering to a subject in need thereof the pharmaceutical composition of embodiment 20.

Embodiment 27

The method of treating cancer of embodiment 26, wherein said cancer is lung cancer, breast cancer, colon cancer, ovarian cancer, prostate cancer, multiple myeloma or malignant melanoma.

Embodiment 28

The method of treating cancer of embodiment 26, wherein said pharmaceutical composition is administered orally.

Embodiment 29

The method of treating cancer of embodiment 26, wherein said pharmaceutical composition is administered parenterally.

Embodiment 30

The method of treating cancer of embodiment 26, wherein said pharmaceutical composition is administered intravenously.

Embodiment 31

The method of treating cancer of embodiment 26, further comprising administering a second anti-cancer agent.

Embodiment 32

A composition comprising a carboxyl-containing polymer associated, via a linking agent of formula (II), with one or more quinone-containing therapeutic agents, wherein said linking agent of formula (II) is associated with said one or more quinone-containing therapeutic agents by a quinol-ester;

wherein said linking agent of formula (II) is of the form

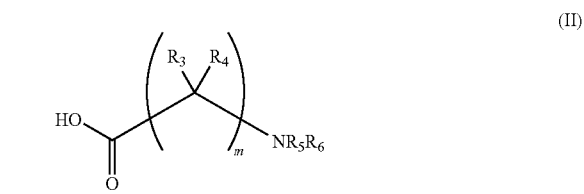

where
each $R_3$ and $R_4$ are independently selected from the group consisting of hydrogen, —$(C_1\text{-}C_8)$ alkyl, —O—$(C_1\text{-}C_8)$ alkyl, —$(C_1\text{-}C_4)$ alkyl-aryl, aryl, and heteroaryl;

R₅ is selected from the group consisting of hydrogen, —(C₁-C₈) alkyl, —(C₁-C₈) fluoroalkyl, aryl, and heteroaryl;
R₆ is selected from the group consisting of -tert-butoxycarbonyl and CBZ; and
m is from 1 to 8;
alternatively, when m is 1, R₄ and R₅ may be taken together with the carbon and nitrogen atoms bearing them to form a 4 to 7 membered nitrogen-containing heterocycle.

Embodiment 33

The composition of embodiment 32, wherein said one or more quinone-containing therapeutic agents is β-lapachone.

Embodiment 34

The composition of embodiment 32, wherein said carboxyl-containing polymer is a PEG-dicarboxylic acid, SMA, PGA or PAA polymer.

Embodiment 35

The composition of embodiment 32, wherein said one or more quinone-containing therapeutic agents is β-lapachone, and said carboxyl-containing polymer is a PEG-dicarboxylic acid, SMA, PGA or PAA polymer.

Embodiment 36

The composition of embodiment 32, wherein said carboxyl-containing polymer is a PGA polymer, and said carboxyl-containing polymer comprises one or more residues of the form

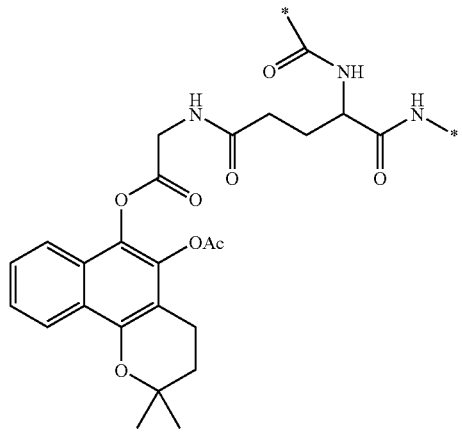

where "*" indicates the points of attachment to other residues of said PGA polymer.

Embodiment 37

A pharmaceutical composition comprising a therapeutically effective amount of a composition of any of embodiments 32-36.

Embodiment 38

The pharmaceutical composition of embodiment 37, further comprising one or more pharmaceutically acceptable excipients.

Embodiment 39

The pharmaceutical composition of embodiment 37, wherein said pharmaceutical composition is a lyophilized powder.

Embodiment 40

The pharmaceutical composition of embodiment 37, wherein said pharmaceutical composition is a formulation for oral administration.

Embodiment 41

The pharmaceutical composition of embodiment 37, wherein said pharmaceutical composition is a formulation for parenteral administration.

Embodiment 42

The pharmaceutical composition of embodiment 37, wherein said pharmaceutical composition is a formulation for intravenous administration.

Embodiment 43

A method of treating cancer comprising administering to a subject in need thereof the pharmaceutical composition of embodiment 37.

Embodiment 44

The method of treating cancer of embodiment 43, wherein said cancer is lung cancer, breast cancer, colon cancer, ovarian cancer, prostate cancer, multiple myeloma or malignant melanoma.

Embodiment 45

The method of treating cancer of embodiment 43, wherein said pharmaceutical composition is administered orally.

Embodiment 46

The method of treating cancer of embodiment 43, wherein said pharmaceutical composition is administered parenterally.

Embodiment 47

The method of treating cancer of embodiment 43, wherein said pharmaceutical composition is administered intravenously.

Embodiment 48

The method of treating cancer of embodiment 43, further comprising administering a second anti-cancer agent.

Embodiment 49

A composition comprising a carboxyl-containing polymer associated, via a linking agent of formula (II), with β-lapachone, wherein said linking agent of formula (II) is associated with said β-lapachone by a quinol-ester.

Embodiment 50

The composition of embodiment 49, wherein said carboxyl-containing polymer is a PEG-dicarboxylic acid, SMA, PGA or PAA polymer.

Embodiment 51

A pharmaceutical composition comprising a therapeutically effective amount of a composition of either embodiment 49 or embodiment 50.

Embodiment 52

The pharmaceutical composition of embodiment 51, further comprising one or more pharmaceutically acceptable excipients.

Embodiment 53

The pharmaceutical composition of embodiment 51, wherein said pharmaceutical composition is a lyophilized powder.

Embodiment 54

The pharmaceutical composition of embodiment 51, wherein said pharmaceutical composition is a formulation for oral administration.

Embodiment 55

The pharmaceutical composition of embodiment 51, wherein said pharmaceutical composition is a formulation for parenteral administration.

Embodiment 56

The pharmaceutical composition of embodiment 51, wherein said pharmaceutical composition is a formulation for intravenous administration.

Embodiment 57

A method of treating cancer comprising administering to a subject in need thereof the pharmaceutical composition of embodiment 51.

Embodiment 58

The method of treating cancer of embodiment 57, wherein said cancer is lung cancer, breast cancer, colon cancer, ovarian cancer, prostate cancer, multiple myeloma or malignant melanoma.

Embodiment 59

The method of treating cancer of embodiment 57, wherein said pharmaceutical composition is administered orally.

Embodiment 60

The method of treating cancer of embodiment 57, wherein said pharmaceutical composition is administered parenterally.

Embodiment 61

The method of treating cancer of embodiment 57, wherein said pharmaceutical composition is administered intravenously.

Embodiment 62

The method of treating cancer of embodiment 57, further comprising administering a second anti-cancer agent.

Embodiment 63

A composition comprising a carboxyl-containing polymer associated, via a linking agent of formula (III), with one or more quinone-containing therapeutic agents, wherein said linking agent of formula (III) is associated with said one or more quinone-containing therapeutic agents by a ketal linkage;

wherein said linking agent of formula (III) is of the form

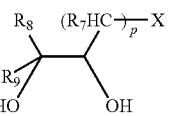

(III)

where
X is a hydroxyl, a protected hydroxyl or a protected amine;
each of $R_7$ and $R_8$ is independently selected from the group consisting of hydrogen, and $(C_1-C_4)$ alkyl;
$R_9$ is H; and
p is 1-4.

Embodiment 64

The composition of embodiment 63, wherein said one or more quinone-containing therapeutic agents is β-lapachone.

Embodiment 65

The composition of embodiment 63, wherein said carboxyl-containing polymer is a PEG-dicarboxylic acid, SMA, PGA or PAA polymer.

Embodiment 66

The composition of embodiment 63, wherein said one or more quinone-containing therapeutic agents is β-lapachone, and said carboxyl-containing polymer is a PEG-dicarboxylic acid, SMA, PGA or PAA polymer.

Embodiment 67

The composition of embodiment 66, wherein said carboxyl-containing polymer is a PGA polymer, and said carboxyl-containing polymer comprises one or more residues of the form

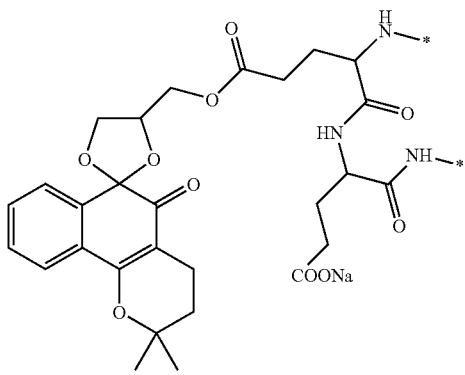

where "*" indicates the points of attachment to other residues of said PGA polymer.

Embodiment 68

A pharmaceutical composition comprising a therapeutically effective amount of a composition of any of embodiments 63-67.

Embodiment 69

The pharmaceutical composition of embodiment 68, further comprising one or more pharmaceutically acceptable excipients.

Embodiment 70

The pharmaceutical composition of embodiment 68, wherein said pharmaceutical composition is a lyophilized powder.

Embodiment 71

The pharmaceutical composition of embodiment 68, wherein said pharmaceutical composition is a formulation for oral administration.

Embodiment 72

The pharmaceutical composition of embodiment 68, wherein said pharmaceutical composition is a formulation for parenteral administration.

Embodiment 73

The pharmaceutical composition of embodiment 68, wherein said pharmaceutical composition is a formulation for intravenous administration.

Embodiment 74

A method of treating cancer comprising administering to a subject in need thereof the pharmaceutical composition of embodiment 68.

Embodiment 75

The method of treating cancer of embodiment 74, wherein said cancer is lung cancer, breast cancer, colon cancer, ovarian cancer, prostate cancer, multiple myeloma or malignant melanoma.

Embodiment 76

The method of treating cancer of embodiment 74, wherein said pharmaceutical composition is administered orally.

Embodiment 77

The method of treating cancer of embodiment 74, wherein said pharmaceutical composition is administered parenterally.

Embodiment 78

The method of treating cancer of embodiment 74, wherein said pharmaceutical composition is administered intravenously.

Embodiment 79

The method of treating cancer of embodiment 74, further comprising administering a second anti-cancer agent.

Embodiment 80

A composition comprising a carboxyl-containing polymer associated, via a linking agent of formula (III), with β-lapachone, wherein said linking agent of formula (III) is associated with said β-lapachone by a ketal linkage.

Embodiment 81

The composition of embodiment 80, wherein said carboxyl-containing polymer is a PEG-dicarboxylic acid, SMA, PGA or PAA polymer.

Embodiment 82

A pharmaceutical composition comprising a therapeutically effective amount of a composition of either embodiment 80 or embodiment 81.

Embodiment 83

The pharmaceutical composition of embodiment 82, further comprising one or more pharmaceutically acceptable excipients.

Embodiment 84

The pharmaceutical composition of embodiment 82, wherein said pharmaceutical composition is a lyophilized powder.

Embodiment 85

The pharmaceutical composition of embodiment 82, wherein said pharmaceutical composition is a formulation for oral administration.

Embodiment 86

The pharmaceutical composition of embodiment 82, wherein said pharmaceutical composition is a formulation for parenteral administration.

Embodiment 87

The pharmaceutical composition of embodiment 82, wherein said pharmaceutical composition is a formulation for intravenous administration.

Embodiment 88

A method of treating cancer comprising administering to a subject in need thereof the pharmaceutical composition of embodiment 82.

Embodiment 89

The method of treating cancer of embodiment 88, wherein said cancer is lung cancer, breast cancer, colon cancer, ovarian cancer, prostate cancer, multiple myeloma or malignant melanoma.

Embodiment 90

The method of treating cancer of embodiment 88, wherein said pharmaceutical composition is administered orally.

Embodiment 91

The method of treating cancer of embodiment 88, wherein said pharmaceutical composition is administered parenterally.

Embodiment 92

The method of treating cancer of embodiment 88, wherein said pharmaceutical composition is administered intravenously.

Embodiment 93

The method of treating cancer of embodiment 88, further comprising administering a second anti-cancer agent.

Embodiment 94

A method of preparing a polymer-modified therapeutic agent comprising the steps of:
(i) providing a linking agent of formula (I):

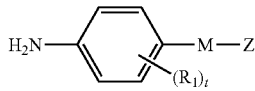

wherein
M is a spacer group selected from the group consisting of: —$(C_1-C_8)$ alkyl-, —$(CH_2)_q$—O—$(CH_2)_r$—, —C(=O)—O—$(CH_2)_r$—, —$(C_3-C_7)$cycloalkyl-, -aryl-C(=O)—O—$(CH_2)_r$—, —C(=O)—O-aryl-$(CH_2)_r$—, -heteroaryl-C(=O)—O—$(CH_2)_r$—, and —C(=O)—O-heteroaryl-$(CH_2)_r$—;
Z is —OH, a protected amine, or a protected hydroxyl;
each $R_1$ is independently selected from the group consisting of: hydrogen, halogen, and —$(C_1-C_4)$ alkyl;
q is from 0-6;
r is from 2-6; and
t is from 0-4;

(ii) providing a quinone-containing therapeutic agent or a carbonyl-containing therapeutic agent;
(iii) contacting said linking agent of formula (I) with said quinone-containing therapeutic agent or said carbonyl-containing therapeutic agent under conditions for the formation of an imine bond there between, resulting in the formation of a linker conjugated therapeutic agent bearing a Z group;
(iv) providing a carboxyl-containing polymer; and
(v) contacting said carboxyl-containing polymer with said linker conjugated therapeutic agent under conditions wherein when said Z group is a hydroxyl Z forms an ester bond with said carboxyl-containing polymer, or wherein when said Z group is an amine Z forms an amide bond with a carboxyl group of said carboxyl-containing polymer.

Embodiment 95

The method of embodiment 94, wherein when said Z group of said linker conjugated therapeutic agent is a protected amine, or a protected hydroxyl, said protected amine, or protected hydroxyl is deprotected prior to contacting said carboxyl-containing polymer with said linker conjugated therapeutic agent in step (v).

Embodiment 96

The method of embodiments 94 or 95, where said carboxyl-containing polymer is a PEG-dicarboxylic acid, PGA, PAA or SMA polymer.

Embodiment 97

The product produced by the method of embodiments 94 or 95.

Embodiment 98

The product produced by the method of embodiments 94 or 95, wherein said quinone-containing therapeutic agent is mitomycin C, doxorubicin, actinomycin D (dactinomycin), or β-lapachone.

Embodiment 99

The product produced by the method of embodiment 94 or 95 wherein said quinone-containing therapeutic agent is β-lapachone.

Embodiment 100

The product produced by the method of embodiment 97, where said carboxyl-containing polymer is a PEG-dicarboxylic acid, PGA, PAA or SMA polymer.

Embodiment 101

The product produced by the method of embodiment 98, where said carboxyl-containing polymer is a PEG-dicarboxylic acid, PGA, PAA or SMA polymer.

Embodiment 102

The product produced by the method of embodiment 99, where said carboxyl-containing polymer is a PEG-dicarboxylic acid, PGA, PAA or SMA polymer.

Embodiment 103

A method of preparing a polymer-modified therapeutic agent comprising the steps of:
(i) providing a linking agent of formula (II)

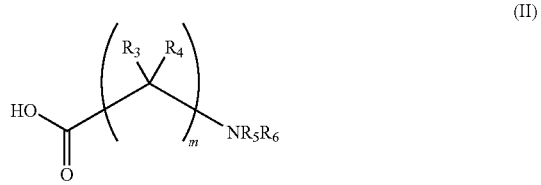

where
each $R_3$ and $R_4$ are independently selected from the group consisting of hydrogen, —($C_1$-$C_8$) alkyl, —O—($C_1$-$C_8$) alkyl, —($C_1$-$C_4$) alkyl-aryl, aryl, and heteroaryl;
$R_5$ is selected from the group consisting of hydrogen, —($C_1$-$C_8$) alkyl, —($C_1$-$C_8$) fluoroalkyl, aryl, and heteroaryl;
$R_6$ is selected from the group consisting of -tert-butoxycarbonyl and CBZ; and
m is from 1 to 8;
alternatively, when m is 1, $R_4$ and $R_5$ may be taken together with the carbon and nitrogen atoms bearing them to form a 4 to 7 membered nitrogen-containing heterocycle;
(ii) providing a quinone-containing therapeutic agent;
(iii) providing an alkyl carboxylic acid of the formula $R_2COOH$, wherein $R_2$ is ($C_1$-$C_8$) alkyl, cycloalkyl, aryl, heterocycle, heteroaryl, aryl-alkyl, or alkylaryl, and wherein said alkyl and cycloalkyl groups within $R_2$ may be substituted with one or more substituents independently selected from the group consisting of —H and —F, and wherein said aryl groups within $R_2$ may be substituted with one or more substituents independently selected from the group consisting of —H and halogen;
(iv) contacting said linking agent of formula (II) with said quinone-containing therapeutic agent and said alkyl carboxylic acid of formula $R_2COOH$ under conditions for the formation of a quinol-ester linker conjugated therapeutic agent;
(v) converting $R_6$ to hydrogen by deprotection to form a deprotected quinol-ester linker conjugated therapeutic agent bearing an amine group;
(vi) providing a carboxyl-containing polymer; and
(vii) contacting said carboxyl-containing polymer with said deprotected quinol-ester linker conjugated therapeutic agent bearing an amine group under conditions where said amine group forms an amide bond with a carboxyl group of said carboxyl-containing polymer.

Embodiment 104

The method of embodiment 103, where said carboxyl-containing polymer is a PEG-dicarboxylic acid, PGA, PAA or SMA polymer.

Embodiment 105

The product produced by the method of embodiments 103 or 104.

Embodiment 106

The product produced by the method of embodiments 103 or 104, wherein said quinone-containing therapeutic agent is mitomycin C, doxorubicin, actinomycin D (dactinomycin), or β-lapachone.

Embodiment 107

The product produced by the method of embodiments 103 or 104, wherein said quinone-containing therapeutic agent is β-lapachone.

Embodiment 108

A method of preparing a polymer-modified therapeutic agent comprising the steps of:
(i) providing a linking agent of formula (III)

where
X is a hydroxyl, a protected hydroxyl or a protected amine;
each of $R_7$ and $R_8$ is independently selected from the group consisting of hydrogen, and ($C_1$-$C_4$) alkyl;
$R_9$ is H; and
p is 1-4;
(ii) providing a quinone-containing or carbonyl-containing therapeutic agent;
(iii) contacting said linking agent of formula (III) with said quinone-containing or said carbonyl-containing therapeutic agent under conditions for the formation of a ketal linker conjugated therapeutic agent;
(iv) where X is a protected hydroxyl or a protected amine, converting it an amine of the form —$NH_2$ by deprotection to form a deprotected ketal linker conjugated therapeutic agent;
(v) providing a carboxyl-containing polymer; and
(vi) contacting said carboxyl-containing polymer with said ketal linker conjugated therapeutic agent or said deprotected ketal linker conjugated therapeutic agent under conditions wherein when X is a hydroxyl, X forms an ester bond with said carboxyl-containing polymer, or wherein when X is —$NH_2$ X forms an amide bond with said carboxyl-containing polymer.

Embodiment 109

The method of embodiment 108, where said carboxyl-containing polymer is a PEG-dicarboxylic acid, PGA, PAA or SMA polymer.

Embodiment 110

The product produced by the method of embodiments 108 or 109.

Embodiment 111

The product produced by the method of embodiments 108 or 109, wherein said quinone-containing therapeutic agent is mitomycin C, doxorubicin, actinomycin D (dactinomycin), or β-lapachone.

Embodiment 112

The product produced by the method of embodiments 108 or 109, wherein said quinone-containing therapeutic agent is β-lapachone.

Embodiment 113

A method for increasing the stability of a quinone-containing therapeutic agent in serum comprising administering to a subject in need thereof a therapeutically effective amount of a composition of embodiments 1, 18, 32, 49, 63 or 80 comprising a polymer-modified quinone-containing therapeutic agent, wherein the stability of said quinone-containing therapeutic agent in said serum is increased.

Embodiment 114

A method for increasing the concentration of a quinone-containing therapeutic agent in serum comprising administering to a subject in need thereof a therapeutically effective amount of a composition of embodiments 1, 18, 32, 49, 63 or 80 comprising a polymer-modified quinone-containing therapeutic agent, wherein the concentration of said quinone-containing therapeutic agent in said serum is increased.

Embodiment 115

A method for delivering a quinone-containing therapeutic agent or carbonyl-containing therapeutic agent to a tumor tissue comprising administering to a subject in need thereof a therapeutically effective amount of a composition of embodiments 1, 18, 32, 49, 63 or 80 comprising a polymer-modified quinone-containing therapeutic agent or a polymer-modified carbonyl-containing therapeutic agent.

Embodiment 116

The method of embodiment 115, where said composition comprises a quinone-containing therapeutic agent.

Embodiment 117

The method of embodiment 116, where said composition comprises a carbonyl-containing therapeutic agent.

Embodiment 118

The method of embodiments 115, 116, or 117, wherein the half-life of said quinone-containing therapeutic agent or carbonyl-containing therapeutic agent is increased in said tumor tissue as compared to the half-life of said quinone-containing therapeutic agent or carbonyl-containing therapeutic agent administered as an intravenous bolus.

BRIEF DESCRIPTION OF THE DRAWINGS

FIG. 5A: free β-lapachone (■ and ▲, Table 1: Samples B and D, respectively) in tumors; total β-lapachone (□ and Δ, Table 1: Samples B and D, respectively) in tumors; β-lapachone reference tumor (◆). FIG. 5B: free β-lapachone (■ and ▲, Table 1: Samples B and D, respectively) in plasma; total β-lapachone (□ and Δ, Table 1: Samples B and D, respectively) in plasma; and β-lapachone reference plasma ◆).

DETAILED DESCRIPTION OF THE INVENTION

Figure 1:
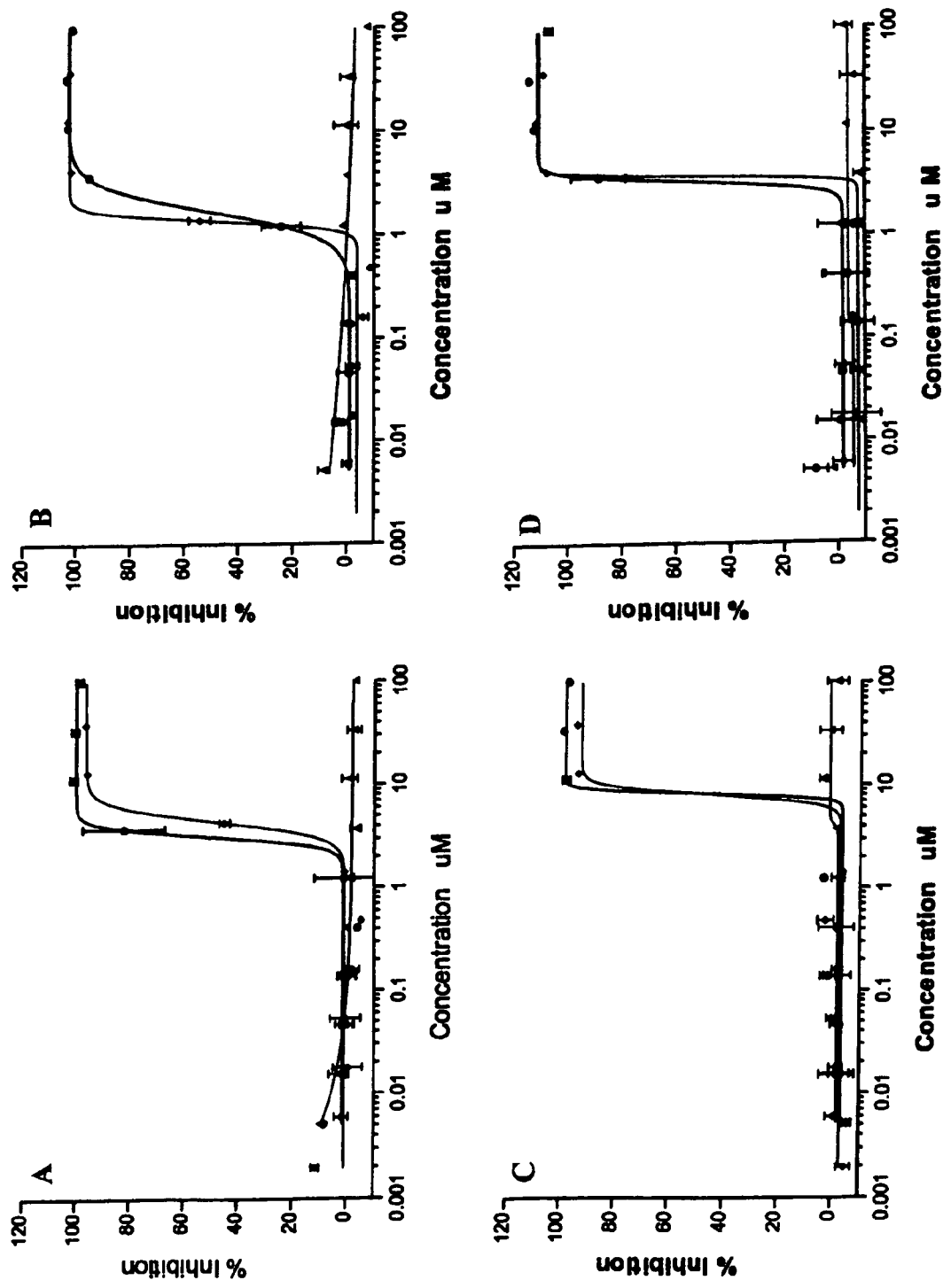
FIG. 1 sets forth measurements of the effects of β-lapachone (2,2-dimethyl-3,4-dihydro-2H-benzo[h]chromen-5,6-dione) (in DMSO) (●), and the polymer-modified β-lapachone compositions 5-(acetyloxy)-2,2-dimethyl-3,4-dihydro-2H-benzo[h]chromen-6-yl glycinate γ-poly-L-glutamate (in PEG/water) (♦) and (2,2-dimethyl-5-oxo-3,4-dihydro-2H,5H-spiro[benzo[h]chromene-6,2'-[1,3]dioxolan]-4'-yl)methyl γ-poly-L-glutamate sodium (in water) (▲) on the proliferation of DLD-1 cells and NCM-460 cells at 20 and 72 hours. Panel A indicates the effects on DLD-1 cells at 20 hours, Panel B indicates the effects on DLD-1 cells at 72 hours, Panel C indicates the effects on NCM-460 cells at 20 hours, and Panel D indicates the effects on NCM-460 cells at 72 hours. Estimates of the $IC_{50}$ (μM) are given in Table 2. Experimental details are set forth in Example 12.
Figure 2:
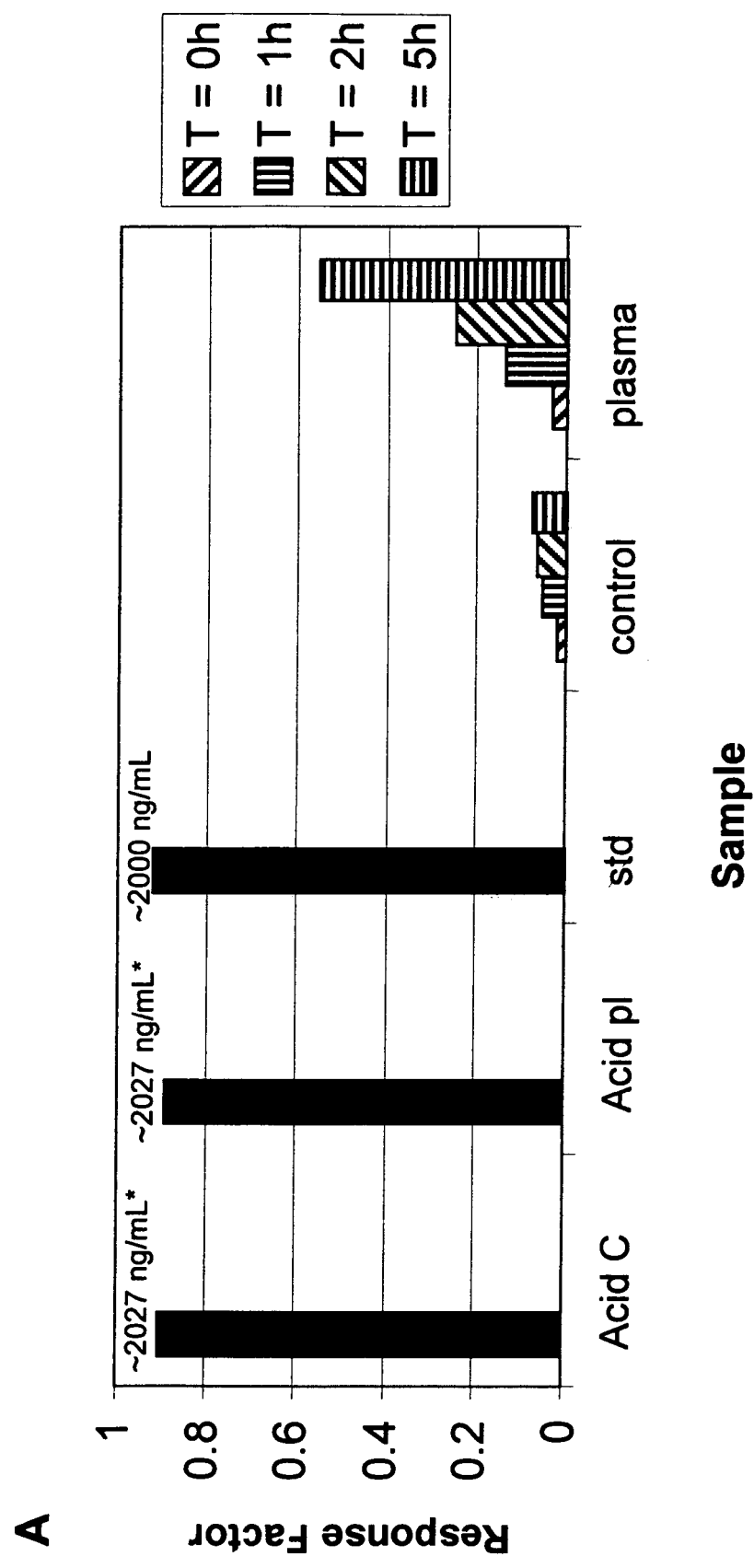
FIG. 2, Panel A sets forth the release of free β-lapachone (2,2-dimethyl-3,4-dihydro-2H-benzo[h]chromene-5,6-dione) from 5-(acetyloxy)-2,2-dimethyl-3,4-dihydro-2H-benzo[h]chromen-6-yl glycinate γ-poly-L-glutamate (Table 1: Sample B), Panel B sets forth the release of free β-lapachone from (2,2-dimethyl-5-oxo-3,4-dihydro-2H,5H-spiro[benzo[h]chromene-6,2'-[1,3]dioxolan]-4'-yl)methyl γ-poly-L-glutamate sodium (Table 1: Sample J), Panel C sets forth the release of free β-lapachone from N-{2-[(4-{[(6Z)-2,2-dimethyl-5-oxo-3,4-dihydro-2H-benzo[h]-chromen-6 (5H)-ylidene]amino}benzoyl)oxy]ethyl} γ-poly-L-glutamate (Table 1: Sample B), and Panel D sets forth the release of free β-lapachone from (2,2-dimethyl-3,4-dihydro-2H-benzo[h]chromene-5,6-dione) from 5-(acetyloxy)-2,2-dimethyl-3,4-dihydro-2H-benzo[h]chromen-6-yl glycinate γ-poly-L-glutamate (Table 1: Sample D) in control buffer and in plasma. Cleavage of β-lapachone from the polymer conjugates in control buffer and in plasma is conducted for the indicated times (T) given in hours (h). Control acid (HCl) cleavage of the polyglutamic conjugates in buffer is indicated by the results labeled "Acid C." Control acid (HCl) cleavage of the polyglutamic conjugate in plasma is indicated by the results labeled "Acid pl." Control base (NaOH) cleavage of the polyglutamic conjugates in buffer is indicated by the results labeled "base C." Control base (NaOH) cleavage of the polyglutamic conjugate in plasma is indicated by the results labeled "base pl," and control standard of β-lapachone is labeled "std." The response factor indicates the relative instrument response to β-lapachone, and values associated with the "*" indicate the theoretical β-lapachone concentrations based upon the percentage loading of the respective conjugates. Experimental details are set forth in Examples 13 and 14.
Figure 2:
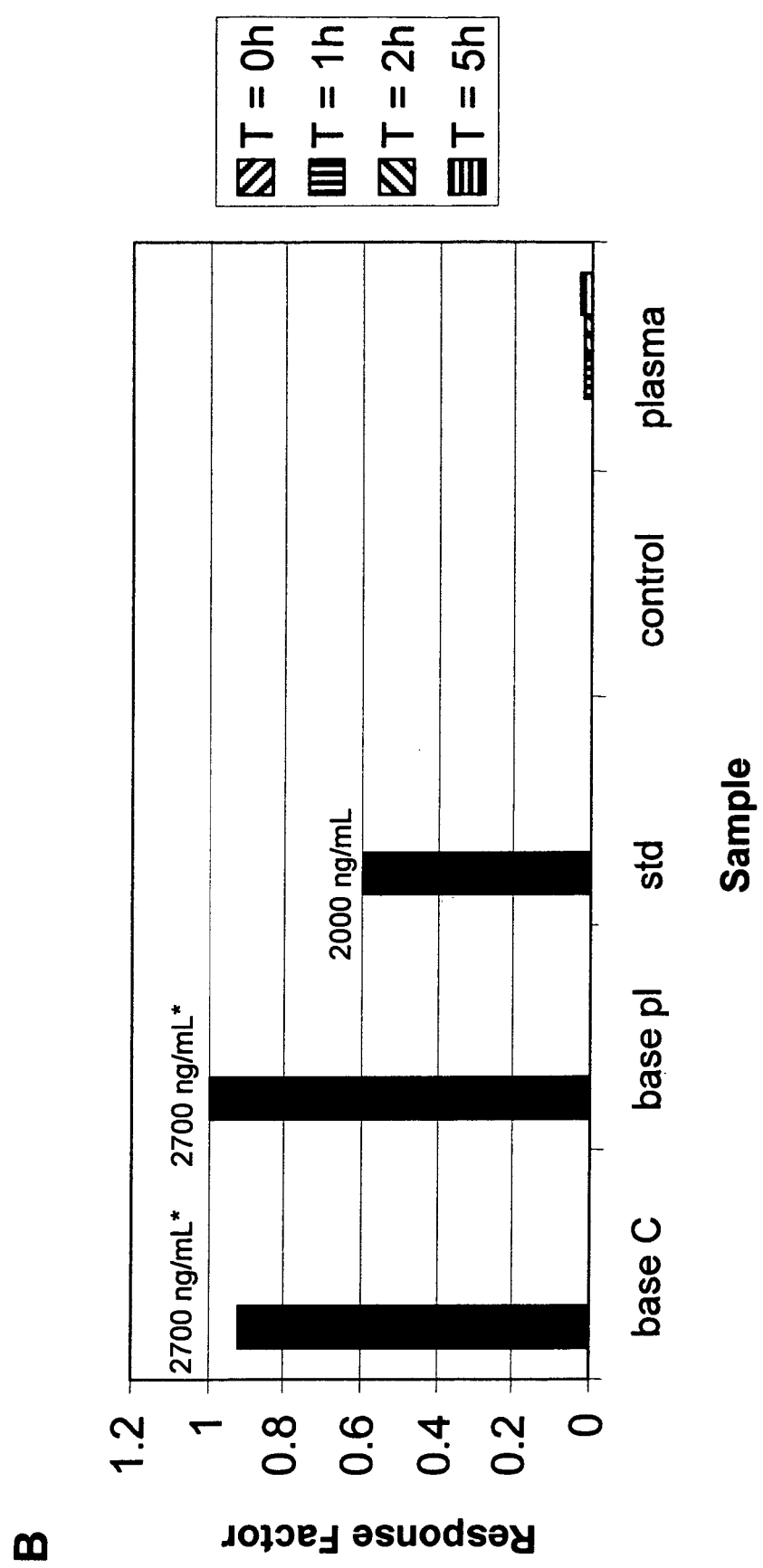
Figure 2:
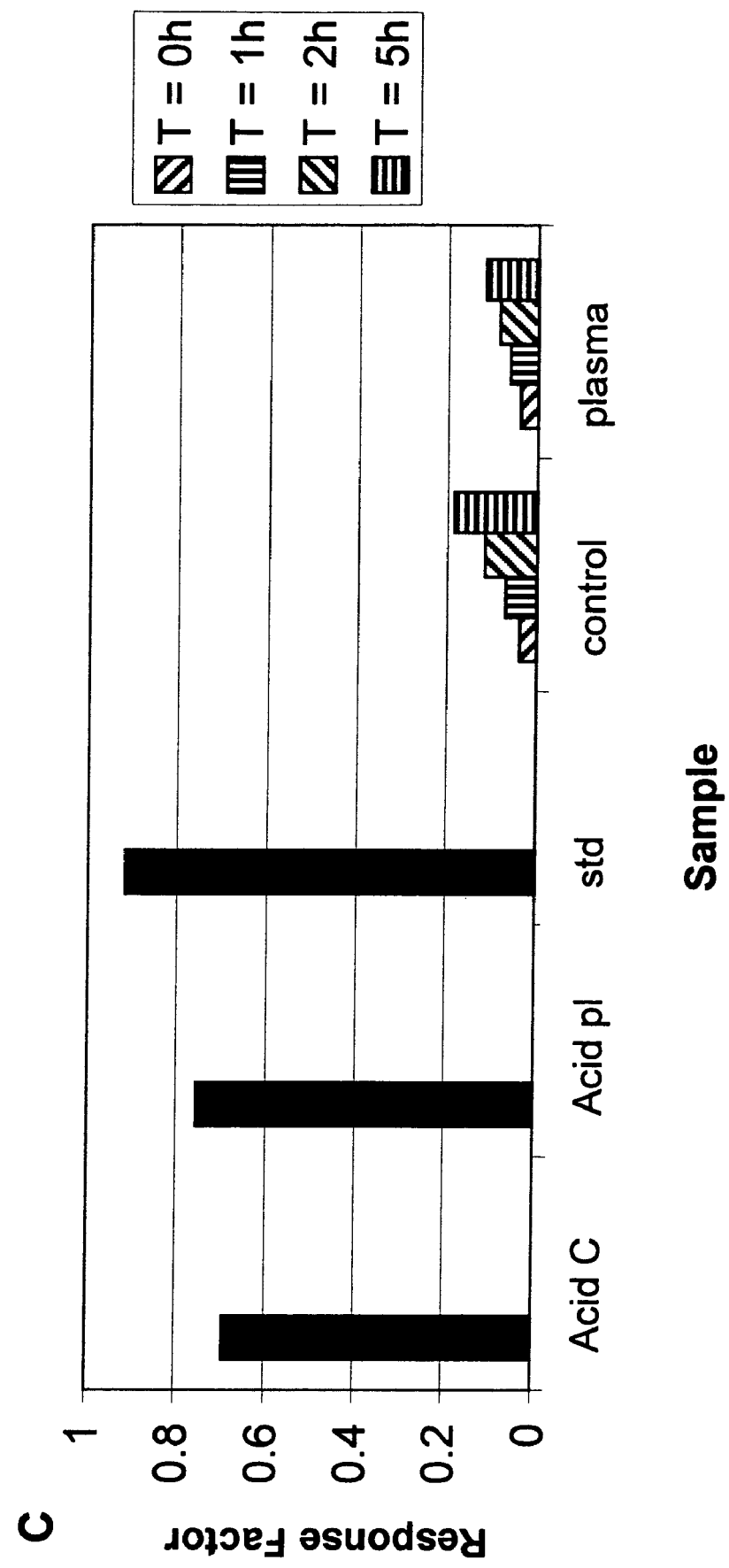
Figure 2:
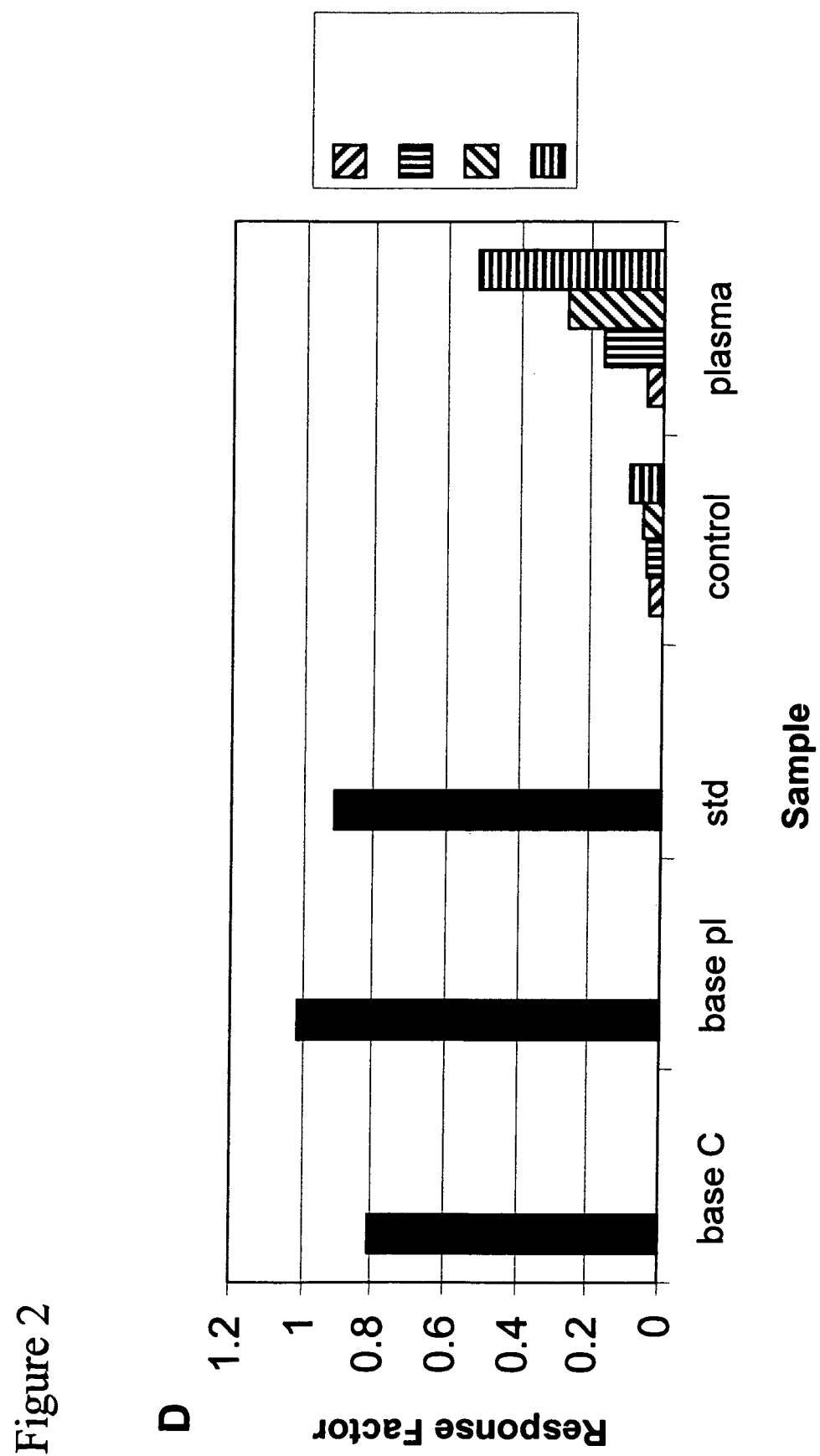

This invention relates to the effective solubilization and transport of polymer-modified carbonyl-containing or quinone-containing therapeutic agents and their use in the treatment of diseases, including cancers, by water-soluble carboxyl-containing polymers. Another aspect of the invention regards the effective solubilization and transport of polymer-modified anti-cancer agents, such as β-lapachone compounds, to tumor cells or tumor tissues so as to promote therapeutic effectiveness.

High molecular weight substances, fine particles, fats and oils are more easily accumulated and stay for a longer time in tumor sites and inflammatory sites than in normal tissues. As such, long-circulated macromolecules, including polypeptide/polymer conjugates, are capable of spontaneous accumulation in solid tumors. This accumulation may result from an effect termed the enhanced permeability and retention (EPR) effect. Delivery of anti-cancer agents to tumor cells or tumor tissues in polymer modified forms may advantageously exploit the EPR effect in tumor tissues.

Without intending to be limited by theory, the EPR effect is based on the fact that tumor vasculature, unlike the vasculature of normal tissues, is permeable to macromolecules with a relatively high molecular weight. Structurally, tumor vessels show increased vascular density caused by angiogenesis, impaired lymphatic recovery, and lack of a smooth muscle layer in solid tumor vessels. More importantly, functional augmentation of this enhanced vascular permeability in tumor tissues has been recognized and includes extensive production of vascular mediators such as bradykinin, nitric oxide, prostaglandins, matrix metalloprotinases, and vascular endothelial growth factor/vascular permeability factor, among others. High permeability of the vasculature allows macromolecules to enter the tumor interstitial space, while compromised lymphatic filtration allows them to stay there. Unlike macromolecules, low-molecular-weight pharmaceuticals are generally not retained in tumors because of their ability to return to the circulation by diffusion. Thus, the conjugation of low molecular weight molecules with molecular weight increasing compounds yields complexes that may spontaneously accumulate in solid tumors.

The linking agents and polymer vehicles employed to prepare the polymer conjugates described herein advantageously permit the selection of delivery conditions for carbonyl-containing and quinone-containing therapeutic agents having a broad range of solubilities and potencies through the choice of linking chemistry (e.g., imine, quinol-ester, or ketal), the specific linking agents, and the polymeric vehicle employed. Where the therapeutic agents are of high potency, the present invention advantageously permits delivery over short or long time intervals, depending upon the selection of the specific linking agent and polymeric vehicle. At the other end of the potency spectrum, the linking chemistries of the present invention advantageously permit the delivery of lower potency therapeutic agents over short time intervals, thereby permitting a pharmacologically active amount of the unconjugated therapeutic agent to be delivered. In preferred embodiments, a low potency therapeutic agent may be maintained at a pharmacologically active level, as measured in either in the plasma or at a site of action such as a tumor, for a time period longer than that which can be achieved by delivery of a bolus of the free therapeutic agent (i.e., therapeutic agent which is not in a polymer conjugate or prodrug form). In some embodiments, greater than 50% of a therapeutic agent present in a polymer conjugate may be released from the polymer conjugate in 24 hours. In other embodiments, greater than 70% of a therapeutic agent may be released from a polymer conjugate in 24 hours, and in other embodiments, greater than 90% of a therapeutic agent may be released from a polymer conjugate in 24 hours. In addition, the relatively high loading of therapeutic agents into the polymer conjugates of the invention permits delivery of large amounts of the therapeutic agents while minimizing the amount, and thus the potential impact, of the polymeric vehicle required to effectuate the delivery of the therapeutic.

Figure 3:
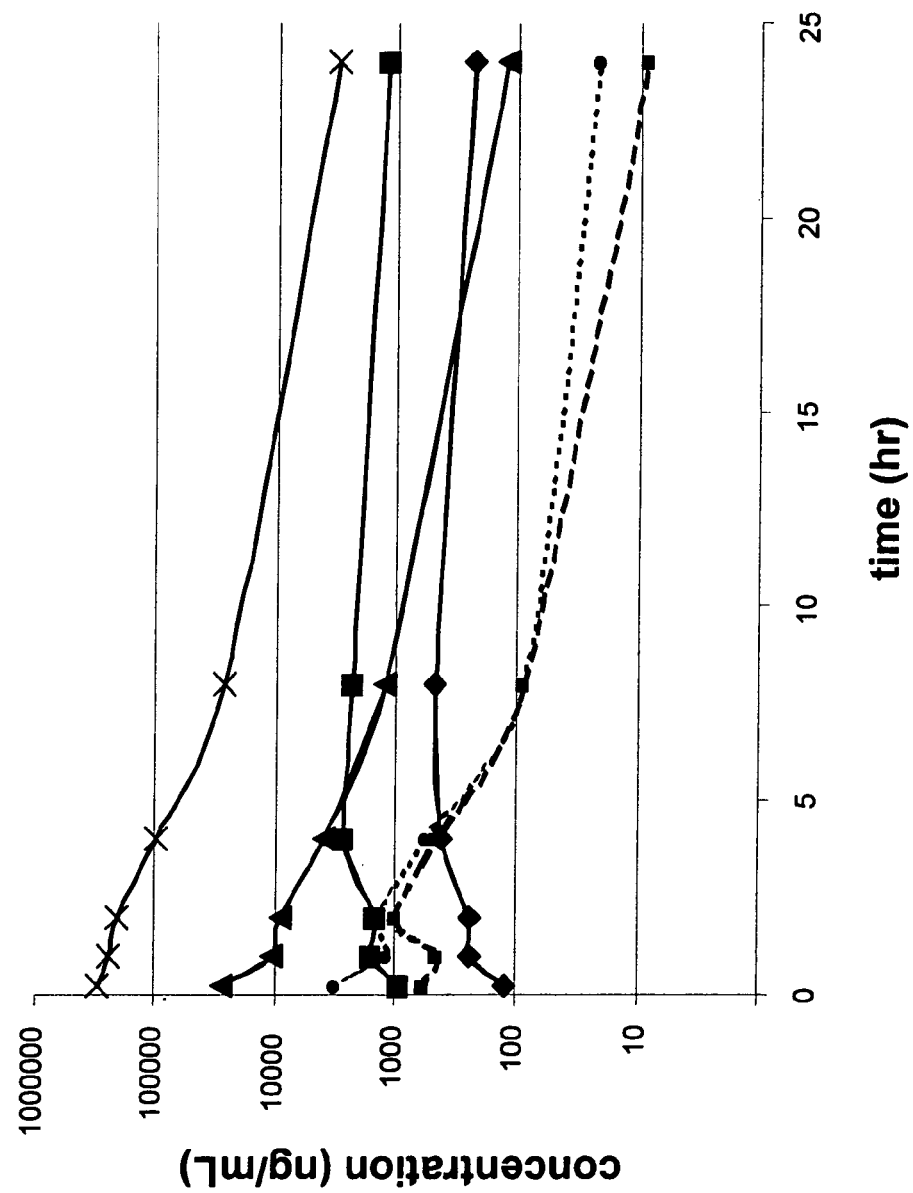
FIG. 3 sets forth a time course of tumor and plasma levels (concentration given in ng/ml) of β-lapachone following administration of: β-lapachone (reference) by intraperitoneal administration (ip) (60 mg/kg) or 5-(acetyloxy)-2,2-dimethyl-3,4-dihydro-2H-benzo[h]chromen-6-yl glycinate γ-poly-L-glutamate (Table 1: Sample B) by intravenous (iv) administration (26 mg/kg equivalents of β-lapachone, 139 mg/kg of the polymer conjugate having 19.3% β-lapachone by weight) to Ncr NU/NU tumor bearing mice. Free β-lapachone (♦) in tumors; total β-lapachone (■) in tumors; free β-lapachone in plasma (▲); total β-lapachone in plasma (X); β-lapachone reference tumor (--■--); and β-lapachone reference plasma (•••●•••). Experimental details are set forth in Examples 13 and 15.
Figure 5A:
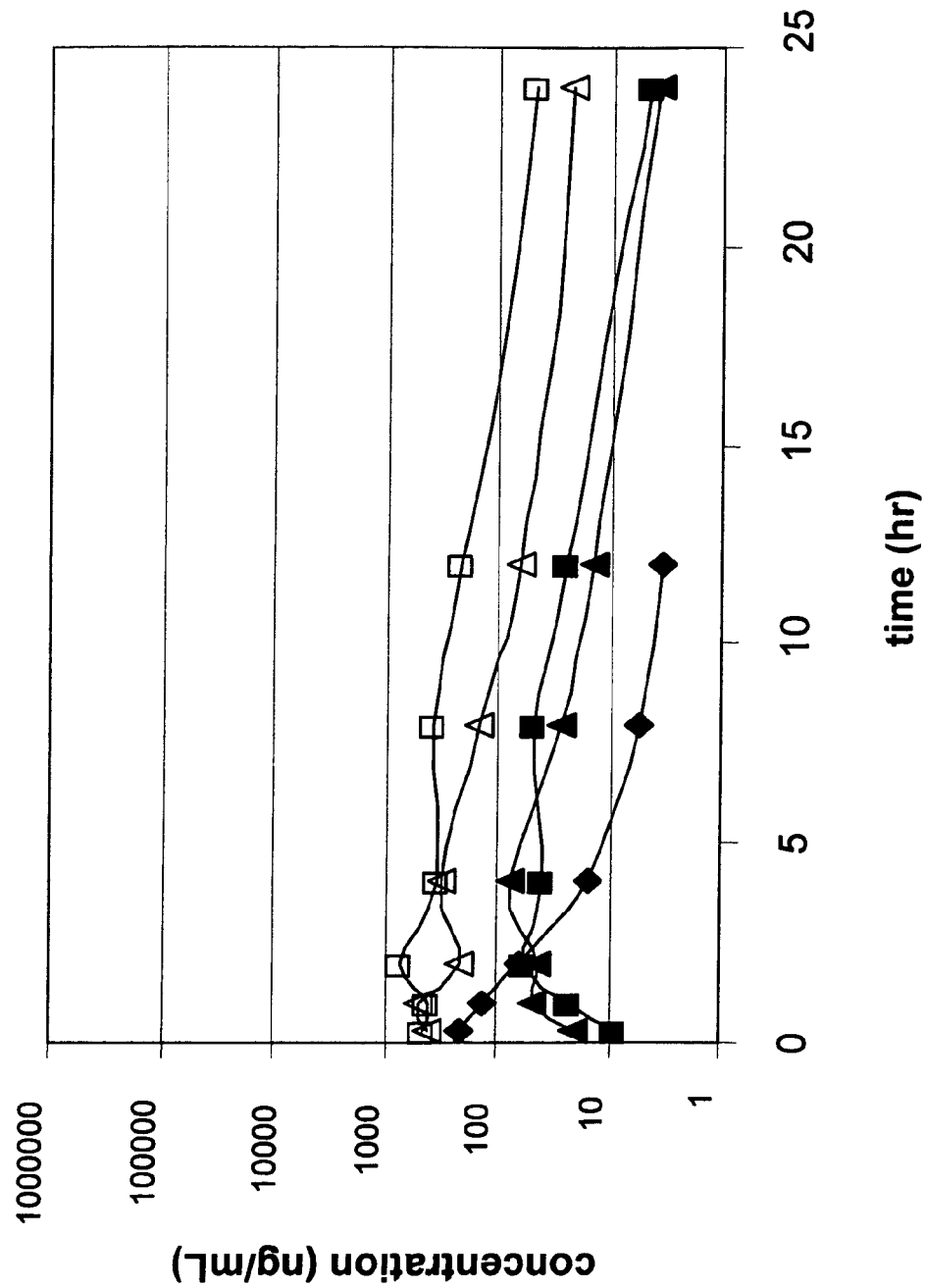
FIGS. 5A & 5B set forth time courses of tumor (A) and plasma (B) levels (concentration given in ng/ml) of β-lapachone following administration of: β-lapachone (reference) by intraperitoneal administration (ip) (60 mg/kg), 5-(acetyloxy)-2,2-dimethyl-3,4-dihydro-2H-benzo[h]chromen-6-yl glycinate γ-poly-L-glutamate (Table 1: Sample B) by intravenous (iv) administration (14 mg/kg equivalents of β-lapachone, 73 mg/kg of the polymer conjugate having 19.3% β-lapachone by weight) or 5-(acetyloxy)-2,2-dimethyl-3,4-dihydro-2H-benzo[h]chromen-6-yl glycinate γ-poly-L-glutamate (Table 1: Sample D) by intravenous (iv) administration (14 mg/kg equivalents of β-lapachone, 75 mg/kg of the polymer conjugate having 18.6% β-lapachone by weight) to Ncr NU/NU tumor bearing mice.

The ability to select conditions suitable for the delivery of therapeutic agents, even those having even low solubility in aqueous solution and low potency, is illustrated by the polymer conjugates of β-lapachone described for example in FIGS. 3, 5A and B. Therapeutic levels of β-lapachone in both tumors and plasma persist for up to about 24 hours following the administration to mice of 5-(acetyloxy)-2,2-dimethyl-3, 4-dihydro-2H-benzo[h]chromen-6-yl glycinate γ-poly-L-glutamate (Table 1: Samples B and D). Thus, 5-(acetyloxy)-2,2-dimethyl-3,4-dihydro-2H-benzo[h]chromen-6-yl glycinate γ-poly-L-glutamate represents a preferred means of delivering β-lapachone because it advantageously increases the solubility, increases the levels achievable and maintainable in both plasma and in tumor tissues, and the duration of action relative to the unconjugated compound. In addition, the administration of polymer conjugates that release therapeutic over a suitable long time period, such as 5-(acetyloxy)-2,2-dimethyl-3,4-dihydro-2H-benzo[h]chromen-6-yl glycinate γ-poly-L-glutamate, permits fewer administrations of the therapeutic agent where the therapeutic is delivered in bolus form. Moreover, the high loading of therapeutic that can be achieved using polymer conjugates such as 5-(acetyloxy)-2, 2-dimethyl-3,4-dihydro-2H-benzo[h]chromen-6-yl glycinate γ-poly-L-glutamate (Table 1: Sample D) advantageously minimizes the amount of excipients that need to be administered to achieve pharmacologically effective administration of therapeutic agents, particularly those having low solubility and low potency such as β-lapachone. For at least these reasons, 5-(acetyloxy)-2,2-dimethyl-3,4-dihydro-2H-benzo[h] chromen-6-yl glycinate γ-poly-L-glutamate represents a preferred means of delivering β-lapachone as a therapeutic agent.

Another aspect of this invention relates to the unexpected stabilization observed for quinone-containing therapeutic agents and carbonyl containing therapeutic agents presented in the polymer-modified forms described herein. This is reflected in the prolonged half-life of the compounds both in vitro at neutral pH and in vivo. Related to the increased stability of quinone-containing therapeutic agents and carbonyl containing therapeutic agents presented in the polymer-modified forms described herein is the higher levels of the drugs that can be both achieved and maintained in a subject or in specific tissues or plasma. The increased levels of therapeutic agents that may be achieved is particularly important for drugs, such as β-lapachone, whose solubility might otherwise limit their value as a therapeutics agents due to the difficulty of maintaining an effective therapeutic level of the drug in the relevant tissues. Maintaining increased levels of such therapeutics in tumors is expected to provide a better treatment profile for cancer patients.

Other aspects of the invention relate to polymer-modified β-lapachone compounds and methods of treating cancer by administering the polymer-modified β-lapachone compounds of the invention to a subject, as described in more detail herein. More specifically, the polymer-modified β-lapachone compounds of the invention generally comprise a β-lapachone or an analog thereof associated with at least one polymeric material by way of one of the linking mechanisms (imine, quinol-ester, or ketal).

Therapeutics may be released from the polymer conjugates of this invention substantially by two means, further described below, both of which involve the cleavage of a linking agent bond. The skilled artisan will recognize that cleavage of the bond between the linking agent and the polymer or therapeutic agent may result in the production of a modified form of the linking agent. One exemplary modification that might occur to a linking agent is one in which the atom of a linker-conjugated therapeutic agent that is initially involved in the bond with the polymeric vehicle is attached to a protective group that becomes eliminated in the formation of the polymer conjugate. Upon cleavage from the polymer vehicle, another substituent, such as a hydrogen or hydroxyl group from hydrolysis, would replace the protective group.

The first means of therapeutic agent release from the polymer conjugates of the invention occurs where the bond between the polymeric vehicle and the linker is cleaved to release a linker-conjugated therapeutic agent, which like the polymer conjugate, may be considered a prodrug. Where the linking agent has become modified by the cleavage of the bond between the polymeric vehicle and the linker, the linker-conjugated therapeutic agent released from the polymeric vehicle may be a modified form of the linker-conjugated therapeutic agent that was used to prepare the polymer conjugate. Subsequent release of the therapeutic agent from the linking agent or a modified form of the linking agent, may involve not only the cleavage of the therapeutic agent from the linking agent, but also other enzymatic and non-enzymatic steps. Thus, for example, a quinone-containing therapeutic agent, such as β-lapachone, may be released from the polymeric vehicle of a quinol-ester polymer conjugate by cleavage of the bond between the polymeric vehicle and the quinol-ester linker conjugated therapeutic agent. Subsequent release of a therapeutic agent, such as β-lapachone, from the linking agent may not only involve the enzymatic or non-enzymatic cleavage of the linking agent from the quinol-ester, but also other enzymatic or non-enzymatic processes. These processes may include, but are not limited to, cleavage, such as a cleavage of a carboxylic acid bound to a hydroxyl of a quinol-ester (e.g., $R_2COOH$ of quinol-ester conjugates) and the oxidation of the quinol form of a therapeutic, such as β-lapachone, to its quinone form.

The second means of therapeutic agent release from the polymer conjugates of the invention involves the cleavage of the linkage between the linking agent and the therapeutic agent without, or prior to, the cleavage of the bond between the linking agent and the polymer vehicle. As with the first means of therapeutic agent delivery from the polymer conjugates of the invention, release of the therapeutic agent by the second means may also involve enzymatic or non-enzymatic processes that occur subsequent to the cleavage of the linkage between the linking agent and the therapeutic agent. Those enzymatic or non-enzymatic processes similarly may include, but are not limited to, cleavage of the carboxylic acid bound to a hydroxyl of a quinol-ester and the oxidation of the quinol form of a therapeutic to the quinone form, such as may occur where the therapeutic agent is β-lapachone. Where such enzymatic or non-enzymatic processes occur subsequent to the cleavage of the linkage between the linking agent and the therapeutic agent, the therapeutic agent can be considered to be released as a prodrug.

A skilled artisan will also recognize that therapeutic agents present in polymer conjugates may be subject to enzymatic or non-enzymatic processes prior to, or concurrent with, their release from polymer conjugates. Where the enzymatic or non-enzymatic processes modify polymer conjugates prior to the release of therapeutic agents from the polymer vehicle, the therapeutic agent may still be released in a prodrug form if the bond between the polymeric vehicle and the linker is cleaved to release a linker-conjugated therapeutic agent. In contrast, whether or not a therapeutic agent is released in a prodrug form where the linkage between the linking agent and the therapeutic agent is cleaved without, or prior to, the cleavage of the bond between the linking agent and the polymer vehicle, depends upon whether the agent released upon cleavage of the linkage requires conversion by enzymatic or non-enzymatic means to the active therapeutic. Thus, for example, polymer conjugates containing β-lapachone bound in a quinol-ester may undergo cleavage of the carboxylic acid associated with one hydroxyl of the quinol ester of prior to, concurrent with, or subsequent to cleavage of the linkage between β-lapachone and the linker.

Standard synthetic methods and procedures for the preparation of organic molecules and functional group transformations and manipulations including the use of protective groups can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. The following descriptions of synthetic methods are designed to illustrate, but not limit, general procedures for the preparation of compounds of the invention.

A. DEFINITIONS

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Alkyl groups may be denoted by a range, thus, for example, a ($C_1$-$C_6$) alkyl group is an alkyl group having from one to six carbon atoms in the straight or branched alkyl backbone. For example, substituted and unsubstituted alkyl groups may independently be $(C_1-C_5)$ alkyl, $(C_1-C_6)$ alkyl, $(C_1-C_{10})$ alkyl, $(C_3-C_{10})$ alkyl, or $(C_5-C_{10})$ alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., $(C_3-C_6)$ cycloalkyl) is a ring structure having between 3 and 6 carbon atoms in the ring. When no range is given, then cycloalkyl has between three and nine carbon atoms ($(C_3-C_9)$ cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from four to nine carbon atoms in the ring structure.

The term "aryl" refers to an aromatic carbocyclic group, having one, two, or three aromatic rings. Exemplary aryl groups include, without limitation, phenyl, naphthyl, and the like. Aryl groups may be fused to form one or more additional nonaromatic carbocyclic or hetercyclic rings having from 4-9 members. Examples of fused aryl groups include benzocyclobutanyl, indanyl, tetrahydronapthylenyl, 1,2,3,4-tetrahydrophenanthrenyl, tetrahydroanthracenyl, 1,4-dihydro-1,4-methanonaphthalenyl, and benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of heteroatom in the aromatic ring are denoted by the type of heteroatom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazyl, quinolyl, quinazolinyl, thiazolyl, benzo[b]thiophenyl, furanyl, imidazolyl, indolyl, and the like.

The term "carboxyl containing polymer" refers to a polymer containing monomer units having carboxyl groups present as the free acid or as a corresponding salt, or carboxylic acid groups present in an activated form such as an orthonitrophenyl ester or an anhydride. Where the monomers contain carboxylic acids as an anhydride, the anhydride may be formed between two carboxyl groups within the monomer, resulting in a cyclic structure (e.g., maleic anhydride monomer units found in SMA polymers). Carboxyl containing polymers may be derived from a variety of sources and include both naturally occurring and unnatural carboxyl containing polymers. Non-limiting exemplary carboxyl containing polymers include: PEG-dicarboxylic acid, SMA, carboxyl containing polyacrylic acids or polyacrylonitriles, naturally occurring and unnatural carboxyl containing polyamides such as PGA, PAA, protein, such as albumin, including for example human serum albumin, polypeptides, naturally occurring and unnatural carboxyl containing polysaccharides.

The terms "carbonyl" refers to a —C(=O)— functionality of a ketone or aldehyde.

The term "ketal," for the purpose of this disclosure, refers to cyclic acetal and cyclic ketal structures formed by the condensation of a hydrated ketone or aldehyde with a 1,2-diol to form 1,3-dioxolane, unless stated otherwise.

The term "carbonyl-containing therapeutic agent" or "carbonyl-containing compound" refers to therapeutic agents, or more broadly to compounds, containing one or more carbonyl groups.

The term "quinone-containing therapeutic agent" or "quinone-containing compound" refers to a therapeutic agent or more broadly to a compound bearing one or more aromatic dicarbonyl groups derived from a dihydroxy aromatic compound.

The terms "protected hydroxyl" or "protected amine" refer to hydoxyl and amine groups bearing a protective functionality such as Boc or Fmoc. A skilled artisan familiar with standard synthetic methods and procedures for the preparation of organic molecules may appropriately select suitable protective groups for use in synthesis from the relevant scientific literature or from standard reference textbooks in the field such as Greene, T. W.; Wuts, P. G. M., Protective Groups in Organic Synthesis, $3^{rd}$; John Wiley & Sons: New York, 1999.

The term "linking agent" refers to a molecule that is capable of forming both a linkage to a polymeric delivery vehicle and a linkage to a molecule that is to be conjugated to the polymeric delivery vehicle, such as a therapeutic agent.

The term "imine-linking agent" refers to a linking agent that may form an imine bond with a carbonyl-containing or quinone-containing molecule that is to be conjugated to a polymeric delivery vehicle. Imine-linking agents preferably contain an aromatic amine that may form stable Schiff bases with carbonyl-containing or quinone-containing molecules.

The term "linker conjugated therapeutic agent" refers to a molecule that comprises a therapeutic agent that has been covalently bound to a linking agent that is not associated with a polymeric delivery vehicle.

The term "quinol-ester linker conjugated therapeutic agent" refers to a molecule comprising a quinone-containing therapeutic agent in which a first hydroxyl of the quinol form of the therapeutic agent is covalently bound to a linking agent by an ester bond (i.e., a quinol-ester), and the remaining hydroxyl (second hydroxyl) of the quinol is separately esterified with a carboxylic acid, where none of the therapeutic agent, the linker, or the carboxylic acid is associated with a polymeric delivery vehicle.

The term "ketal linker conjugated therapeutic agent" refers to a molecule comprising a quinone-containing therapeutic agent or a carbonyl-containing therapeutic agent that has been covalently bound to a linking agent by formation of a ketal linkage between a 1,2-diol (vicinal diol) of a linker and one carbonyl of a quinone-containing therapeutic agent, or a carbonyl of carbonyl-containing therapeutic agent, where neither the therapeutic agent, nor the linker are associated with a polymer delivery vehicle.

The terms "polymer-modified therapeutic agent" and "polymer conjugate" refer to compositions in which a therapeutic agent is covalently attached to a polymeric vehicle via a linking agent. For the purposes of this application, such compositions are typically formed by reacting a linker conjugated therapeutic agent with a polymeric vehicle under conditions that will result in the formation of a bond between the linker of the linker conjugated therapeutic agent and the polymeric vehicle.

While the term "PGA" refers generally to poly(glutamic acid), unless stated otherwise, for the purposes of this invention the term "PGA" refers to poly-L-glutamic acid), alternatively indicated as poly(L-glutamic acid). Similarly, while the term "PAA" refers generally to poly(aspartic acid), unless stated otherwise, for the purposes of this invention the term "PAA" refers to poly-L-aspartic acid), alternatively indicated as poly(L-aspartic acid).

For the purpose of this invention, where the molecular weight of a polymer is given, it is to be understood that the molecular weight represents the average molecular weight of the subject polymer, unless it is stated otherwise. Where a range of polymer molecular weight is given, an individual molecular weight value within the range represents an average molecular weight of the subject polymer. Where the molecular weight of a "polymer conjugate" is given, the molecular weight represents that of the sodium salt unless stated otherwise.

B. POLYMERIC VEHICLES FOR THE DELIVERY OF POLYMER-MODIFIED QUINONE-CONTAINING OR CARBONYL-CONTAINING THERAPEUTIC AGENTS

1. Suitable Polymeric Vehicles for the Delivery of Carbonyl-Containing and Quinone-Containing Therapeutic Agents.

A variety of polymers are useful as polymeric delivery vehicles for delivering therapeutic agents to tumor cells or tumor tissues. Among these polymers are carboxyl-containing polymers including, but not limited to, poly(styrene-co-maleic anhydride) copolymers (SMA), N-(2-hydroxypropyl)methacrylamide (HPMA) copolymers with carboxyl containing peptides. Other suitable polymeric delivery vehicles include carboxyl-containing polyamides such as polyglutamic and polyaspartic acids, and modified polyethylene glycols (PEG). Association of therapeutic agents with polymers provides for a larger molecule, which may be selectively accumulated in tumor tissues via the EPR effect. Preferred polymers of the invention bearing free carboxylic acid moieties, which are suitable for the attachment of quinone-containing molecules, such as β-lapachone, through the linking groups are described below.

2. SMA and HPMA Polymers:

Particularly suitable polyvinyl polymers for the delivery of carbonyl-containing or quinone-containing therapeutic agents, such as β-lapachone, include those bearing carboxyl moieties that may serve as sites for the conjugation of linkers suitable for attaching the therapeutic agents to polymers. One such type of polyvinyl polymer is poly(styrene-co-maleic anhydride) polymers ("SMA polymers" or "SMA"). A particular advantage of SMA is its ability to non-covalently bond to albumin in vivo, which further aids the observed EPR effect. In addition, the amphiphilic nature of SMA enables a range of formulation possibilities including as an aqueous formulation for parenteral administration (e.g., intravenous, intramuscular, intraperitoneal, and subcutaneous injection).

In certain embodiments, the SMA preferably comprises the following main chain units:

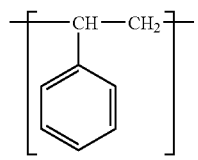

styrene residues

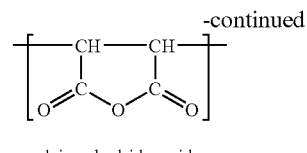

maleic anhydride residues in desired ratios. Desired ratios for styrene to maleic anhydride residues (expressed as moles of styrene residues to moles of maleic anhydride) vary for different molecular weight SMA polymers. For lower molecular weight SMA polymers desired ratios are from about 1.6:1.0 to about 1:1. Other suitable ratios include about 1.4:1 and about 1.3:1. For higher molecular weight SMA polymers the ratio of styrene to maleic anhydride residues increases to about 3:1 at 9,500 Da, and about 4:1 at 11,000 Da. The upper limit of maleic anhydride residues in SMA polymers is generally not greater than 50 mol %, with the upper limit being about 60 mol %. Preferred SMA moieties comprise styrene-co-maleic anhydride units of the form:

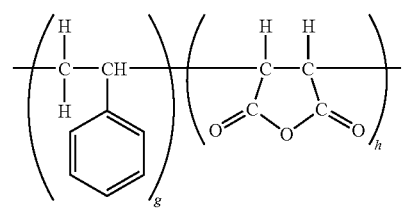

where "g" and "h" represent integer values consistent with those ratios of styrene residues to maleic anhydride residues described above.

In other embodiments, SMA polymers may also contain maleic acid half ester residues of the form

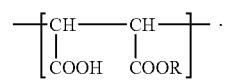

In the above maleic acid half ester residue, R is: (1) a linear lower alkyl residue having 1-5 carbon atoms, such as methyl, ethyl, propyl, butyl, pentyl, etc., preferably normal alkyl groups, more particularly n-butyl; (2) a monohydroxy-alkyl ether residue of di- or trihydric alcohols, for example: alkylene glycol mono-lower alkyl ether residue, wherein the alkylene group is ethylene or butylene and the lower alkyl group has 1-4 carbon atoms and is preferably ethyl or n-butyl, more particularly n-butyl; (3) a polyethyleneglycol mono-alkyl ether residue represented by the formula —$(C_2H_4O)_k$—R' wherein R' is a linear alkyl group having 1-8 carbon atoms, and "k" is from 2 to 20; or (4) a glycerin dialkyl ether residue, wherein the alkyl groups have 1-4 carbon atoms. The term "half ester" used herein means that one of the two carboxyl groups of maleic acid formed by opening the ring of maleic anhydride has been esterified. It is preferable that substantially all maleic acid residues, other than maleic anhydride residues, are half esterified but a part thereof may be free maleic acid residues.

SMA polymers useful for forming conjugates may have an average molecular weight of about 1,000-20,000 Da, as determined by gel permeation chromatography. Other suitable molecular weight ranges for SMA polymers include from about 1,000 to about 5,000 Da, or from 1,100 to about 4,000 Da or from about 1,200 to about 3,000 Da or from about 1,300 to about 2,000 Da. Additionally, SMA polymers useful for forming conjugates may have an average molecular weight from about 8,000 Da to about 17,000 Da or from about 10,000 Da to about 15,000 Da or from about 11,000 to about 13,000 Da. Particularly useful SMA polymers for forming conjugates may have an average molecular weight of about 1,200 Da, about 1,600 Da or about 12,000 Da. All molecular weights recited are average molecular weights of the polymers prior to their conjugation with carbonyl-containing or quinone-containing therapeutics agents unless stated otherwise. SMA polymers may be prepared by methods known in the art, including half-esterifying styrene-maleic anhydride copolymers with mono-alcohols, or may be purchased from a variety of sources including Sartomer (Exton, Pa.) and Sigma-Aldrich (St. Louis, Mo.).

3. N-(2-hydroxypropyl)methacrylamide Copolymers (HPMA Copolymers)

In addition to those polymers already discussed, polymers of N-(2-hydroxypropyl)methacrylamide may also be employed in the preparation of polymer-modified carbonyl-containing or quinone-containing therapeutic agents. Suitable HPMA copolymers include those bearing carboxyl groups, protected carboxyl groups or activated carboxyl groups that are capable of reacting with the hydroxyl or amine functionalities of linkers of formulas I, II or III. In a preferred embodiment, the HPMA copolymers are copolymers of N-(2-hydroxypropyl)methacrylamide and N-methacryloylamino acids, or N-methacryloylpeptides (particularly those peptides where the N-methacryloyl group is on the N-terminal amine). Free carboxyl groups of both N-methacryloylamino acids, or N-methacryloylpeptides are protected as required for the polymerization with N-(2-hydroxypropyl) methacrylamide to form the desired HPMA copolymers. A variety of readily hydrolyzible protecting groups may be employed to protect the terminal carboxyl group of N-methacryloylamino acids or N-methacryloylpeptides such as methyl, ethyl, or benzyl esters, particularly preferred are aryl esters such as 4-nitrophenyl esters groups. Protecting groups such as 4-nitrophenyl esters are particularly advantageous as they may be directly reacted with the amine or hydroxyl functionalities present in the linkers of linker conjugated therapeutic agents described below to form polymer-modified carbonyl-containing or quinone-containing therapeutic agents having an ester or amide bond to the peptide or amino acid and of the HPMA copolymer. Reaction of nitrophenyl esters with linker conjugated therapeutic agents to form amide or ester linkages may be conducted in polar aprotic solvents such as DMF, DMSO or acetonitrile at elevated temperatures. Alternatively, N-methacryloylamino acids, or N-methacryloylpeptides bearing carboxyl protecting groups, including 4-nitrophenyl esters, may be deprotected to yield the corresponding free acids, which may be coupled to amine or hydroxyl groups present in the linkers of linker conjugated therapeutic agents in using suitable dehydrating agents such as dicyclohexylcarbodiimide (DCC).

The preparation of monomers for preparing HPMA copolymers may be conducted by methods known in the art. More specifically, N-(2-hydroxypropyl)methacrylamide may be prepared by methods such as those described by Ulbirch, K., et al. in J. Controlled Release, 64: 63 (2000) and N-methacryloylamino acids, or N-methacryloylpeptides may also be prepared by Schotten-Baumann reactions employing N-methacryloyl chloride in aqueous alkaline medium as described by Etrych et al. in *Synthesis of HPMA Copolymer Containing Doxorubicin Bound via a Hydrazone Linkage. Effect of Spacer on Drug Release and in vitro Cytotoxicity, Macromolecular Bioscience* 2: 43-52 (2002). Any suitably protected N-methacryloylamino acid or N-methacryloylpeptide may be employed in the preparation of HPMA copolymers. The synthesis of other N-methacryloyl 4-nitrophenyl peptide esters suitable as monomers for the preparation of HPMA copolymers are described in WO 03/053473. Such peptides include GlyPheGly, GlyPheLeuGly, and GlyLeuPheGly. Some suitable N-methacryloylamino acid, and N-methacryloylpeptide 4-nitrophenyl esters include: N-methacryloylglycine 4-nitrophenyl ester, N-methacryloylalanine 4-nitrophenyl ester, N-methacryloyl-β-alanine, 6-(2-methyl-acryloylamino)-hexanoic acid 4-nitro-phenyl ester (i.e., N-methacryloyl(6-aminohexanoic acid) 4-nitrophenyl ester), 4-(2-methyl-acryloylamino)-benzoic acid, N-methacryloylglycylglycine 4-nitrophenyl ester, N-methacryloylglycyl-L-leucylglycine 4-nitrophenyl ester, N-methacryloylglycyl-DL-phenylalanyl-L-leucylglycine 4-nitrophenyl ester.

Random copolymers of N-(2-hydroxypropyl)methacrylamide with one or more N-methacryloylamino acids, or one or more N-methacryloylpeptides (e.g., 4-nitrophenyl esters of N-methacryloylamino acids, or N-methacryloylpeptides) may be prepared by methods described in the art such as those in Etrych et al in *Synthesis of HPMA Copolymer Containing Doxorubicin Bound via a Hydrazone Linkage. Effect of Spacer on Drug Release and in vitro Cytotoxicity, Macromolecular Bioscience* 2: 43-52 (2002). The reaction is typically conducted by free radical precipitation polymerization in acetone using AIBN (0.4-0.7% based upon the weight of monomers employed) as a free radical catalyst. Typical ranges for N-(2-hydroxypropyl)methacrylamide monomers to N-methacryloylamino acid, or one or more N-methacryloylpeptide monomers are from about 25:1 to about 10:1. The reactions are typically carried out at 50° C. for 24 hours. Polymers suitable for the formation of conjugates typically contain from about 30 monomers (about 4,000 Da) to about 3,000 (about 400,000 Da), where the estimated molecular weights are based upon the calculated molecular weight of N-(2-hydroxypropyl)methacrylamide and will be larger based upon the amino acids or peptides used in the copolymerization.

4. Polyamides

Polyamides suitable for the delivery of carbonyl-containing or quinone-containing therapeutic agents, such as β-lapachone, include those bearing free carboxyl functionalities that may serve as sites for the conjugation of linkers suitable for attaching the therapeutic agents to the polymers via the quinone functionality. Preferred polyamides include, but are not limited to PGA polymers (poly(L-glutamic acid), poly(D-glutamic acid), and poly(DL-glutamic acid)), PAA polymers (poly(L-aspartic acid), poly(D-aspartic acid), and poly(DL-aspartic acid)), and copolymers comprising one or more isomer of aspartic acid with one or more isomer of glutamic acid. More preferred polyamide polymers include poly(L-aspartic acid) and poly(L-glutamic acid). Most preferred is poly (L-glutamic acid). Unless stated otherwise, PGA and PAA are understood to refer to (poly(L-glutamic acid) and (poly(L-aspartic acid) respectively.

Polyglutamic acid (PGA) sodium salt and the free acid have the form:

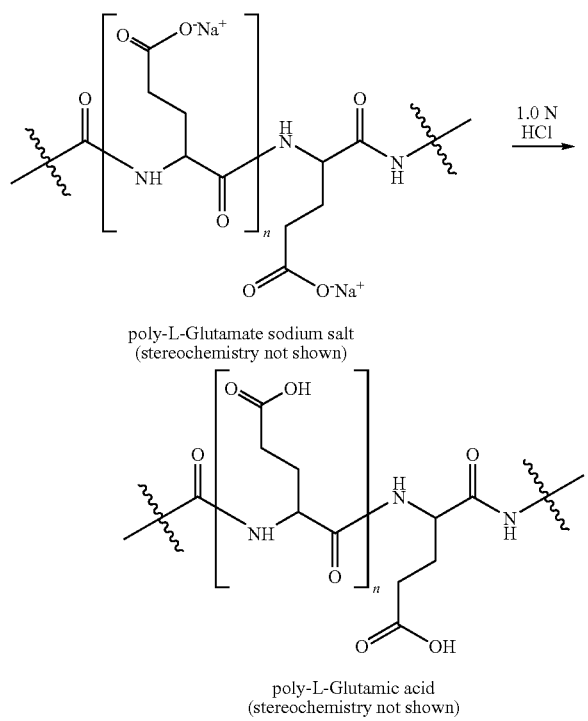

poly-L-Glutamate sodium salt
(stereochemistry not shown)

poly-L-Glutamic acid
(stereochemistry not shown)

where "n" represents an integer value consistent with the molecular weight range of polyglutamic acid polymers suitable for the preparation of polymer conjugates.

The polyglutamic acids and polyaspartic acids for the preparation of conjugates of the invention may have an average molecular weight of about 5,000 Da to about 100,000 Da, or from about 7,000 Da to about 80,000 Da, or from about 10,000 Da to about 70,000 Da. Other suitable molecular weight ranges for polyglutamic acids and polyaspartic acids are from about 12,000 Da to about 28,000 Da or from about 15,000 Da to about 24,000 Da, or from about 20,000 to about 80,000 Da, or from about 30,000 to about 70,000 Da, or from about 45,000 to about 60,000 Da. Particularly useful polyglutamic acids and polyaspartic acids for forming conjugates may have an average molecular weight of about 17,000 Da, or an average molecular weight of about 22,000 Da, or an average molecular weight of about 56,000 Da may also be employed. All molecular weights given are average molecular weights of the sodium salt of the polymers prior to their conjugation with carbonyl-containing or quinone-containing therapeutics agents unless stated otherwise. Polyglutamic acid and polyaspartic acid molecular weights may be determined by multi-angle laser light scattering (MALLS), viscosity, and/or gel permeation chromatography.

Polyglutamic and polyaspartic acid polymers, including copolymers, may be made by methods known in the art including the condensation of monomers in the presence of suitable catalysts (e.g., acids or bases) or dehydrating agents, such as N,N'-dicyclohexylcarbodiimide. Alternatively, polyaspartic acid and polyglutamic acid are available from commercial sources (e.g., Sigma-Aldrich, St. Louis, Mo.).

3. Polyethylene Glycols

Polyethylene glycols (H[OCH$_2$CH$_2$]$_d$OH, where d represents the number of repeating units found in the PEG molecule) suitable for the delivery of carbonyl-containing or quinone-containing therapeutic agents, such as β-lapachone, include those modified to bear free carboxyl functionalities that may serve as sites for attachment of linker conjugated therapeutic agents via the linker moiety. Polyethylene glycols having different average molecular weights are available from a variety of different suppliers, including Sigma-Aldrich (St. Louis, Mo.) For the purpose of preparing polymer-modified carbonyl-containing or quinone-containing therapeutic agents, PEG having a molecular weight range of about 20,000 to about 60,000 Da is preferred, although other molecular weight ranges may be employed, including from about 1,000 to about 10,000 Da, about 10,000 Da to about 20,000 Da, and about 60,000 to about 80,000 Da.

Modification of PEG molecules to incorporate moieties bearing free carboxyl functionalities may be accomplished by a variety of means, including the reaction of PEG with halogenated-carboxylic acids in the presence of a base. For the purpose of preparing the PEG derivative the carboxyl group is generally protected as an ester (e.g., methyl, ethyl etc.) that may later be cleaved under suitable conditions. One suitable group of halogenated-carboxylic acid esters that may be employed is halogenated aliphatic carboxylic acid esters. Preferably, the halogenated aliphatic acid esters are β-halogenated aliphatic carboxylic acid or ω-halogenated alkyl carboxylic acid of the form halogen-(CH$_2$)$_c$C(=O)—O-protecting group, where "c" is an integer from 1-12, which upon reaction with PEG and deprotection give rise to a PEG-dicarboxylic acid of the form: HOOC(CH$_2$)$_c$O[OCH$_2$CH$_2$]$_d$O (CH$_2$)$_c$COOH, where "d" is an integer value consistent with molecular weight of PEG that may be employed to form polymer conjugates. PEG-dicarboxylic acid may be represented as HOOC—CH$_2$—O-PEG-O—CH$_2$—COOH, which is shown for the di-acetic acid. The average molecular weight of the PEG molecule may be give by a subscript to the PEG repeating unit (e.g., HOOC—CH$_2$—O-PEG$_{40kDa}$-O—CH$_2$—COOH. for a 40,000 Da PEG). A particularly useful halogenated aliphatic carboxylic acid ester for preparing the above-described dicarboxylic acid forms of PEG is ethyl bromoacetate.

Reaction of PEG with esters of halogenated carboxylic acids may be conducted by procedures described in the art, such as those described by Greenwald R. B. et al., Drug Delivery Systems: Water Soluble Taxol 2'-Poly(ethylene glycol) Ester Prodrugs-Design and in Vivo Effectiveness, J. Med. Chem. 39: 424-31 (1996); Veronese M. et al., Physico-Chemical and Pharmacokinetic Characterization of Monethoxy Poly(Ethylene Glycol)-Derivatized Superoxide Dismutase, J. Controlled Release, 10, 145-54 (1989); or Gebhardt, H. et al. Soluble Polymers in Organic Chemistry 5. Preparation of Carboxyl- and Amino-Terminal Polyethylene Glycols of Lower Molecular Weight, Polymer Bull. 18: 487-93 (1987). Generally, the reactions of PEG with esters of halogenated carboxylic acids are conducted in the presence of a suitable base (e.g., K$^+$tert-butoxide$^-$). The carboxyl groups are then de-esterified in aqueous NaOH, and the free acid recovered after acidification with a suitable acid (e.g., aqueous HCl).

C. CARBONYL AND QUINONE CONTAINING THERAPEUTIC AGENTS

The compositions and methods of delivering therapeutic agents described herein are generally applicable to therapeutic agents bearing carbonyl or quinone functionalities. Exemplary carbonyl and quinone-containing therapeutic agents include, but are not limited to, lobeline, acebutolol, methyprylon, haloperidol, molindone, naloxone, oxycodone, methadone, ketanserin, tolmetin, ketoprofen, nabumetone, canrenone, canrenonate, mebendazole, oxolinic acid, tetracycline, chlortetracycline, oxytetracycline, demeclocycline, doxycycline, minocycline, daunorubicin, doxorubicin, mitoxantrone, plicamycin, mitomycin, indan-1,3-dione, anisindione, testosterone (and related C-17 esters, e.g., propionate, enanthate, cypionate), dihydrotesterone, cyproterone acetate, estrone, progesterone, medroxyprogesterone acetate, hydroxyprogesterone caproate, norethindrone, norethynodrel, megestrol acetate, norgestrel, mifepristone, methandrostenolone, oxandrolone, testolactone, cyproterone acetate, prednisone, prednisolone, betamethasone, dexamethasone, other 3-, 17-, or 20-ketosteroids (e.g., dehydroepiandorsterone, androstenedione, cortisol, cortisone, aldosterone, etc.), and in a preferred embodiment, β-lapachone compounds. Where the carbonyl groups of a quinone-containing therapeutic agent are not equivalent, both of the individual regioisomers, and mixtures of both regioisomers, that may be formed by attachment of the linking agent to the non-equivalent carbonyls of the quinone, are considered within the scope of this invention. Similarly, polymer-modified forms of each of the individual regioisomers that may be formed from asymetric quinones, and mixtures containing polymer-modified forms of both regioisomers are considered within the scope of this invention.

The β-lapachone compounds of the invention include β-lapachone and analogs thereof. As discussed above, β-lapachone has the following chemical structure:

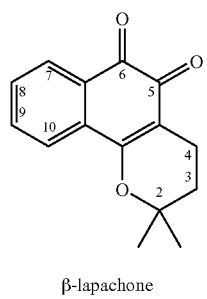

β-lapachone

β-lapachone analogs include compounds that are structural derivatives of β-lapachone, differing from β-lapachone by substitution of one, two, three, four, or more elements of β-lapachone with a different group or element. For example, a hydrogen at the 3 or 4 position may be substituted with a hydroxy or a $C_1$-$C_4$ alkyl, wherein the $C_1$-$C_4$ alkyl is optionally substituted with a hydroxy. Preferred substituents include 3-hydroxy and 3-methanolyl. Further, each of the methyl groups at position 2 may be independently substituted with a hydrogen. The β-lapachone analogs of the invention may also include substitutions of heteroatoms, for instance, the oxygen at position 1 may be substituted with a sulfur atom, and the carbon at position 4 may be substituted with oxygen.

Any β-lapachone analog known in the art may be used as the β-lapachone compound of the invention. For instance, a number of β-lapachone analogs having anti-proliferative properties have been disclosed in the art, such as those described in PCT International Application PCT/US93/07878 (WO 94/04145), and U.S. Pat. No. 6,245,807, in which a variety of substituents may be attached at positions 3- and 4- on the β-lapachone compound. PCT International Application PCT/US00/10169 (WO 00/61142), discloses β-lapachone, which may have a variety of substituents at the 3-position as well as in place of the methyl groups attached at the 2-position. U.S. Pat. Nos. 5,763,625, 5,824,700, and 5,969,163, disclose analogs with a variety of substituents at the 2-, 3- and 4-positions. Furthermore, a number of journals report β-lapachone analogs with substituents at one or more of the following positions: 2-, 3-, 8- and/or 9-positions. See, e.g., Sabba et al., (1984) *Journal of Medicinal Chemistry* 27:990-994 (substituents at the 2-, 8- and 9-positions); (Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions).

Moreover, structures having sulfur-containing heterorings in the "a" and "P" positions of lapachone have been reported (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2):163-169; and Krapcho A P et al., (1990) *Journal of Medicinal Chemistry* 33(9):2651-2655). More particularly, hetero β-lapachone analogs are disclosed in U.S. Patent Appln. No. 2004/0266857, entitled "NOVEL LAPACHONE COMPOUNDS AND METHODS OF USE THEREOF," which is herein incorporated by reference.

Preferred β-lapachone analogs include those in which the carbonyl groups are the vicinal diones at the 5 and 6 positions of the 3,4-dihydro-2H-benzo[h]chromene-5,6-dione nucleus.

D. POLYMER CONJUGATION

1. Linking Functionalities for Carbonyl-Containing and Quinone-Containing Molecules.

Therapeutic agents containing a quinone or carbonyl functionality may advantageously be conjugated to the above-described carboxyl-containing polymers of this invention by several linking groups including imines (Schiff's bases), quinol-esters, and ketal linkages. Where the therapeutic agent contains a quinone functionality that is employed in the formation of the polymer conjugate, the quinone may be a 1,2-quinone or a 1,4-quinone even though the 1,2-quinones are depicted.

In accordance with the present invention, one embodiment encompasses polymer-modified quinone-containing or carbonyl-containing therapeutic agents conjugated to SMA, polyglutamic acid, or poly aspartic acids by an imine, quinol-ester, or ketal linkage. In one embodiment, the therapeutic agent is β-lapachone and the polymer is SMA or polyglutamic acid.

2. Imine Polymer Conjugates.

Linking agents capable of forming an imine bond between an amine of the linking agent and a carbonyl or quinone functionality of a therapeutic agent may be employed to form conjugates with polymer vehicles. Linking agent amines for the formation of imine bonds are advantageously aromatic amines that form stable Shiff bases. In addition to providing an amine group for formation of an imine linkage to the therapeutic agent, imine-linking agents also provide a second amine for conjugating the linking agent to a carboxyl group on a polymeric vehicle via amide linkage. Linking agents suitable for conjugation of carbonyl-containing or quinone-containing compounds are generally of the form of formula (I):

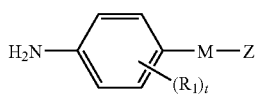

where
  M is a spacer group selected from the group consisting of:
    —(C$_1$-C$_8$) alkyl-, —(CH$_2$)$_q$—O—(CH$_2$)$_r$—,
    —C(=O)—O—(CH$_2$)$_r$—, —(C$_3$-C$_7$)cycloalkyl-,
    -aryl-C(=O)—O—(CH$_2$)$_r$—, —(C=O)—O—aryl-
    (CH$_2$)$_r$—, -heteroaryl-C(=O)—O—(CH$_2$)$_r$—, and
    —C(=O)—O-heteroaryl-(CH$_2$)$_r$—;
  Z is —OH, a protected amine, or a protected hydroxyl;
  each R$_1$ is independently selected from the group consisting of: hydrogen, halogen, and —(C$_1$-C$_4$) alkyl;
  q is from 0-6;
  r is from 2-6; and
  t is from 0-4.

Linking agents of formula I may be prepared by a variety of synthetic routes or purchased commercially. For example: (4-aminophenyl)methanol; 1-(4-aminophenyl)ethanol; 4-(aminomethyl)aniline; 2-(4-aminophenyl)ethanol; 4-(2-aminoethyl)aniline; 2-(diethylamino)ethyl 4-aminobenzoate hydrochloride; 2-(diethylamino)ethyl 4-amino-2-chlorobenzoate hydrochloride; 4-[(5-phenoxypentyl)oxy]aniline are commercially available from Sigma-Aldrich (St. Louis, Mo.).

In a preferred embodiment, where linking agents of formula (I) are of the form

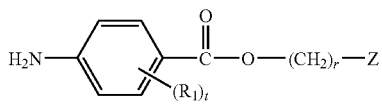

where
  Z is a protected amine;
  each R$_1$ is independently selected from the group consisting of hydrogen, halogen, and —(C$_1$-C$_4$) alkyl;
  r is from 2-6; and
  t is from 0-4;

the linking agents may be prepared by reacting 4-nitrobenzoylchloride with an amine-protected amino alcohol of the form: (protecting group)-NH—(CH$_2$)$_r$—OH, where r is from 2-6. Suitable protecting groups for the amino group include, but are not limited to, 9-fluorenyl-methoxycarbonyl (Fmoc), 2-chloro-1-indanylmethoxy-carbonyl (Climoc), benz[f]indene-3-methyloxycarbonyl (Bimoc), 2,7-di-t-butyl[9-(10,10-dioxo-10,10,-10,10-tetrahydrothioxanthyl)]methyl (DBD-Tmoc), 1,1-dioxobenzo[b]thiophene-2-ylmethyloxycarbonyl (Bsmoc), beta-trimethylsilylethyloxycarbonyl (Teoc), and bis(4'-(nitrophenyl)ethyl carbonyl (Bnpeoc). Fmoc is the preferred protecting group, and preferred Fmoc protected amino alcohols are of the form Fmoc-NH—(CH$_2$)$_r$—OH, where r is from 2-6. The reaction is typically conducted in methylene chloride at room temperature for 1 hour. Following completion, the reaction is washed with water and saturated aqueous solution of sodium chloride. The methylene chloride is dried with Na$_2$SO$_4$, and concentrated to yield the 4-nitro-benzoic acid ester. The nitrogen functionality is subsequently reduced by catalytic hydrogenation in the presence of a noble metal catalyst, such as palladium on charcoal. The reaction is typically conducted at room temperature under 1 atmosphere of nitrogen for 2 hours. Following reduction the catalyst is removed by filtration and the linker of formula (I) is purified by silica gel chromatography as necessary.

In a more preferred embodiment, where t is 0, r is 2, and Z is Fmoc-protected amine, the imine linking agent is 2-{[(9H-fluoren-9-ylmethoxy)carbonyl]amino}ethyl 4-aminobenzoate. Formation of linkers of formula (I) is exemplified by the preparation of 2-{[(9H-fluoren-9-ylmethoxy)carbonyl]amino}ethyl 4-aminobenzoate in Examples 1 and 2, and Scheme 1.

Scheme 1

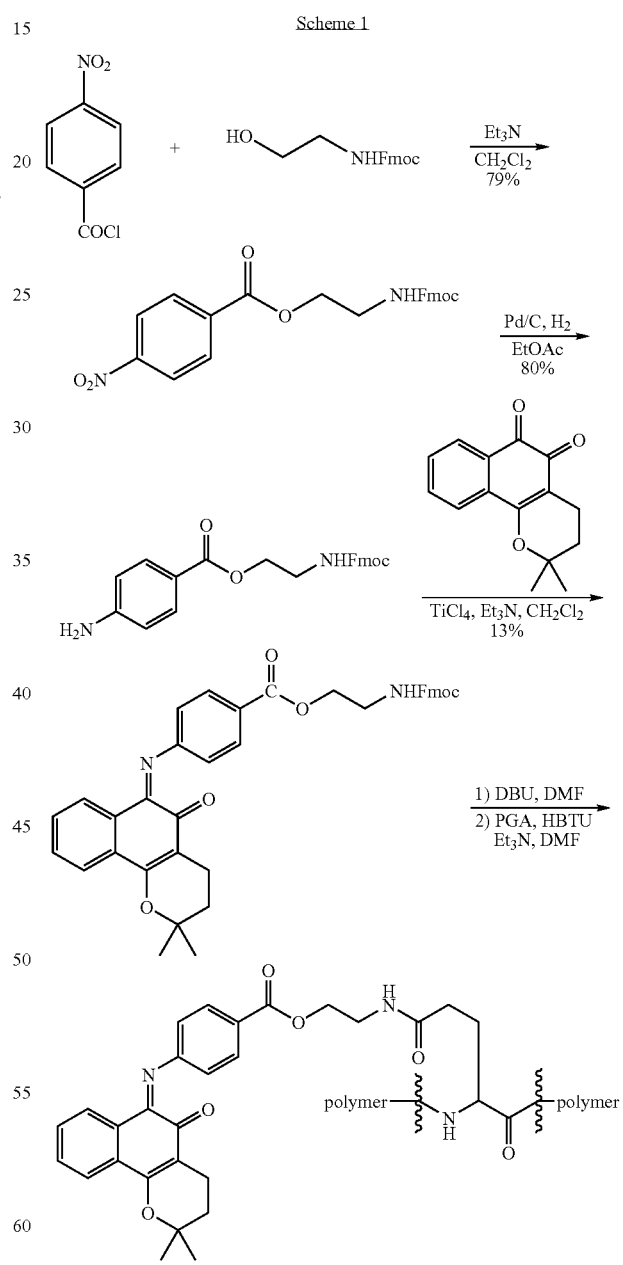

Linkers of formula (I) and carbonyl-containing or quinone-containing therapeutic agents may be conjugated via the aromatic amine of the linker to form a linker conjugated therapeutic agent in a condensation reaction. In the reaction, the aromatic amine of the linking agent and a carbonyl of the therapeutic agents are converted to an imine linkage. The condensation reaction may be conducted in the presence of any suitable agents including, but not limited to, TiCl$_4$, p-toluene sulfonic acid, Si(OEt)$_4$, sulfuric acid, ZnCl$_2$, ZnBr$_2$, and ionic liquids (for example 1-alkyl-2,3-dimethylimidazolium, 1-alkyl-3-methylimidazolium, 1-alkylpyridinium, 1-alkyl-2,3-dimethylimidazolium, 1-alkyl-3-methylimidazolium, 1-alkylpyridinium, 1-alkyl-3-methylimidazolium, 1-alkylpyridinium, 1-alkyl-3-methylimidazolium, 1-alkylpyridinium, 1-alkyl-3-methylimidazolium, 1-alkyl-3-methylimidazolium, 1-alkylpyridinium, 1-alkyl-3-methylimidazolium, 1-alkylpyridinium, and 1-alkyl-2,3-dimethylimidazolium produced by Acros Organics, available through Fisher Scientific International, Hampton N.H., or Fisher Chemicals, Fairlawn, N.J.), The preferred condensing agent is TiCl$_4$. Typically the condensation reaction is conducted employing a slight molar excess of the linking agent over the carbonyl-containing or quinone-containing therapeutic agent in methylene chloride at room temperature in the presence of triethylamine. The conjugation of linkers of formula (I) to carbonyl-containing or quinone-containing therapeutic agents is exemplified by the formation of 2-{[(9H-fluoren-9-ylmethoxy)carbonyl]amino}ethyl 4-{[(6Z)-2,2-dimethyl-5-oxo-3,4-dihydro-2H-benzo[h]chromen-6 (5H)-ylidene]amino}benzoate in Example 3 and Scheme 1.

Formation of a polymer-modified therapeutic agent may be conducted by reacting the Z group hydroxyl or amine of the linker conjugated therapeutic agent with a carboxyl-containing polymer to form the respective ester or amide bond. The reaction is commenced by first deprotecting the Z group of the linker to yield a deprotected amine or hydroxyl group, and condensing the hydroxyl or amine with a polymer carboxyl group. Suitable conditions for the condensation of the deprotected amine or hydroxyl groups with the polymer carboxyl group include reaction in a polar aprotic solvent such as DMF in the presence of a nucleophilic catalyst such as dimethyl amino pyridine and a dehydrating agent including, but not limited to, DCC (dicyclohexylcarbodiimide), HBTU (O-(benzotriazol-1-yl)-N,N,N',N'-tetramethyluronium hexafluorophosphate), HATU (N,N,N',N'-Tetramethyl-O-(7-azabenzotriazol-1-yl)uronium hexafluorophosphate), BOP ((benzotriazol-1-yloxy)tris(dimethylamino)phosphonium hexafluorophosphate), EDC (N-Ethyl-N'-(3-dimethylaminopropyl)carbodiimide), DMC (2-chloro-1,3-dimethylimidazolinium chloride), carbonyldiimidizole and other standard peptide coupling agents. HBTU is generally preferred. Alternatively, where the polymer contains acid anhydride groups, as in the case of styrene maleic anhydride polymers, the deprotected Z group hydroxyl or amine functionalities may be reacted with the polymer directly to form polymer-modified therapeutic agents having an ester or amide bond to the polymer in a mixture of aqueous NaHCO$_3$ and THF.

While it is possible to separately deprotect the Z group amines and form an amide linkage with a carboxyl-containing polymers, where the amine protecting group is Fmoc, or an Fmoc-related protecting group such as 2-chloro-1-indanylmethoxy-carbonyl (Climoc), benz[f]indene-3-methyloxycarbonyl (Bimoc), 2,7-di-t-butyl[9-(10,10-dioxo-10,10,-10,10-tetrahydrothioxanthyl)]methyl (DBD-Tmoc), 1,1-dioxobenzo[b]thiophene-2-ylmethyloxycarbonyl (Bsmoc), beta-trimethylsilylethyloxycarbonyl (Teoc) or (Bnpeoc), the formation of a polymer-modified therapeutic agent is preferentially performed without separately deprotecting and isolating the free amine product. Formation of polymer-modified therapeutic agents from linker conjugated therapeutic agents protected with Fmoc or Fmoc-related protecting groups may be conducted without isolation of the deprotected conjugate by reacting the linker conjugated therapeutic agent with 1,8-diazabicyclo [5.4.0]undec-7-ene (DBU) at room temperature in dimethylformamide (DMF). A carboxyl-containing polymer, such as PGA, PAA, or SMA containing maleic acid half ester residues, is then added followed by triethylamine and a condensing agent (preferably HBTU). After reacting at room temperature for 8 to 16 hours, the reaction mixture is mixed with aqueous sodium bicarbonate, filtered and the solution freeze-dried. The resulting solid is dialyzed and the product isolated by freeze-drying. This process is exemplified by the formation of N-{2-[(4-{[(6Z)-2,2-dimethyl-5-oxo-3,4-dihydro-2H-benzo[h]-chromen-6 (5H)-ylidene]amino}benzoyl)oxy]ethyl} γ-poly-L-glutamate in Example 4 and Scheme 1. Suitable polymers for forming the polymer-modified therapeutics employing a linking agent of formula I include, but are not limited to, PGA or PAA having a molecular weight from about 5,000 Da to about 100,000 Da, or from about 7,000 Da to about 80,000 Da, or from about 10,000 Da to about 70,000 Da. Other suitable molecular weight ranges for PGA and PAA polymers for forming the polymer-modified therapeutics employing a linking agent of formula I include, but are not limited to, from about 12,000 Da to about 28,000 Da, or from about 15,000 Da to about 24,000 Da, or from about 20,000 to about 80,000 Da, or from about 30,000 to about 70,000 Da, or from about 45,000 to about 60,000 Da. Particularly useful PGA and PAA polymers for forming polymer-modified therapeutics may have an average molecular weight of about 17,000 Da, or an average molecular weight of about 22,000 Da, or an average molecular weight of about 56,000 Da, and PGA is preferred.

In a preferred embodiment, where the therapeutic agent is β-lapachone, the imine polymer conjugate is of the form

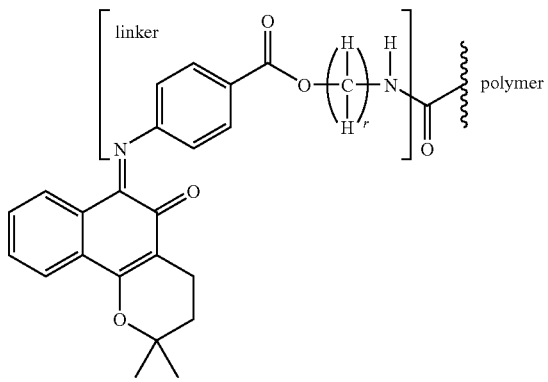

where r is from 1 to 6. In a more preferred embodiment, r is 2, the polymer is polyglutamic acid, and the β-lapachone conjugate is of the form

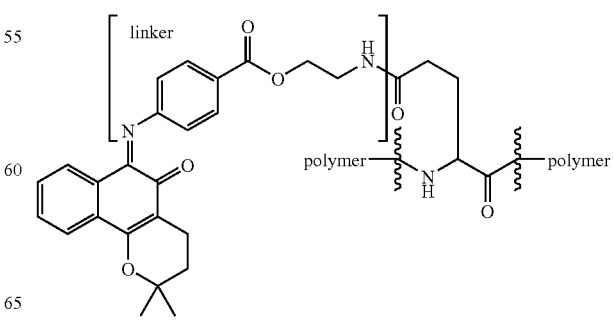

where polymer indicates the points of attachment to other glutamic acid residues of the polyglutamic. While a single regioisomer is indicted above, the opposite regioisomer, which invloves imine bond formation at the other quinone carbonyl may be prepared and is considered within the scope of this invention.

The quantity of therapeutic agents bound to carboxyl-containing polymers via a linking agent of formula (I) may be determined by hydrolysis of the imine linkage and quantitation of the released therapeutic agent. Hydrolysis of the imine may be conducted in aqueous acid (1.0 M HCl), and the reaction may be warmed as necessary to complete the hydrolysis. Free therapeutic agents may be quantitated by any suitable means including HPLC or UV/Vis spectroscopy. A polymer conjugate may contain therapeutic agents from about 2% to about 35% by weight based upon the polymer conjugate. In other embodiments, a polymer conjugate may be from about 6% to about 30% of the therapeutic by weight, or about 7% to about 28% of the therapeutic by weight, or about 10% to about 20% of the therapeutic by weight. For polymer-modified β-lapachone compounds where the polymer is polyglutamic acid, conjugates may be from about 5% to about 40% by weight of β-lapachone, in other embodiments conjugates are from about 8% to about 25% β-lapachone by weight, or about 10% to about 20% β-lapachone by weight based upon the total weight of the polyglutamic acid modified β-lapachone composition.

3. Quinol-Ester Polymer Conjugates.

Quinone-containing therapeutic agents may be conjugated to polymeric vehicles through an ester bond between a linking agent and one hydroxyl of a reduced quinone (i.e., a quinol) functionality, where the second quinol hydroxyl group is separately esterified with a carboxylic acid. Quinol-ester polymer conjugates are of the generic form

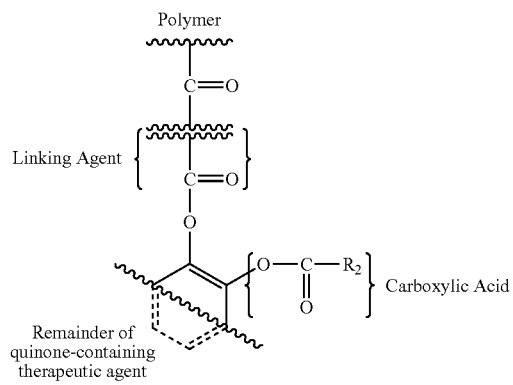

which is shown for a 1,2 quinol, although quinol-ester polymer conjugates may also be formed with 1,4 quinols (quinones). Where the carbonyl groups of a quinone are not equivalent, both individual regioisomers, and mixtures of both regioisomers, that may be formed by attachment of the linking agent to the non-equivalent carbonyls of the quinone, are considered within the scope of this invention. Linking agents suitable for forming ester-conjugated quinols include a group, such as an amino group, capable of attaching the linking agent to a carboxyl group on a polymeric vehicle by an amide linkage.

Carboxylic acids suitable for separately esterifying the second quinol hydroxyl are of the formula $R_2COOH$, where $R_2$ is $(C_1-C_8)$ alkyl, cycloalkyl, aryl, heterocycle, heteroaryl, aryl-alkyl, or alkylaryl, wherein said alkyl and cycloalkyl groups within $R_2$ may be substituted with one or more substituents independently selected from the group consisting of —H and —F, and wherein said aryl groups within $R_2$ may be substituted with one or more substituents independently selected from the group consisting of —H and halogen. In some preferred embodiments, $R_2$ is $(C_1-C_8)$ alkyl, in other preferred embodiments $R_2$ is (C1-C2) alkyl, and in other preferred embodiments $R_2$ is methyl.

In one embodiment the linking agents include natural and unnatural amino acids of the formula (II):

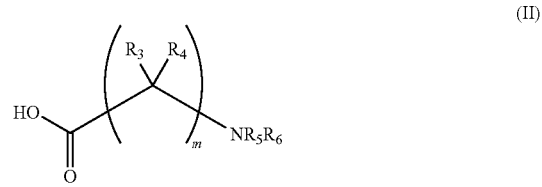

where
each $R_3$ and $R_4$ are independently selected from the group consisting of hydrogen, —$(C_1-C_8)$ alkyl, —O—$(C_1-C_8)$ alkyl, —$(C_1-C_4)$ alkyl-aryl, aryl, and heteroaryl;
$R_5$ is selected from the group consisting of hydrogen, —$(C_1-C_8)$ alkyl, —$(C_1-C_8)$ fluoroalkyl, aryl, and heteroaryl;
$R_6$ is selected from the group consisting of -tert-butoxycarbonyl and CBZ; and
m is from 1 to 8;
alternatively, when m is 1, $R_4$ and $R_5$ may be taken together with the carbon and nitrogen atoms bearing them to form a 4 to 7 membered nitrogen-containing heterocycle.

Linkers of formula II where m is 1 and $R_4$ and $R_5$ taken together with the carbon and nitrogen atoms bearing them form a 4 to 7 membered nitrogen-containing heterocyclic or heteroaryl ring are of the form:

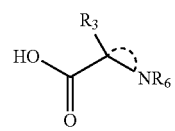

where the dashed line represents the remainder of the 4-7 membered nitrogen containing heterocyclic or heteroaromatic ring. In one such embodiment, the linker of formula II is proline, or more preferably L-proline.

In some embodiments, m is from 1-3, and in other embodiments m is from 4-8. In other embodiments, at least one independently selected $R_3$ or $R_4$ group is not H. In a more preferred embodiment, $R_3$ and $R_4$ are H, and m is from 1-6. In still another preferred embodiment, $R_3$ and $R_4$ are H, m is 1, $R_5$ is hydrogen and $R_6$ is tert-butoxycarbonyl; and the linking agent is N-tert-butoxycarbonyl glycine (tBoc glycine or Boc glycine):

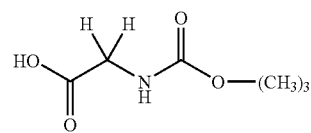

Linkers of formula (II) may be purchased from a variety of suppliers such as Sigma-Aldrich. Where $R_6$ is a t-Boc or CBZ group, the linkers may be prepared from the amino acid by protection with Boc anhydride (di-t-butyl dicarbonate; di-t-butyl pyrocarbonate; $Boc_2O$) or CBZ chloride (carbobenzyloxy chloride) respectively.

In one embodiment, quinol-ester linker conjugated therapeutic agents are of the form

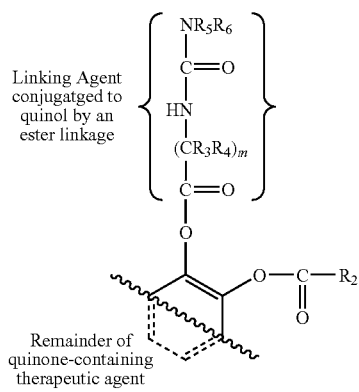

(which is shown for a 1,2 quinol, although quinol-ester linker conjugates may also be formed from 1,4 quinones (1,4 quinols));

where $R_2$ is ($C_1$-$C_8$) alkyl, cycloalkyl, aryl, heterocycle, heteroaryl, aryl-alkyl, or alkylaryl, wherein said alkyl and cycloalkyl groups within $R_2$ may be substituted with one or more substituents independently selected from the group consisting of —H and —F, and wherein said aryl groups within $R_2$ may be substituted with one or more substituents independently selected from the group consisting of —H and halogen;

each $R_3$ and $R_4$ are independently selected from the group consisting of hydrogen, —($C_1$-$C_8$) alkyl, —O—($C_1$-$C_8$) alkyl, —($C_1$-$C_4$) alkyl-aryl, aryl, and heteroaryl;

$R_5$ is selected from the group consisting of hydrogen, —($C_1$-$C_8$) alkyl, —($C_1$-$C_8$) fluoroalkyl, aryl, and heteroaryl;

$R_6$ is selected from the group consisting of -tert-butoxycarbonyl and CBZ; and m is from 1 to 8;

alternatively, when m is 1, $R_4$ and $R_5$ may be taken together with the carbon and nitrogen atoms bearing them to form a 4 to 7 membered nitrogen-containing heterocycle.

In some preferred embodiments $R_2$ is ($C_1$-$C_4$) alkyl, in a more preferred embodiment $R_2$ is C1 alkyl (i.e., the carboxylic acid of the form $R_2COOH$ is acetic acid).

In one embodiment of quinol-ester polymer conjugates, where the polymer is a carboxyl containing polymer, the conjugates are of the form

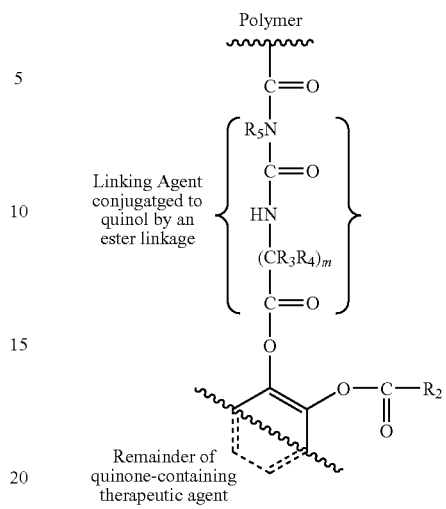

where $R_2$ is ($C_1$-$C_8$) alkyl, cycloalkyl, aryl, heterocycle, heteroaryl, aryl-alkyl, or alkylaryl, wherein said alkyl and cycloalkyl groups within $R_2$ may be substituted with one or more substituents independently selected from the group consisting of —H and —F, and wherein said aryl groups within $R_2$ may be substituted with one or more substituents independently selected from the group consisting of —H and halogen;

each $R_3$ and $R_4$ are independently selected from the group consisting of hydrogen, —($C_1$-$C_8$) alkyl, —O—($C_1$-$C_8$) alkyl, —($C_1$-$C_4$) alkyl-aryl, aryl, and heteroaryl;

$R_5$ is selected from the group consisting of hydrogen, —($C_1$-$C_8$) alkyl, —($C_1$-$C_8$) fluoroalkyl, aryl, and heteroaryl; and m is from 1 to 8;

alternatively, when m is 1, $R_4$ and $R_5$ may be taken together with the carbon and nitrogen atoms bearing them to form a 4 to 7 membered nitrogen-containing heterocycle.

In one preferred embodiment of quinol-ester polymer conjugates, shown generically for a 1,2-quinol and a carboxyl containing polymer, $R_2$ is $C_1$ alkyl (i.e., the carboxylic acid of the form $R_2COOH$ is acetic acid), $R_3$, $R_4$, and $R_5$ are each hydrogen, and m is 1:

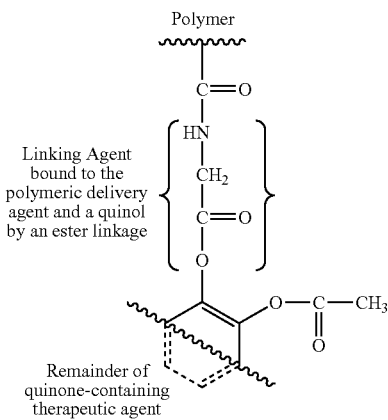

The preparation of quinol-ester polymer conjugates begins with the preparation of the linker conjugated therapeutic agent that may be prepared by reacting a linker of formula (II) with a quinone-containing therapeutic agent and an anhydride of the carboxylic acid $R_2COOH$ in a two step process. In the first step, a mixture of zinc dust the quinone-containing compound, $Na_2S_2O_4$, and an N-tert-butoxycarbonyl-protected (t-Boc) linker of formula (II), a dehydrating reagent (such as HBTU) are reacted. The first reaction step is typically conducted in a polar aprotic solvent, such as DMF at room temperature for 12-24 hours, preferably 16 hours. The product of the first reaction step is isolated by dilution with an organic solvent (e.g., ethyl acetate), followed by washing of the organic solvent reaction mixture with water, drying with $Na_2SO_4$, and concentration under reduced pressure to yield a residue. In the second step, the residue from the first step is dissolved in the acid anhydride of formula $(R_5C(=O))_2O$, and zinc dust and triethylamine are added. The mixture is heated to 90° C. for 1-4 hours, preferably 2 hours, with stirring. After cooling, solvent is removed under reduced pressure and the residue is dissolved in organic solvent (e.g., ethyl acetate), which is washed with water, dried with $Na_2SO_4$ and concentrated under reduced pressure to yield the t-Boc protected product quinol-ester linker conjugated therapeutic agent. The product is purified by flash column chromatography on silica gel employing a suitable solvent (e.g., ethyl acetate/dichloromethane), and may be further purified by crystallization. Deprotection of the amine by removal of the t-Boc group may be accomplished by any suitable procedure, including reaction with HCl in dioxane to yield the hydrochloride salt. The preparation of quinol-ester linker conjugated therapeutic agents by this route is exemplified by the preparation of 5-(acetyloxy)-2,2-dimethyl-3,4-dihydro-2H-benzo[h]chromen-6-yl N-(tert-butoxycarbonyl)glycinate, which is described in Example 5a and Scheme 2a.

Scheme 2a

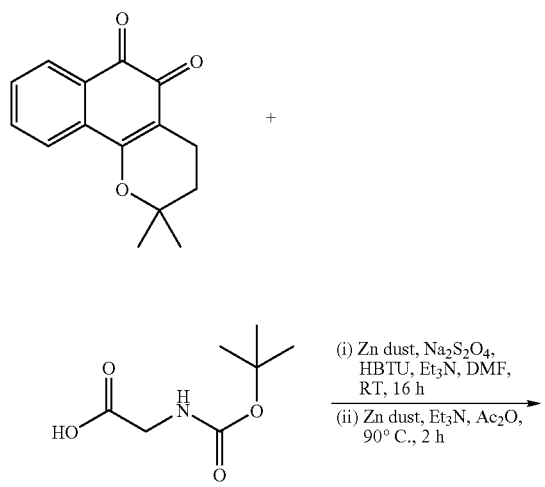

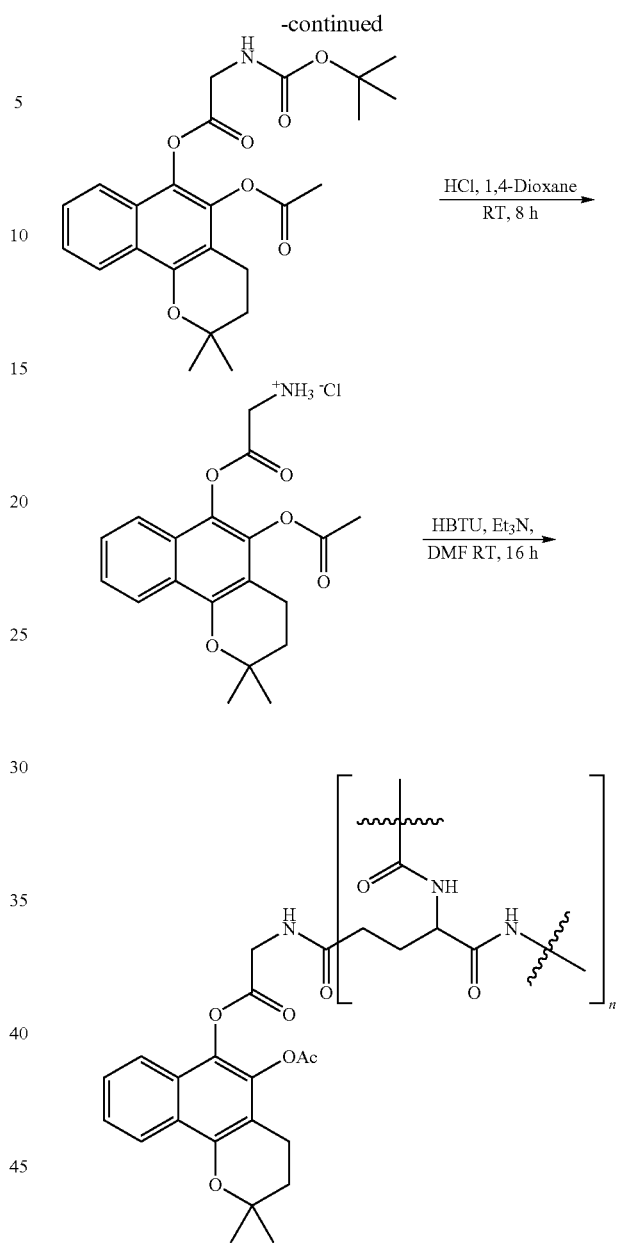

In an alternative protocol, preparation of quinol-ester linker conjugated therapeutic agents may be prepared by reacting a linker of formula (II) with a quinone-containing therapeutic agent in the presence of Zn dust and HBTU in a first reaction step. The product of the first reaction step is then treated with Zn dust, triethylamine and the anhydride of the carboxylic acid $R_2COOH$ in a second reaction step. The first reaction step is typically conducted in a polar aprotic solvent such as DMF at room temperature for 16 hours. The second reaction step is generally conducted at room temperature for 1-2 hours. The preparation of quinol-ester linker conjugated therapeutic agents by this route is exemplified by the preparation of 5-(acetyloxy)-2,2-dimethyl-3,4-dihydro-2H-benzo[h]chromen-6-yl N-(tert-butoxycarbonyl)glycinate, in Example 5b and Scheme 2b.

Scheme 2b

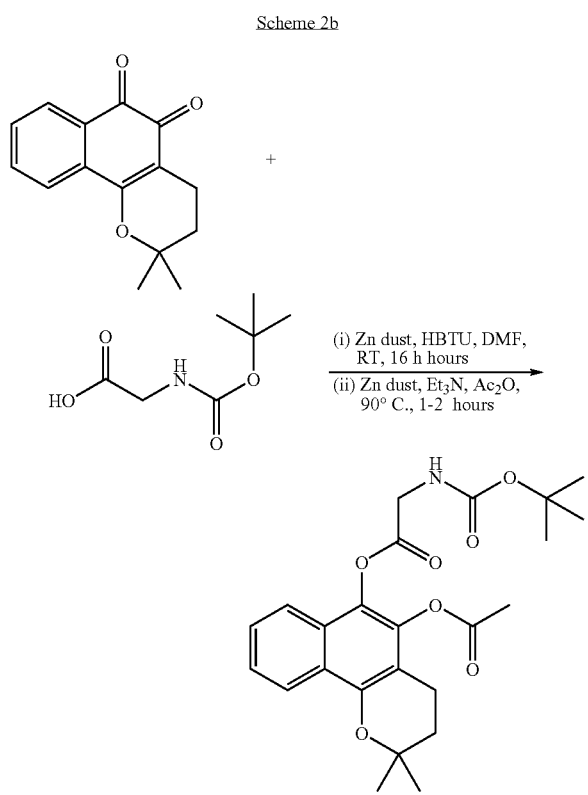

The conversion of protected (e.g., Boc protected) quinol-ester linker conjugated therapeutic agents into their deprotected hydrochloride form is exemplified by the conversion of 5-(Acetyloxy)-2,2-dimethyl-3,4-dihydro-2H-benzo[h]chromen-6-yl N-(tert-butoxycarbonyl)glycinate, prepared as in examples 5a or 5b, to its hydrochloride form (5-(acetyloxy)-2,2-dimethyl-3,4-dihydro-2H-benzo[h]chromen-6-yl glycinate hydrochloride) as in Examples 6a or 6b.

Formation of quinol-ester polymer conjugates may be conducted by reaction of a suitable carboxyl-containing polymer with the deprotected quinol-ester linker conjugated therapeutic agent in the presence of a dehydrating agent. The reaction is typically conducted in a polar aprotic solvent such as DMF at room temperature for 16 hours. Where necessary the time and temperature may be adjusted accordingly; suitable times are from 10-30 hours and the reaction may be conducted from about 0° to about 50° C. or more preferably from about 15° to about 37° C. After the reaction is complete, the reaction is diluted with water and aqueous HCl is added to precipitate the product quinol-ester polymer conjugated therapeutic agent. The product is collected by centrifugation and is washed with aqueous HCl (e.g., 1.0 N HCl), deionized water, and lyophilized. In preferred embodiments, the carboxyl-containing polymer is polyglutamic acid (PGA) or polyaspartic acid (PAA). PGA and PAA having a molecular weight from about 5,000 Da to about 100,000 Da, or from about 7,000 Da to about 80,000 Da, or from about 10,000 Da to about 70,000 Da may be employed, other molecular weight ranges of PGA and PAA that may be employed include from about 12,000 Da to about 28,000 Da, or from about 15,000 Da to about 24,000 Da, or from about 20,000 to about 80,000 Da, or from about 30,000 to about 70,000 Da, or from about 45,000 to about 60,000 Da, and particularly PGA of about 17,000 Da, or about 22,000 Da, or about 56,000 Da may also be employed. DCC (dicyclohexylcarbodiimide), HBTU (O-(benzotriazol-1-yl)-N,N,N',N'-tetramethyluronium hexafluorophosphate), HATU (N,N,N',N'-Tetramethyl-O-(7-azabenzotriazol-1-yl) uronium hexafluorophosphate), BOP ((benzotriazol-1-yloxy)tris(dimethylamino)phosphonium hexafluorophosphate), EDC (N-Ethyl-N'-(3-dimethylaminopropyl) carbodiimide), DMC (2-chloro-1,3-dimethylimidazolinium chloride), carbonyldiimidizole and other standard peptide coupling agents. The preparation of quinol-ester polymer conjugates is exemplified by the preparation of the polymer-modified β-lapachone 5-(acetyloxy)-2,2-dimethyl-3,4-dihydro-2H-benzo[h]chromen-6-yl glycinate γ-poly-L-glutamate in Example 7 and the lower portion of Scheme 2a. Alternatively, where the polymer contains acid anhydride groups, as in the case of styrene maleic anhydride (SMA) polymers, the hydrochloride salt of the amine may be reacted with the polymer in a mixture of aqueous NaHCO$_3$ and THF to form polymer-modified therapeutic agents having an amide bond to the polymer. Coupling to an acid anhydride containing polymer is exemplified by the reaction of 5-(acetyloxy)-2,2-dimethyl-3,4-dihydro-2H-benzo[h]chromen-6-yl glycinate hydrochloride with SMA in Example 8.

The quantity of therapeutic agent conjugated with a carboxyl-containing polymer via a quinol-ester linkage may be determined by hydrolysis of the ester linkage and quantitation of the released therapeutic agent. Hydrolysis of the quinol-ester linkage may be conducted in aqueous base (e.g., 0.01 N NaOH), and the reaction may be warmed as necessary to drive the hydrolysis. Free therapeutic agents may be quantitated by any suitable means including HPLC, LC-MS (liquid chromatography-mass spectroscopy) or UV/Vis spectroscopy. For polymer-modified β-lapachone compounds linked to PGA or PAA via a quinol-ester linkage, conjugates are generally from about 5% β-lapachone to about 45% β-lapachone by weight. In some embodiments, conjugates are from about 8% to about 25% β-lapachone or from about 10% to about 20% β-lapachone by weight based upon the total weight of the polyglutamic acid modified β-lapachone. In other embodiments, conjugates are from about 25% β-lapachone to about 45% β-lapachone by weight, or from about 30% to about 40% β-lapachone by weight based upon the total weight of the polyglutamic acid modified β-lapachone. For polymer-modified β-lapachone compounds linked to SMA polymers via a quinol-ester linkage, conjugates are generally from about 5% β-lapachone to about 60% β-lapachone by weight, in some embodiments, they are from about 10% to about 55% β-lapachone or from about 20% to about 50% β-lapachone, or from about 30% to about 45% by weight based upon the total weight of the SMA modified β-lapachone.

Although only a single quinol-ester regiosiomer of polymer-modified quinone containing compounds, such as polymer-modified β-lapachone, has been shown, both regioisomer of polymer-modified compounds, and mixtures of both regioisomers of polymer-modified compounds are considered to be within the scope of this invention. Thus, for example, both quinol ester regioisomers of polymer-modified beta lapachone, where $R_2$ is $C_1$ alkyl (i.e., the carboxylic acid of the form $R_2COOH$ is acetic acid), $R_3$, $R_4$, and $R_5$ are each hydrogen, and m is 1:

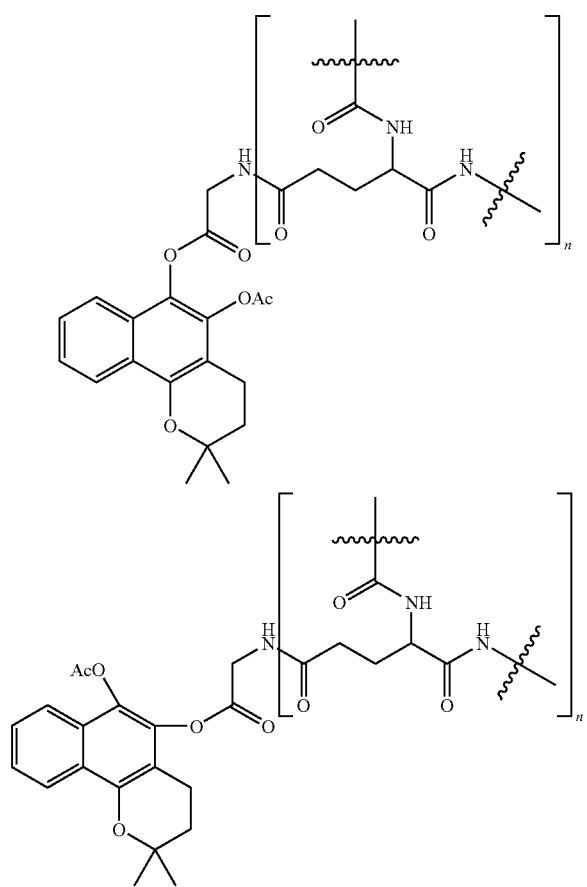

are considered to be within the scope of this invention, as are mixtures of both of those regioisomers.

4. Ketal Polymer Conjugates.

Therapeutic agents bearing a carbonyl or quinone group may be linked to polymer vehicles through the use of a ketal functionality or linkage. Linking agents suitable for the formation of ketal polymer conjugates provide vicinal diols for the formation of the ketal functionality or linkage, and a means, such as an additional hydroxyl or amino group, for attaching the linking agent to a carboxyl group on a polymeric vehicle via an amide linkage. In one embodiment, the linking agents are of the form of formula (III):

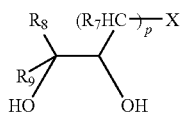
(III)

where

X is a hydroxyl, a protected hydroxyl or a protected amine;
each of $R_7$ and $R_8$ is independently selected from the group consisting of hydrogen, and ($C_1$-$C_4$) alkyl;
$R_9$ is H; and
p is 1-4.

Linking agents of formula (III) may be purchased from a variety of sources, for example, 1,2,6, hexanetriol, 1,2,4-butanetriol, glycerol, and 3-amino-1,2-propanediol are available from Sigma-Aldrich. In a preferred embodiment the ketal linking agent of formula (III) is glycerol (p is 1 and X is OH). In a related embodiment, the ketal linking agent of formula (III) is glycerol (p is 1 and X is a protected OH). In other embodiments, the linking agent of formula (III) is not glycerol. In yet another preferred embodiment the linking agent of formula (III) is 3-amino-1,2-propanediol.

Ketal polymer conjugates of carbonyl-containing therapeutic agents linked by a linking agent of formula (III) to a polymer are of the generic form:

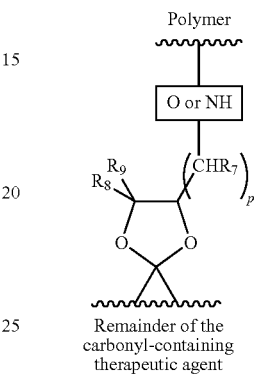

Ketal polymer conjugates of quinone-containing therapeutic agents linked by a linking agent of formula (III) to a polymer are of the generic form:

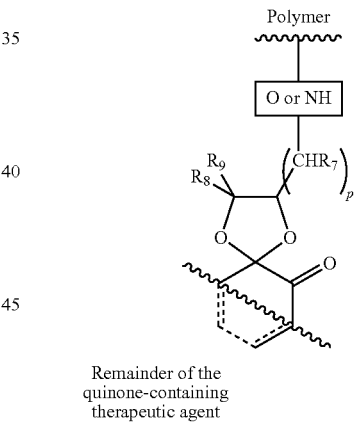

which is shown for a 1,2-quinone, although 1,4-quinones may also be conjugated via a ketal linkage.

Ketal polymer conjugates are prepared by the formation of the ketal linker conjugated therapeutic agent followed by reaction of the ketal linker conjugated therapeutic agent with a polymeric vehicle. Ketal linker conjugated therapeutic agents may be prepared by reaction of a linker of formula (III) with a quinone-containing therapeutic agent. The reaction is typically conducted in benzene in the presence of a catalytic amount of acid (e.g., p-toluenesulfonic acid monohydrate) by refluxing the mixture for 6 hours. After cooling the reaction solvent is removed and the product is purified by chromatography on silica gel as necessary. The preparation of ketal linker conjugated therapeutic agents is exemplified for the conversion of β-lapachone to 4'-(hydroxymethyl)-2,2-dimethyl-3,4-dihydro-2H,5H-spiro[benzo[h]chromene-6,2'-[1,3]dioxolan]-5-one in Examples 9a and in Scheme 3 (stereochemistry is not shown).

Where a ketal linked therapeutic agent is prepared employing a linker of formula III where X is a hydroxyl or a protected hydroxyl group, the linker hydroxyl group may be converted to an amine functionality by conversion to the methansulfonyl ester, followed by reaction with sodium azide to form the corresponding azidomethyl compound, which may be converted to an amine by treatment with triphenylphosphine in THF. This sequence of reaction steps is illustrated in Example 9b for the conversion of 4'-(hydroxymethyl)-2,2-dimethyl-3,4-dihydro-2H,5H-spiro[benzo[h]chromene-6,2'-[1,3]dioxolan]-5-one (316 mg, 1.0 mmol) to 4'-(aminomethyl)-2,2-dimethyl-3,4-dihydro-2H,5H-spiro[benzo[h]chromene-6,2'-[1,3]dioxolan]-5-one.

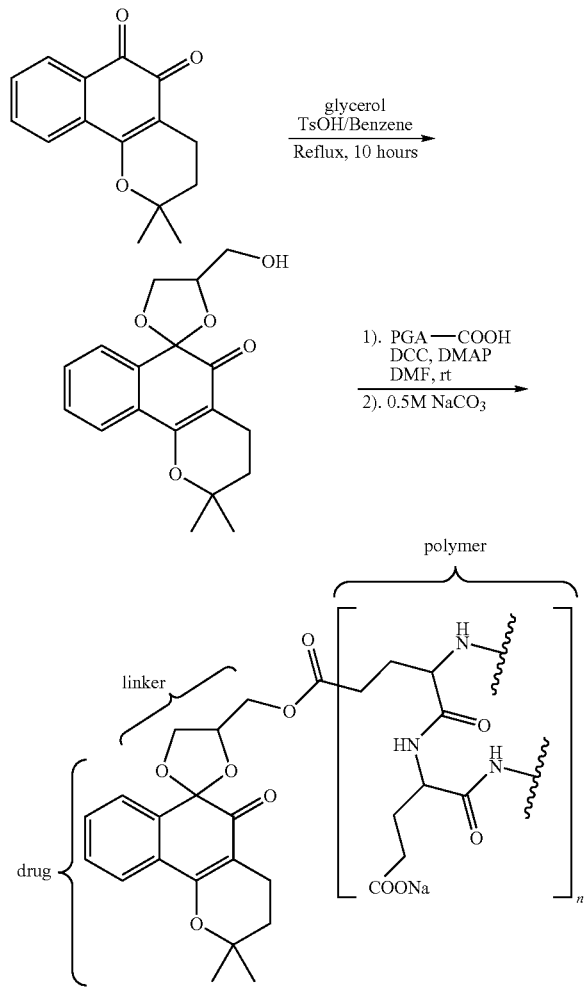

Ketal polymer conjugates may be prepared by reacting the ketal linker conjugated therapeutic agent with a carboxyl-containing polymeric vehicle. Where the linker of formula (III) is protected (e.g., X is a protected amine or hydroxyl group), the protecting group is removed to give a free amine or hydroxyl functionality. The reaction is typically conducted in a polar aprotic solvent, such as DMF, in the presence of a dehydrating agent for 8 to 16 hours at room temperature. The resulting mixture is diluted with an organic solvent (e.g., chloroform), mixed with 0.5 M sodium bicarbonate; the resulting aqueous layer is washed again with organic solvent. After dialyzing the aqueous layer against deionized water the product is isolated by lyophilization. In preferred embodiments, the carboxyl-containing polymer is polyglutamic acid (PGA) or polyaspartic acid (PAA). PGA and PAA having a molecular weight from about 10,000 Da to about 75,000 Da may be employed, other molecular weight ranges are from about 12,000 Da to about 22,000 Da or from about 45,000 to about 60,000 Da, and particularly PGA of about 17,000 Da or about 56,000 Da may also be employed. Preferred dehydrating agents include, but are not limited to, DCC (dicyclohexylcarbodiimide), HBTU (O-(benzotriazol-1-yl)-N,N,N'-tetramethyluronium hexafluorophosphate), HATU (N,N,N',N'-Tetramethyl-O-(7-azabenzotriazol-1-yl)uronium hexafluorophosphate), BOP ((benzotriazol-1-yloxy)tris(dimethylamino)phosphonium hexafluorophosphate), EDC (N-Ethyl-N'-(3-dimethylaminopropyl)carbodiimide), DMC (2-chloro-1,3-dimethylimidazolinium chloride), carbonyldiimidizole and other standard peptide coupling agents. DCC is most preferred.

In a preferred embodiment of ketal polymer conjugates, the ketal linking agent is glycerol and the polymer is polyglutamic acid. This embodiment is described in Examples 9a and 10, and depicted Scheme 3 for the quinone-containing therapeutic, β-lapachone. In another preferred embodiment the linking agent is 3-amino-propane-1,2-diol. In other embodiments, ketal polymer conjugates may be prepared with SMA polymers having an average molecular weight from about 8,000 Da to about 17,000 Da or from about 10,000 Da to about 15,000 Da or from about 11,000 to about 13,000 Da. Other particularly useful SMA polymers for forming ketal polymer conjugates may have an average molecular weight of 1,200 Da, 16,000 Da or 12,000 Da.

The quantity of therapeutic agent conjugated with a carboxyl-containing polymer via a ketal linkage may be determined by hydrolysis of the ester linkage and quantitation of the released therapeutic agent. Hydrolysis of the ketal-linkage, as described in Examples 10 and 11(c), may be conducted in aqueous base (e.g., NaOH) or acid and the reaction may be warmed as necessary to drive the hydrolysis. Free therapeutic agents may be quantitated by any suitable means including LC/MS, HPLC or UV/Vis spectroscopy. For polymer-modified β-lapachone compounds linked to PGA (17,000 Da) via a ketal linkage, conjugates may be from about 5% β-lapachone to about 30% β-lapachone by weight, or from about 10% to about 25% β-lapachone or from about 15% to about 20% β-lapachone based upon the total weight of the polyglutamic acid modified β-lapachone.

Although only a single ketal polymer conjugate of β-lapachone has been shown, both ketal polymer conjugate regioisomers of β-lapachone compounds, and mixtures of both regioisomers, are considered within the scope of this invention.

5. Biological Activity of Polymer Conjugated Therapeutic Agents of the Invention.

Therapeutic agents may be released from their polymer-modified forms by a variety of mechanisms that result in the cleavage of the bonds between the therapeutic agent and the linking agent. The release of the therapeutic agent may occur from a linking agent while the linking agent is still bound to the polymer, or in the alternative, after the linker conjugated therapeutic agent is cleaved from the polymer. Release of quinone-containing and carbonyl-containing therapeutic agents from the polymer-modified form may occur by a variety of mechanisms including, but not limited to, non-enzymatic hydrolysis of the bond or bonds between the therapeutic agent and the linker and enzyme catalyzed cleavage (e.g., esterase or Cytochrome P450 action). The imine, quinol-ester, and ketal linking agents described herein each permit release of quinone-containing and carbonyl-containing therapeutic agents as free quinones and carbonyl compounds without modification of the therapeutic agent, particularly where the release occurs by hydrolysis. Depending upon the specific therapeutic agent and linker combination, and to some extent the polymer employed in preparing the polymer-modified therapeutic agent, release of therapeutic agents may occur in a variety of locations upon administration to a subject. Where the subject is a mammal, release may occur, for example, in the interstitial or intracellular spaces within a tumor, or within a cell or a cellular organelle such as a lysosome where the polymer conjugate becomes internalized by cells. Where the polymer-modified therapeutic enters the blood stream, for example when administered as an intravenous formulation, release of therapeutic agents from their polymer-modified forms may also occur in plasma during circulation as indicated in Examples 15. Additionally, release of therapeutics from polymer-modified forms may occur at a site of administration, such when the polymer-modified therapeutic is administered intraperitonally or subcutaneously.

The ability of the polymer-modified therapeutic agents of the invention to deliver therapeutic agent can be observed in the action of the polymer-modified therapeutic agent β-lapachone on cells in vitro, described in Example 12, and in nude mice tumor models described in Example 15.

Figure 5B:
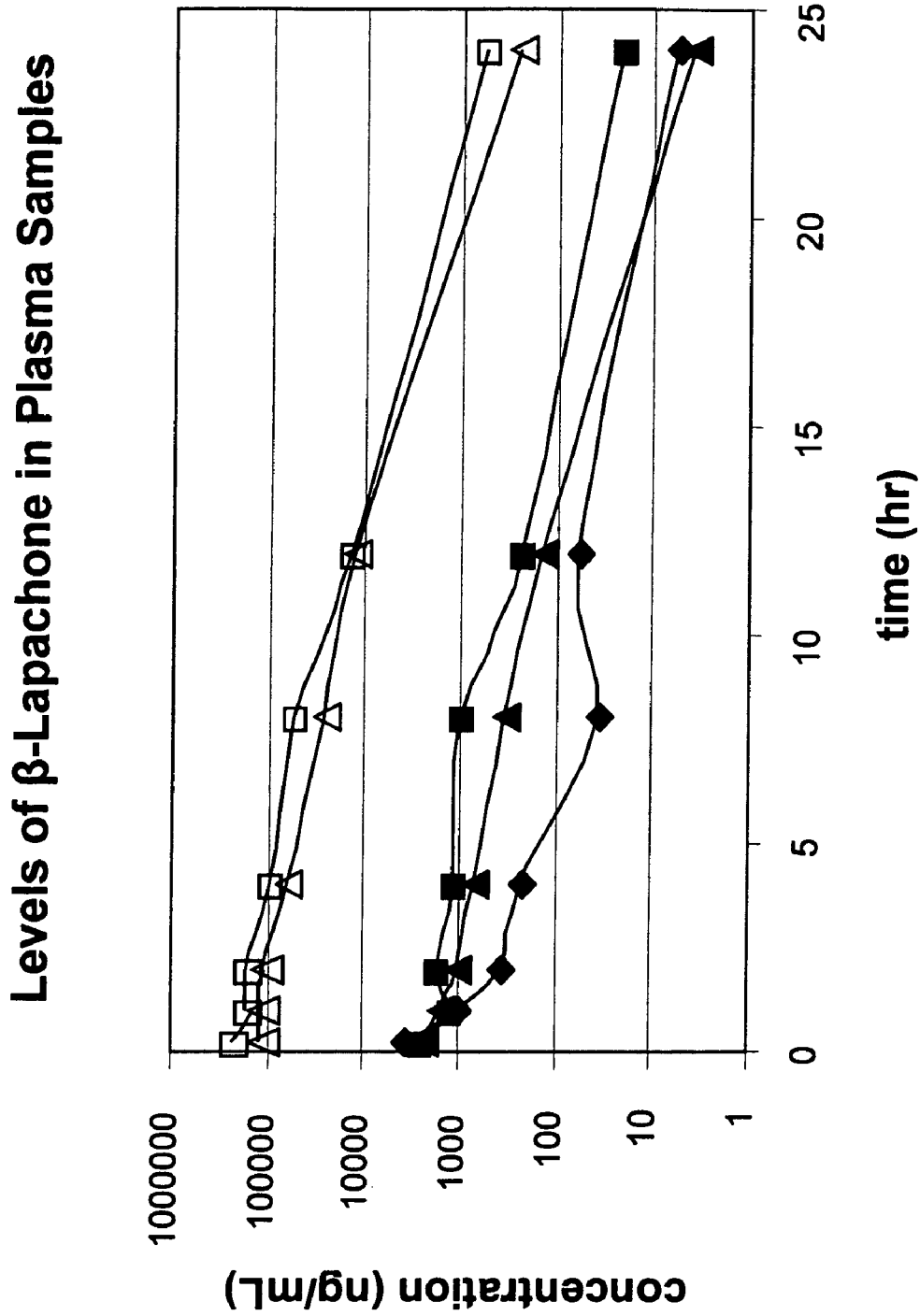

The ability of the polymer-modified therapeutic agents to sustain therapeutic levels of the agent can be observed in FIGS. 3, 5A and B compared with the unmodified therapeutic agent (reference standard). Levels of free therapeutic agent released from the conjugate and total (free plus conjugate) levels of the therapeutic agent are sustained in tumor above the levels of the reference (therapeutic agent) starting from two or four hours to twenty-four hours post delivery of the agents (FIGS. 3 and 5A). Additionally plasma levels of free and total (free plus conjugate) levels are sustained above unmodified therapeutic agent levels for twenty-four hours (FIGS. 3 and 5B).

E. POLYMER CONJUGATED THERAPEUTIC AGENTS OF THE INVENTION

The present invention includes polymer-modified quinone-containing or carbonyl-containing therapeutic agents. In a preferred embodiment, the therapeutic agents are conjugated to the polymeric vehicle by an imine, quinol-ester, or ketal linkage formed between the therapeutic agent and the linking agent. Upon hydrolysis, such linkages advantageously release conjugated carbonyl or quinone therapeutic agent from the polymeric delivery vehicle without alteration of the drug. In a more preferred embodiment, the polymeric delivery vehicle selected from PAA or PGA. In another more preferred embodiment of the invention, the therapeutic agents are chemotherapeutic agents, such as mitomycin C, doxorubicin, actinomycin D (dactinomycin), β-lapachone or a lapachone analog.

In accordance with the present invention, preferred therapeutic agents include β-lapachone. In preferred embodiments, the polymer-conjugates of β-lapachone comprise a polymeric delivery vehicle selected from PGA or PAA bound to β-lapachone by an imine, quinol-ester, or ketal linkage formed between β-lapachone and a linking agent. In some embodiments of β-lapachone polymer conjugates, the polymeric vehicle is PGA or PAA, the conjugates may be from about 5% β-lapachone to about 40% β-lapachone by weight, or from about 8% to about 25% β-lapachone, or from about 10% to about 20%β-lapachone by weight, or from about 26% to about 38% β-lapachone by weight based upon the total weight of the polymer conjugate. Where the polymeric vehicle is SMA, β-lapachone is advantageously bound to a carboxyl-containing polymeric vehicle by a quinol-ester linkage between the linking agent and β-lapachone. In some embodiments of β-lapachone-SMA polymer conjugates, the conjugates are preferably from about 25% to about 60% β-lapachone by weight, or from about 35% to about 55% β-lapachone by weight, or from about 40% to about 50% β-lapachone by weight, based upon the total weight of the polymer conjugate.

The above-described polymer conjugates offer a variety of advantages for the delivery of therapeutic agents containing a carbonyl or quinone functionality. Where effective transport of therapeutic agents, such β-lapachone compounds, to tumor cells or tumor tissues is desired to promote therapeutic effectiveness, the polymer conjugates advantageously permit selective delivery through the EPR effect in tumor tissues. Furthermore, where therapeutic agents, and particularly chemotherapeutics have limited water solubility, conjugation to water soluble carboxyl-containing polymers advantageously provides a means of solubilizing the therapeutic agent for delivery. Moreover, as the polymer compositions and linkers of the present invention release quinone and carbonyl-containing therapeutic agents by hydrolysis of the imine, quinol-ester, or ketal linkages without alteration of the therapeutic agents, these compositions are advantageously employed to deliver quinone-containing or carbonyl-containing therapeutic agents, without any required the introduction of additional functionalities or groups that may alter the structure, function, activity or metabolism of the therapeutic agents.

F. METHODS OF THE INVENTION

The methods of the invention include the use of linking agents of formulas (I), (II), or (III) for the preparation of polymer-modified carbonyl-containing or quinone-containing therapeutic agents, in which the carbonyl-containing or quinone-containing therapeutic agents are bound to a carboxyl-containing polymer via the linking agents of formulas (I), (II), or (III). More specifically, methods of preparing polymer conjugates of carbonyl-containing or quinone-containing therapeutic agents including lobeline, acebutolol, methyprylon, haloperidol, molindone, naloxone, oxycodone, methadone, ketanserin, tolmetin, ketoprofen, nabumetone, canrenone, canrenonate, mebendazole, oxolinic acid, tetracycline, chlortetracycline, oxytetracycline, demeclocycline, doxycycline, minocycline, daunorubicin, doxorubicin, mitoxantrone, plicamycin, mitomycin, indan-1,3-dione, anisindione, testosterone (and related C-17 esters, e.g., propionate, enanthate, cypionate), dihydrotesterone, cyproterone acetate, estrone, progesterone, medroxyprogesterone acetate, hydroxyprogesterone caproate, norethindrone, norethynodrel, megestrol acetate, norgestrel, mifepristone, methandrostenolone, oxandrolone, testolactone, cyproterone acetate, prednisone, prednisolone, betamethasone, dexamethasone, other 3-, 17-, or 20-ketosteroids (e.g., dehydroepiandorsterone, androstenedione, cortisol, cortisone, aldosterone, etc.), and particularly β-lapachone compounds.

Another aspect of the present invention relates to methods for treating cancer or other cell proliferative disorder comprising administering a composition comprising a therapeutically effective amount of at least one polymer-modified therapeutic agent, such as a β-lapachone compound, to a subject in need thereof. Another aspect of the invention relates to methods for enhancing the accumulation of chemotherapeutic agents, such as β-lapachone or an analog thereof, in a tumor tissue. Such a method generally comprises providing a polymer-modified therapeutic agent, such as β-lapachone or an analog thereof, and administering it to a patient or subject bearing a tumor tissue, thereby contacting the tumor tissue with the agent where it may accumulate. In a preferred embodiment the method is a method of enhancing the accumulation of chemotherapeutic agents in a tumor of patient. In preferred embodiments, the methods of the invention are particularly useful as methods for the treatment of mammalian cancers, including, but not limited to, lung cancer, breast cancer, colon cancer, ovarian cancer, prostate cancer, multiple myeloma or malignant melanoma, or accumulation of therapeutic agents in such cancer tissues. In other embodiments, the methods of treatment include treatment of carcinoma, adenocarcinoma, and sarcoma. In more preferred embodiments the methods of treatment are methods of treating a human. Due to the ability to conjugate substantial amounts of quinone-containing or carbonyl-containing therapeutic agents to the polymeric vehicles employing the linking chemistries of the present invention the methods of the invention avoid the necessity of delivering large amounts of solubilizing agents, such as cyclodextrins, that are often required to deliver therapeutic quantities of water-insoluble compounds, and which have their own toxicological issues.

According to the methods of the invention, the polymer-modified therapeutic agents of the invention may be administered to a subject via any suitable delivery route known in the art. Specific exemplary administration routes include peripheral and central routes such as intralymphatic (e.g., intra-lymph node), intravenous (bolus and infusion), and intracerebral. Other routes such as oral, ocular rectal, buccal, topical, nasal, subcutaneous and intramuscular may be employed. In preferred embodiments the route of administration is parenteral administration. In the most preferred embodiments the route of administration is intravenous.

As used herein the term "therapeutically effective amount" refers to an amount of a pharmaceutical agent to treat, ameliorate, or prevent the identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the therapeutics employed to form the polymer-modified therapeutic agents of the present invention indicate an initial target plasma concentration of the unconjugated therapeutics ranging from approximately 0.1 µg/ml to approximately 100 µg/ml, preferably from approximately 0.1 µg/ml to approximately 50 µg/ml, more preferably the unconjugated therapeutics will have an initial target plasma concentration from approximately 1 µg/ml to approximately 25 µg/ml. To achieve such plasma concentrations, the polymer-modified therapeutic agents of the present invention may be administered at doses that vary from 0.1 mg to 2,000 mg, depending upon the route of administration. Guidance as to particular dosages and methods of delivery is provided in the literature and is generally available to practitioners in the art. In general the dose of the therapeutic agent will be in the range of about 0.1 mg/day to about 2 g/day, or about 0.5 mg to about 2 g/day, or about 1 mg to about 1 g/day not including the weight of polymeric vehicle. The dose may be administered in a single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage, and route of administration are adjusted to provide sufficient levels of the active agent(s) or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a non-cancerous condition, e.g., rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis;

allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus. In another aspect, a cell proliferative disorder includes a precancer or a precancerous condition. In another aspect, a cell proliferative disorder includes cancer. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, chronic myelogenous leukemia, hematologic tumor, and lymphoid tumor, including metastatic lesions in other tissues or organs distant from the primary tumor site. Cancers to be treated include but are not limited to sarcoma, leiomyosarcoma, carcinoma, and adenocarcinoma. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi) PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter, such as a polymer-modified therapeutic agent, is in direct contact with a cell, or is close enough to induce a desired biological effect in a cell.

As used herein, "candidate compound" refers to a compound of the present invention that has been or will be tested in one or more in vitro or in vivo biological assays, in order to determine if that compound is likely to elicit a desired biological or medical response in a cell, tissue, system, animal or human that is being sought by a researcher or clinician. In one aspect, in vitro or in vivo biological assays include, but are not limited to, enzymatic activity assays, electrophoretic mobility shift assays, reporter gene assays, in vitro cell viability assays, and the assays set forth in Examples 12-15.

As used herein, "monotherapy" refers to administration of a single active or therapeutic compound, such as a polymer conjugate containing a single type of therapeutic agent, to a subject in need thereof. Preferably, monotherapy will involve administration of a therapeutically effective amount of an active compound. Monotherapy may be contrasted with combination therapy, in which a combination of multiple active compounds is administered, preferably with each component of the combination present in a therapeutically effective amount. In one aspect, montherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating a cancer of the present invention results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating a cancer of the present invention results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating a cancer of the present invention results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating a cancer of the present invention results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating a cancer of the present invention results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound, such as a polymer-modified therapeutic agent of the invention. In another preferred aspect, an increase in average survival time of a population may also be measured, for example, by calculating for a population the average length of survival following completion of a first round of treatment with an active compound such as a polymer-modified therapeutic agent of the invention.

In another aspect, treating a cancer of the present invention results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound, such as a polymer-modified therapeutic agent of the invention. In another preferred aspect, an increase in average survival time of a population may also be measured, for example, by calculating for a population the average length of survival following completion of a first round of treatment with an active compound such as a polymer-modified therapeutic agent of the invention.

In another aspect, treating a cancer of the present invention results in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound, such as a polymer-modified therapeutic agent of the invention. In another preferred aspect, an increase in average survival time of a population may also be measured, for example, by calculating for a population the average length of survival following completion of a first round of treatment with an active compound, such as a polymer-modified therapeutic agent of the invention.

In another aspect, treating a cancer of the present invention results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound, such as a polymer-modified therapeutic agent of the invention. In another preferred aspect, a decrease in the mortality rate of a population may also be measured, for example, by calculating for a population the average number of disease-related deaths per unit time following completion of a first round of treatment with an active compound, such as a polymer-modified therapeutic agent of the invention.

In another aspect, treating a cancer of the present invention results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating a cancer of the present invention results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder of the present invention results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder of the present invention results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder of the present invention results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder of the present invention results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

In one aspect, preventing cancer metastases results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, preventing cancer metastases results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

As used herein, the term "selectively" means tending to occur at a higher frequency in one population than in another population. In one aspect, the compared populations are cell populations. In a preferred aspect, a compound of the present invention, such as a polymer-modified therapeutic agent of the invention or a pharmaceutically acceptable salt, prodrug, metabolite, analog or derivative thereof, acts selectively on a cancer or precancerous cell but not on a normal cell. In another preferred aspect, a compound of the present invention, or a pharmaceutically acceptable salt, prodrug, metabolite, analog or derivative thereof, acts selectively to modulate one molecular target (e.g., E2F-1) but does not significantly modulate another molecular target (e.g., Protein Kinase C). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

The polymer-modified therapeutic agents of the inventions may be combined with one or more additional therapeutic agents when used as a therapeutic treatment. In one embodiment, where the polymer-modified therapeutic has anti-tumor or anti-cancer activity, such as in the case of β-lapachone compounds, the polymer-modified therapeutic agent may be advantageously combined with one or more additional chemotherapeutic agents (second anti-cancer agents) useful in the treatment of cancer. The second chemotherapeutic agent can be a taxane, an aromatase inhibitor, an anthracycline, a microtubule targeting drug, a topoisomerase poison drug, a targeted monoclonal or polyconal antibody, an inhibitor of a molecular target or enzyme (e.g., a kinase inhibitor), or a cytidine analogue drug. In preferred aspects, the chemotherapeutic agent can be, but not restricted to, tamoxifen, raloxifene, anastrozole, exemestane, letrozole, HERCEPTIN® (trastuzumab), GLEEVEC® (imatanib), TAXOL® (paclitaxel), cyclophosphamide, lovastatin, minosine, araC, 5-fluorouracil (5-FU), methotrexate (MTX), TAXOTERE® (docetaxel), ZOLADEX® (goserelin), vincristin, vinblastin, nocodazole, teniposide, etoposide, GEMZAR® (gemcitabine), epothilone, navelbine, camptothecin, daunonibicin, dactinomycin, mitoxantrone, amsacrine, doxorubicin (adriamycin), epirubicin or idarubicin or agents listed in www.cancer.org/docroot/cdg/cdg_0.asp. In another aspect, the second chemotherapeutic agent can be a cytokine such as G-CSF (granulocyte colony stimulating factor). In some embodiments of the invention, the therapeutic agents and methods of treatment encompassed by this invention may comprise administration of a quinone-containing or carbonyl-containing therapeutic agent in both polymer conjugated and unconjugated forms. In another embodiment, a polymer-modified therapeutic agent of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone). In yet another embodiment, a polymer-modified therapeutic agent of the present invention, or a pharmaceutically acceptable salt, prodrug, metabolite, analog or derivative thereof, may be administered in combination with radiation therapy. The skilled artisan will recognize that a variety of other therapeutic agents in addition to those recited above may be administered in combination with the polymer-modified therapeutic agents of the present invention, and that they may act to augment or synergistically enhance the activity of polymer-modified therapeutic agents such as the polymer-modified β-lapachone compounds of the invention.

The polymer-modified therapeutic agents of the present invention when administered in combination with another therapeutic agent may be delivered in a unitary dosage form, or in separate dosage forms intended for simultaneous or sequential administration to a patient in need of treatment. When administered sequentially, the combination may be administered in two or more administrations. In an alternative embodiment, it is possible to administer one or more polymer-modified therapeutic agents of the present invention and one or more additional active ingredients by different routes. According to the methods of the invention, the combination of active ingredients may be (1) co-formulated and administered or delivered simultaneously in a combined formulation, (2) delivered by alternation or in parallel as separate formulations, or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

G. PHARMACEUTICAL COMPOSITIONS OF THE INVENTION

While it is possible for the polymer-modified therapeutic agents of the present invention, including the polymer-modified β-lapachone compounds of the present invention, to be administered without admixture or dilution, it may be preferable to formulate the compounds as pharmaceutical compositions. As such, pharmaceutical compositions comprising the polymer-modified therapeutic agents of the invention are provided. These pharmaceutical compositions are useful in the methods of the invention, including but not limited to treatment of various cancers and enhancing the accumulation of chemotherapeutic agents, such as β-lapachone or an analog thereof, in a tumor tissue. The pharmaceutical compositions of the invention may be formulated with pharmaceutically acceptable excipients such as carriers, solvents (including water or saline), stabilizers, adjuvants, diluents, etc., depending upon the particular mode of administration and dosage form. The pharmaceutical compositions should generally be formulated to achieve a physiologically compatible pH, and may range from a pH of about 5 to a pH of about 9, or more preferably from about pH 6 to about pH 8 depending on the formulation and route of administration. In alternative embodiments, it may be preferred that the pH is adjusted to a range from about pH 5.5 to about pH 7.5 or from about 6.5 to 8.5.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences). Suitable excipients include, but are not limited to, carrier molecules that include large, slowly metabolized macromolecules such as proteins, polysaccharides, polylactic acids, polyglycolic acids, polymeric amino acids, amino acid copolymers, polyethylene glycols (e.g., PEG 400) and inactive virus particles. Other exemplary excipients include antioxidants such as ascorbic acid; chelating agents such as EDTA, carbohydrates such as dextrin, hydroxyalkylcellulose, hydroxyalkylmethylcellulose, liquids such as oils, water, saline, glycerol wetting or emulsifying agents; pH buffering substances; and the like. Liposomes are also included within the definition of pharmaceutically acceptable excipients.

The pharmaceutical compositions of the invention comprise a therapeutically effective amount of at least one polymer conjugate, together with one or more pharmaceutically acceptable excipients. In a preferred embodiment, comprising polymer conjugates capable of delivering β-lapachone, or a derivative or analog thereof, or a pharmaceutically acceptable salt thereof, or a metabolite thereof, the compositions preferably maintain a plasma concentration of unconjugated β-lapachone from approximately 0.1 µg/ml to approximately 100 µg/ml, preferably from approximately 0.1 µg/ml to approximately 50 µg/ml, more preferably the unconjugated therapeutics will have an initial target plasma concentration from approximately 1 µg/ml to approximately 25 µg/ml. In another aspect, the pharmaceutical composition can maintain a suitable plasma concentration of β-lapachone for at least a month, at least a week, at least 24 hours, at least 12 hrs, at least 6 hrs, at least 1 hour. In a further aspect, a suitable plasma concentration of β-lapachone can be maintained indefinitely by the administration of periodic or continuous does of a suitable polymer conjugate. In yet another aspect, the subject can be exposed to the pharmaceutical composition in a AUC (area under the curve) range of about 0.5 µM-hr to about 100 µM-hr, about 0.5 µM-hr to about 50 µM-hr, about 1 µM-hr to about 25 µM-hr, about 1 µM-hr to about 10 µM-hr; about 1.25 µM-hr to about 6.75 µM-hr, about 1.5 µM-hr to about 6.5 µM-hr, where the concentration represents the total concentration of β-lapachone, or a derivative or analog thereof, or a pharmaceutically acceptable salt thereof, or a metabolite thereof. The pharmaceutical composition of suitable polymer conjugate, or a derivative or analog thereof, or a pharmaceutically acceptable salt thereof, or a metabolite thereof can be administered at a dosage from about 2 mg/m$^2$ to 5000 mg/m$^2$ per day, more preferably from about 20 mg/m$^2$ to 2000 mg/m$^2$ per day, more preferably from about 20 mg/m$^2$ to 500 mg/m$^2$ per day, most preferably from about 30 to 300 mg/m$^2$ per day. Preferably, 2 mg/m$^2$ to 5000 mg/m$^2$ per day is the administered dosage for a human. In another aspect, the pharmaceutical composition can be administered at a dosage from about 0.001 to 100 mg of β-lapachone, or a derivative or analog thereof, or a pharmaceutically acceptable salt thereof, or a metabolite thereof per kilogram body weight of recipient per day; preferably about 0.01 to 50 mg per kilogram body weight of recipient per day, more preferably from about 0.1 to 25 mg per kilogram body weight of recipient per day, most preferably from about 1 to 15 mg per kilogram body weight of recipient per day. One of ordinary skill in the art can determine the appropriate dosage amount in mg/m$^2$ per day or mg per kilogram body weight of recipient per day depending on subject to which the pharmaceutical composition is to be administered. Pharmaceutical compositions of the invention capable of delivering β-lapachone, or a derivative or analog thereof, or a pharmaceutically acceptable salt thereof, or a metabolite thereof at the above-indicated ranges may be prepared from polymer conjugated therapeutics. Where the pharmaceutical compositions of the invention comprise a combination of polymer-modified therapeutic, such as a β-lapachone compound, and a second therapeutic agent, such as a chemotherapeutic useful in the treatment of cancer, the therapeutic amounts of the second agents are may be generally known in the art or may be determined by the skilled clinician.

Some properties of polymer-modified β-lapachone compositions are provided in Table 1.

TABLE 1

| Conjugate | Sample | PGA (kD) (Sodium Salt) | Loading by Wt. (%) | Loading by Wt. (%) UV (305 nm) | Free β-lapachone by Wt. (%) (HPLC) | Salt Form |
|---|---|---|---|---|---|---|
| [structure] | A | 17.1 | 16.8 ± 0.6 | N/A | N/A | Sodium salt |

TABLE 1-continued

| Conjugate | Sample | PGA (kD) (Sodium Salt) | Loading by Wt. (%) | Loading by Wt. (%) UV (305 nm) | Free β-lapachone by Wt. (%) (HPLC) | Salt Form |
|---|---|---|---|---|---|---|
| (structure: β-lapachone-OAc with glycine-PGA ester) | B | 17.1 | 19.3 ± 0.3 | N/A | 0.4–0.58 | Free acid |
| | C | 17.1 | 25.5 ± 1.9 | 28.8 ± 0.34 | 0.1 | Free acid |
| | D | 56 | 18.6 ± 2.0 | 25.0 ± 0.4 | 0.4 | Free acid |
| | E | 56 | 32.8 ± 1.2 | 34.5 ± 0.5 | 0.3 | Free acid |
| | F | 56 | 31.9 ± 1.6 | 30.0 ± 0.7 | 0.1 | Free acid |
| | G | 56 | 33.1 ± 0.2 | 33.6 ± 0.4 | 0.4 | Free acid |
| | H | 56 | 36.1 ± 1.9 | 36.6 ± 1.4 | 0.5 | Free acid |
| | I | 56 | 37.1 ± 0.8 | 38.5 ± 1.2 | 0.4 | Free acid |
| (structure: β-lapachone dioxolane with CH2-O-PGA) | J | 7.1 | 16.2 ± 0.1 | N/A | N/A | Sodium salt |
| | K | 56 | 15.3 ± 0.7 | N/A | N/A | Sodium salt |

N/A is not available

The pharmaceutical compositions of the invention may be formulated in any form suitable for the intended method of administration. Preferred formulations of the present invention are those for parenteral administration, and in particular intravenous administration. Such pharmaceutical compositions include liquid solutions, emulsions, or suspensions. In a more preferred embodiment, pharmaceutical compositions of the invention may also be formulated as a lyophilized solid, which provides a convenient stable form that is reconstituted with a physiologically compatible solvent, such as water or saline, prior to administration either parenterally or by any other suitable route.

In other embodiments, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Where routes of administration such as oral, ocular rectal, buccal, topical, nasal, subcutaneous or and intramuscular are deemed to be desirable, pharmaceutical compositions of the invention may be formulated as syrups, creams, ointments, tablets, and the like employing suitable pharmaceutical excipients known in the art.

All publications mentioned in the above specification are herein incorporated by reference. The above description and drawings are illustrative of preferred embodiments of the present invention. It is not intended that the present invention be limited to the illustrative embodiments. Any modification of the present invention within the spirit and scope of this disclosure should be considered a part of the present invention.

To assist in understanding the present invention, the following Examples are included.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of 2-{[(9H-fluoren-9-ylmethoxy)carbonyl]amino}ethyl 4-nitrobenzoate

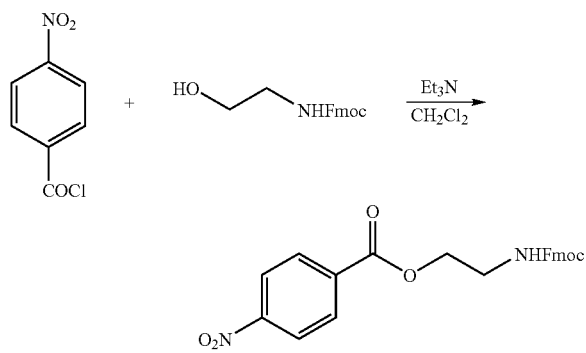

To a solution of 4-nitrobenzoylchloride (4.0 g, 21.6 mmoles) and N-(9-fluorenyl-methoxycarbonyl)ethanolamine (7.3 g, 25.9 mmoles) in 160 ml of methylene chloride is added triethylamine (3.1 ml, 22.6 mmoles). The mixture is stirred at room temperature for one hour, then is diluted with 400 ml of methylene chloride. The organic solution is washed with two portions of 200 ml of water and one portion of 200 ml of a saturated aqueous solution of sodium chloride. The organic phase is dried with $Na_2SO_4$, filtered and concentrated in vacuo. The resulting pale yellow solid is triturated in ethyl acetate. Filtration afforded 7.347 g of the title compound (79%). 400 MHz $^1$H NMR (DMSO-$d_6$) δ: 8.32 (d, J=8.4 Hz, 2H), 8.20 (d, J=8.8 Hz, 2H), 7.87 (d, J=7.3 Hz, 2H), 7.66 (d, J=7.3 Hz, 2H), 7.61 (t, J=5.7 Hz, 1H), 7.39 (t, J=7.5 Hz, 2H), 7.28 (t, J=7.5 Hz, 2H), 4.4-4.3 (m, 4H), 4.20 (t, J=6.8 Hz, 1H), 3.45-3.35 (m, 2H). LCMS: 433 [M+H].

Example 2

Preparation of 2-{[(9H-fluoren-9-ylmethoxy)carbonyl]amino}ethyl 4-aminobenzoate

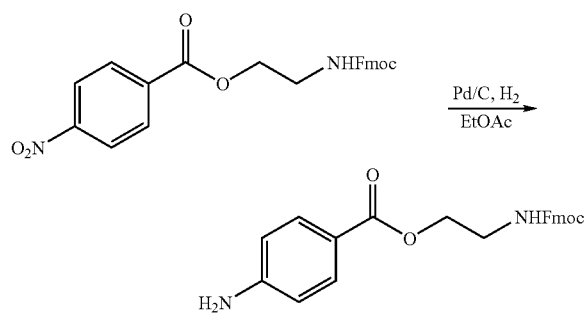

A solution of 2-{[(9H-fluoren-9-ylmethoxy)carbonyl]amino}ethyl 4-nitrobenzoate (7.47 g, 17 mmoles) in 1 liter of ethyl acetate, containing 1.5 g of 10% Pd on carbon (wet) is evacuated and filled with $H_2$ twice. The mixture is subjected to hydrogen at 1 atmosphere of pressure for two hours. The catalyst is filtered off on a Celite pad and the solution is concentrated in vacuo, yielding a yellow oil. Purification on silica gel using a gradient of 30-45% ethyl acetate in hexanes provided 5.436 g (80%) of the title compound as a white solid. 400 MHz $^1$H NMR (CDCl$_3$) δ: 7.86 (d, J=8.4 Hz, 2H), 7.75 (d, J=7.3 Hz, 2H), 7.58 (d, J=7.3 Hz, 2H), 7.39 (t, J=7.3 Hz, 2H), 7.30 (t, J=7.5 Hz, 1H), 6.64 (d, J=8.4 Hz, 2H), 5.13 (br. t, 1H), 4.40 (d, J=7.0 Hz, 2H), 4.36 (t, J=5.1 Hz, 2H), 4.22 (t, J=7.0 Hz, 1H), 4.1-4.0 (br. s, 2H), 3.65-3.55 (m, 2H). LCMS: 403 [M+H].

Example 3

Preparation of 2-{[(9H-fluoren-9-ylmethoxy)carbonyl]amino}ethyl 4-{[(6Z)-2,2-dimethyl-5-oxo-3,4-dihydro-2H-benzo[h]chromen-6 (5H)-ylidene]amino}benzoate

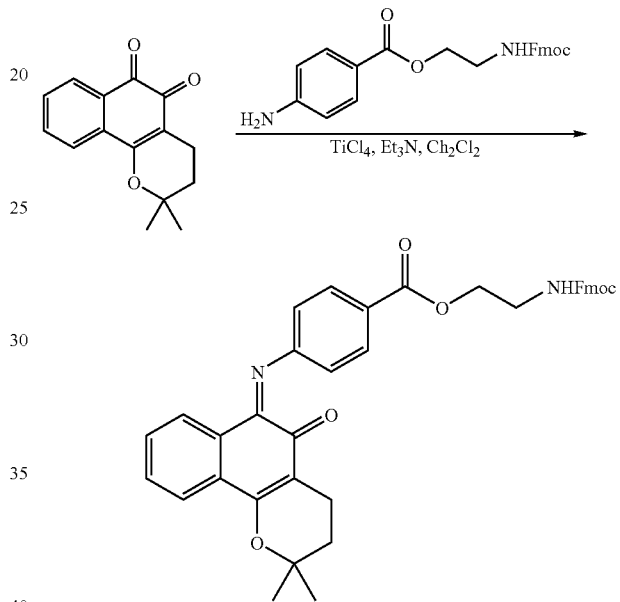

A solution of 2,2-dimethyl-3,4-dihydro-2H-benzo[h]chromene-5,6-dione (2.975 g, 12.3 mmoles) in 120 ml of methylene chloride is treated with 6.14 ml of a 1.0 M solution of TiCl$_4$ in methylene chloride. The mixture is stirred at room temperature for 5 minutes, then a solution of 2-{[(9H-fluoren-9-ylmethoxy)carbonyl]amino}ethyl 4-aminobenzoate (5.436 g, 13.5 mmoles) in 60 ml of methylene chloride is introduced followed by triethylamine (10.3 ml, 73.7 mmoles). The mixture is stirred at room temperature for 10 minutes. A second portion of 6.14 ml of a 1.0 M solution of TiCl$_4$ in methylene chloride is added and the mixture is stirred at room temperature for 10 minutes. A third portion of 6.14 ml of a 1.0 M solution of TiCl$_4$ in methylene chloride is added and the mixture is stirred at room temperature for 15 minutes. After stirring with the third aliquot of TiCl$_4$, the mixture is poured onto 300 ml of ice, to form a mixture having a precipitate. The mixture is filtered to remove the precipitate and the organic and aqueous phases are then separated. The aqueous phase is extracted with two portions of 200 ml of methylene chloride. The combined organic extracts are dried with Na$_2$SO$_4$, filtered and concentrated in vacuo, giving a brown oil. Purification on silica gel using a gradient of 0-10% ethyl acetate in methylene chloride provided a brown reddish foam, which is triturated in diethyl ether, yielding 990 mg (13%) of the title compound as a brown solid. M.p.: 163-164° C. 400 MHz $^1$H NMR (DMSO-$d_6$) δ: 8.13 (d, J=7.3 Hz, 1H), 7.93 (d, J=8.4 Hz, 2H), 7.88 (d, J=7.7 Hz, 2H), 7.82 (d, J=8.1 Hz, 1H), 7.7-7.55 (m, 5H), 7.40 (t, J=7.5 Hz, 2H), 7.30 (t, J=7.5 Hz, 2H), 6.79 (d, J=8.4 Hz, 2H), 4.33 (d, J=7.0 Hz, 2H), 4.3-4.2 (m, 3H), 3.45-3.35 (m, 2H), 2.25 (t, J=6.4 Hz, 2H), 1.79 (t, J=6.4 Hz, 2H), 1.41 (s, 6H). LCMS: 627 [M+H]. Calc. for $C_{39}H_{34}N_2O_6 \cdot 0.1$ water: C, 74.46; H, 5.48; N, 4.46; Found C, 74.48; H, 5.06; N, 4.43.

Example 4

Preparation of N-{2-[(4-{[(6Z)-2,2-dimethyl-5-oxo-3,4-dihydro-2H-benzo[h]-chromen-6 (5H)-ylidene]amino}benzoyl)oxy]ethyl} γ-poly-L-glutamate

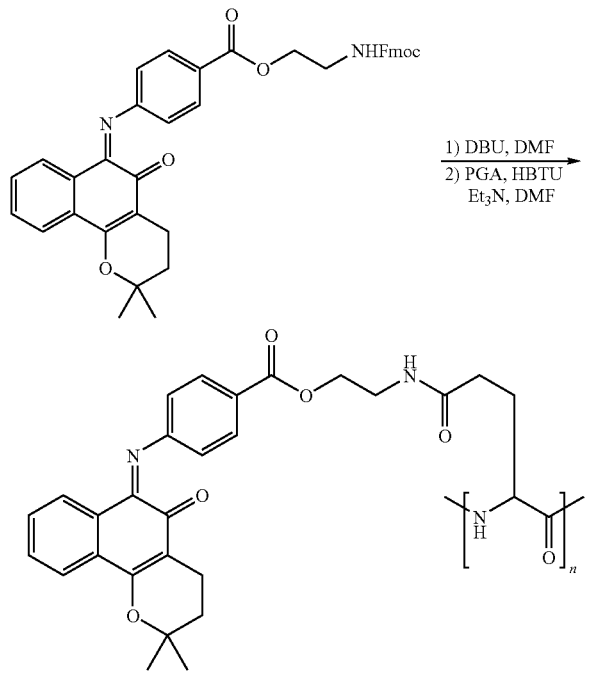

A solution of 2-{[(9H-fluoren-9-ylmethoxy)carbonyl]amino}ethyl 4-{[(6Z)-2,2-dimethyl-5-oxo-3,4-dihydro-2H-benzo[h]chromen-6 (5H)-ylidene]amino}benzoate (150 mg, 0.239 mmoles) in 7 ml of DMF is treated with 1,8-diazabicyclo[5.4.0]undec-7-ene (DBU) (150 µl, 1 mmole). The mixture is stirred at room temperature for two hours. The mixture is then diluted with 5 ml of DMF and polyglutamic acid (17,000 Da) is added (309 mg, 2.3 mmole) followed by triethylamine (333 µl, 2.3 mmoles) and HBTU (907 mg, 2.3 mmoles). The mixture is stirred at room temperature overnight. The mixture is poured into 100 ml of a 0.5 M aqueous solution of sodium bicarbonate, stirred for 30 minutes, then filtered. The solution is freeze-dried and the resulting solid is submitted to dialysis using molecular membrane against 3 changes of water. The dialyzed solution is freeze-dried to yield 78 mg of a dark brown solid. The quantity of 2,2-dimethyl-3,4-dihydro-2H-benzo[h]chromene-5,6-dione bound to polyglutamic acid is determined by release of 2,2-dimethyl-3,4-dihydro-2H-benzo[h]chromene-5,6-dione using 0.1 N HCl and UV detection to be 16.9% by weight based upon the weight of polymer conjugate hydrolyzed.

Example 5a

Synthesis of 5-(acetyloxy)-2,2-dimethyl-3,4-dihydro-2H-benzo[h]chromen-6-yl N-(tert-butoxycarbonyl)glycinate

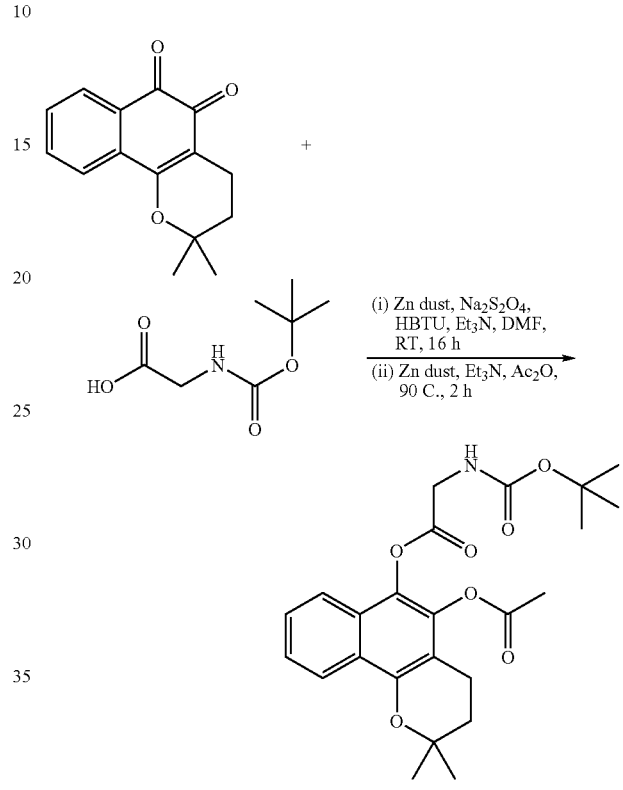

A mixture of zinc dust (6.0 g, 91.7 mmol), 2,2-dimethyl-3,4-dihydro-2H-benzo[h]chromene-5,6-dione (6.0 g, 24.8 mmol), $Na_2S_2O_4$ (17.26 g, 99.1 mmol), N-(tert-butoxycarbonyl)glycine (8.77 g, 49.6 mmol), triethylamine (3.1 ml, 22.3 mmol), HBTU (18.79 g, 49.6 mmol), and DMF (100 ml) is stirred for 16 hours at room temperature. To the reaction mixture is then added ethyl acetate (300 ml). The reaction is filtered and the filtrate washed with $H_2O$ (4×200 ml). The organic extract is dried with $Na_2SO_4$, and concentrated under reduced pressure to yield a residue. The residue is dissolved in acetic anhydride (30 ml), zinc dust (3.0 g, 45.9 mmol) and triethylamine (3.35 ml, 24.0 mmol) are then added. The mixture is heated to 90° C. with vigorous stirring and held at 90° C. for 2 hours, after which it is allowed to cool and the solvent is removed under reduced pressure to yield a second residue. The second residue is dissolved in ethyl acetate (200 ml) and washed with water (2×100 ml). The organic extract is dried with $Na_2SO_4$ and concentrated under reduced pressure to yield unrefined product. The unrefined product is purified by flash column chromatography on silica, eluting with 2% ethyl acetate in dichloromethane, to afford product about 60% pure. The product is further purified by crystallization from ethyl acetate/hexane, which gives the desired product as pure white solid (3.2 g, 31%). M.p.=177° C.; 400 MHz $^1$H NMR (CDCl$_3$) δ: 8.21 (d, J=8.4 Hz, 1H), 7.67 (d, J=8.4 Hz, 1H), 7.46 (m, 2H), 5.13 (br. s, 1H), 4.30 (d, J=5.6 Hz, 2H), 2.68 (t, J=6.6 Hz, 2H), 2.38 (s, 3H), 1.87 (t, J=6.6 Hz, 2H), 1.48 (s, 9H), 1.42 (s, 6H); LCMS: 444 [M+H]; Calc. for $C_{24}H_{29}NO_7$: C, 64.94; H, 6.59; N, 3.16; Found C, 64.98; H, 6.51; N, 3.15.

Example 5b

Synthesis of 5-(acetyloxy)-2,2-dimethyl-3,4-dihydro-2H-benzo[h]chromen-6-yl N-(tert-butoxycarbonyl)glycinate (1)

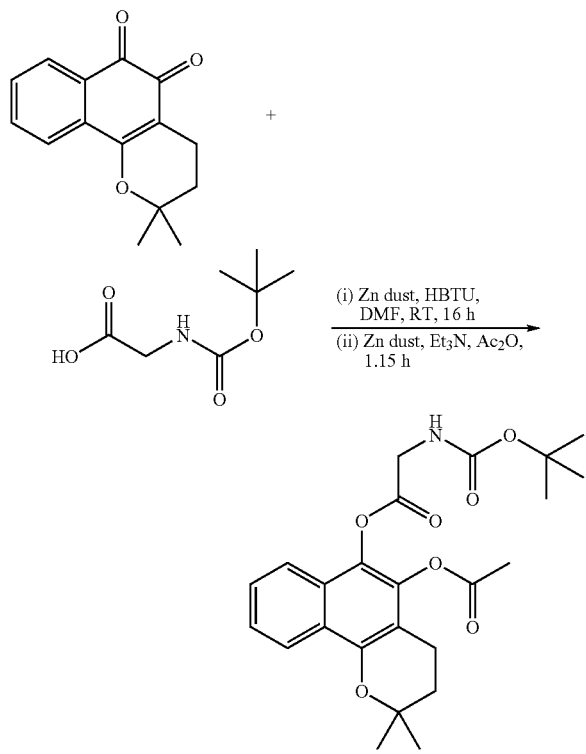

To a mixture of zinc dust (50.0 g, 0.765 mol) and 2,2-dimethyl-3,4-dihydro-2H-benzo[h]chromene-5,6-dione (50.0 g, 0.206 mol) is added DMF (500 mL). The mixture is allowed to stir for 15 min. To the reaction is then added a mixture of N-(tert-butoxycarbonyl) glycine (43.38 g, 0.247 mol) and HBTU (156.5 g, 0.413 mol) in 5 small portions over a period of 3 hours to control the exothermic reaction. The reaction was stirred for 16 hours. Ethyl acetate (EtOAc) (1300 mL) is then added, and the reaction is filtered through celite. The celite is bed washed with EtOAc (200 mL). The combined EtOAc solutions are washed with water (2×1000 mL) followed by saturated NaCl (500 mL). The organic layer is dried over sodium sulfate and concentrated under reduced pressure. The crude residue (103 g) is dissolved in acetic anhydride (150 mL) followed by the addition of zinc dust (13.5 g, 0.206 mol) and triethylamine (25.9 mL, 0.186 mol). The reaction is stirred for 1.15 hours. The solvent (acetic anhydride and triethylamine) is removed under reduced pressure to yield a residue. The residue was dissolved in EtOAc (1000 mL) and washed with water (2×500 mL), 5% sodium bicarbonate (2×500 mL) saturated NaCl (500 mL) and dried over $Na_2SO_4$. Concentration of the ethyl acetate solution under reduced pressure yields a yellowish white crude product (103 g) that is purified by crystallization from hexane-ethyl acetate. For crystallization, the crude product is dissolved in refluxing EtOAc (200 mL) and hexane (300 mL) is added. The mixture is allowed to cool to room temperature and stirred for 14 hr. A solid separated out which is collected by filtration and washed with 5% EtOAc in hexane (500 mL). The desired product (38.2 g) is obtained 98% pure with 2% of bis-glycine as a side-product. The 98% pure product (38.2 g) is again crystallized from refluxing EtOAc (165 mL) and hexanes (250 mL). The hot solution is allowed to cool to room temperature and stirred for 15 hr. The white solid obtained is filtered, washed with 5% EtOAc in hexane (400 mL), and dried under high vacuum at 45-50° C. The desired product (34.6 g, 38%) is obtained as a white solid at 99.83% purity based upon HPLC analysis. The $^1$H NMR is the same as described in Example 5a.

Example 6a

Synthesis of 5-(acetyloxy)-2,2-dimethyl-3,4-dihydro-2H-benzo[h]chromen-6-yl glycinate hydrochloride

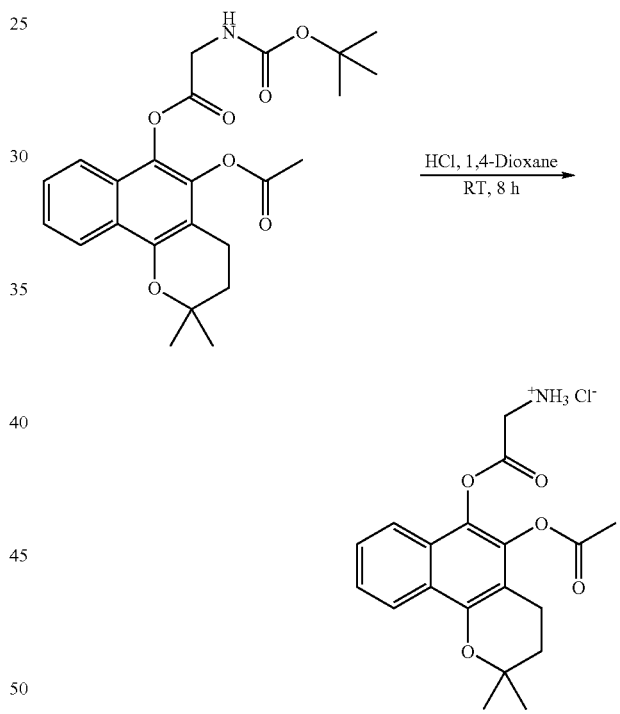

To a solution of 5-(acetyloxy)-2,2-dimethyl-3,4-dihydro-2H-benzo[h]chromen-6-yl N-(tert-butoxycarbonyl)glycinate (1) (2.35 g, 4.0 mmol) in 1,4-dioxane (25 ml) is added a solution of hydrogen chloride gas in anhydrous 1,4-dioxane (4.0 M, 60 ml). The reaction is stirred at room temperature for 6 hours. Upon drying under reduced pressure, the product hydrochloride salt is obtained as a white solid (1.489 g, 95%). M.p.=176-178° C.; 400 MHz $^1$H NMR (DMSO-$d_6$) δ: 8.58 (br. s, 3H), 8.14 (m, 1H), 7.9 (m, 1H), 7.55 (m, 2H), 4.41 (s, 2H), 2.62 (t, J=6.6 Hz, 2H), 2.41 (s, 3H), 1.88 (t, J=6.6 Hz, 2H), 1.39 (s, 6H); LCMS: 344 [M+H]; Calc. for $C_{19}H_{21}NO_5$·1.25 HCl: C, 58.62; H, 5.77; N, 3.6; Found C, 58.7; H, 5.72; N, 3.47.

Example 6b

Synthesis of 5-(acetyloxy)-2,2-dimethyl-3,4-dihydro-2H-benzo[h]chromen-6-yl glycinate hydrochloride

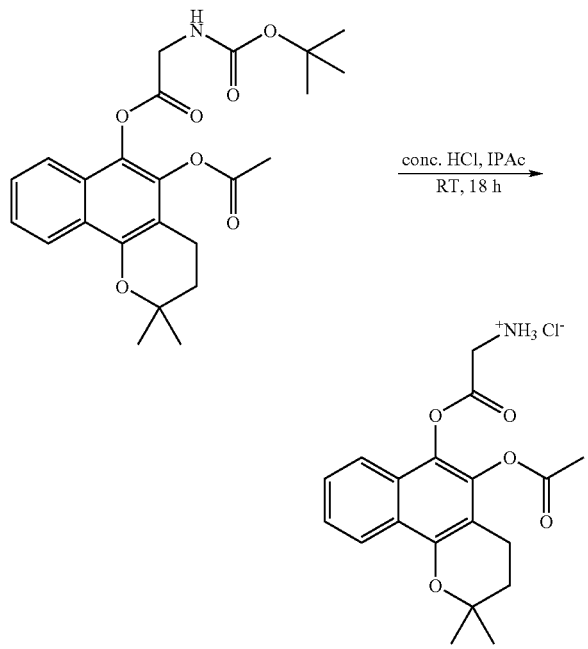

To a solution of 5-(acetyloxy)-2,2-dimethyl-3,4-dihydro-2H-benzo[h]chromen-6-yl N-(tert-butoxycarbonyl)glycinate (34.0 g, 76.6 mmol) in isopropyl acetate (150 mL) is added concentrated hydrochloric acid (28.0 ml, 37% by weight, 12.1 M). The reaction is stirred at room temperature for 18 hours. The solid is collected by filtration, washed with isopropyl acetate (4×100 mL) and dried under high vacuum. The product is obtained as an off-white solid (21.0 g, 73%) M.p.=190-193° C.; 400 MHz $^1$H NMR (DMSO-$d_6$) δ: 8.76 (br. s, 3H), 8.14-8.11 (1H, m), 7.95-7.92 (1H, m), 7.60-7.50 (2H, m), 4.39 (2H, s), 2.63 (2H, t, J=6.4 Hz), 2.43 (3H, s), 1.87 (2H, t, J=6.4 Hz), 1.39 (6H, s); LCMS: 344 [M+H]; Calc. for $C_{19}H_{21}NO_5 \cdot 1.07$ HCl: C, 59.68; H, 5.83; N, 3.69; Found C, 59.66; H, 5.83; N, 3.69.

Example 7a

Synthesis of 5-(acetyloxy)-2,2-dimethyl-3,4-dihydro-2H-benzo[h]chromen-6-yl glycinate γ-poly-L-glutamate

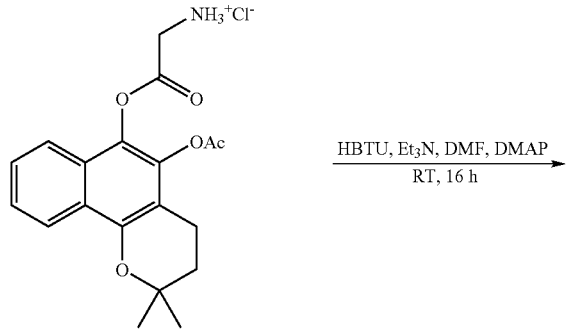

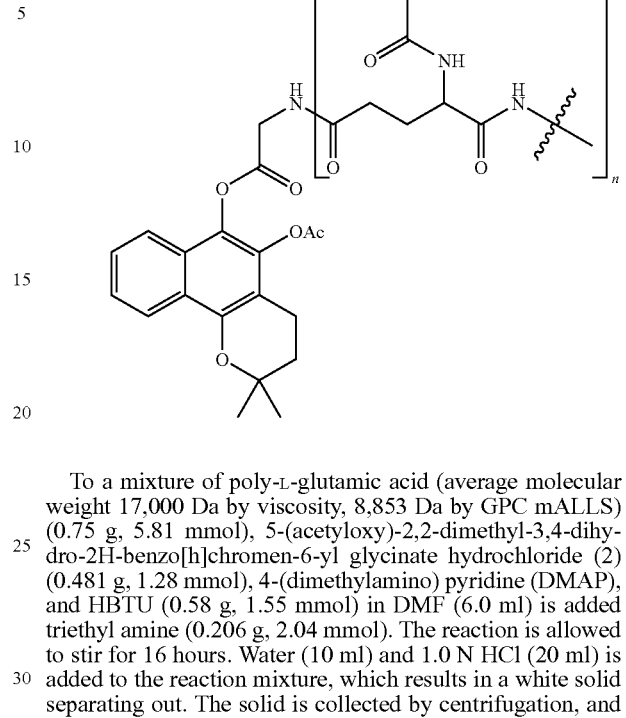

To a mixture of poly-L-glutamic acid (average molecular weight 17,000 Da by viscosity, 8,853 Da by GPC mALLS) (0.75 g, 5.81 mmol), 5-(acetyloxy)-2,2-dimethyl-3,4-dihydro-2H-benzo[h]chromen-6-yl glycinate hydrochloride (2) (0.481 g, 1.28 mmol), 4-(dimethylamino) pyridine (DMAP), and HBTU (0.58 g, 1.55 mmol) in DMF (6.0 ml) is added triethyl amine (0.206 g, 2.04 mmol). The reaction is allowed to stir for 16 hours. Water (10 ml) and 1.0 N HCl (20 ml) is added to the reaction mixture, which results in a white solid separating out. The solid is collected by centrifugation, and the supernatant discarded. The solid is washed 5 times with 1.0 N HCl (40 ml) and then with 5 times with deionized water (40 ml), or until the pH of solution is between 4 and 4.5. The solid is then suspended in 20 ml of water and lyophilized to dryness, yielding a white powder (0.885 g, 76%). The quantity of 2,2-dimethyl-3,4-dihydro-2H-benzo[h]chromene-5,6-dione bound to the polymer is calculated by releasing 2,2-dimethyl-3,4-dihydro-2H-benzo[h]chromene-5,6-dione from the conjugate by treatment with 0.01 N NaOH (18.6+/−0.6% by weight based upon the weight of the polymer conjugate hydrolyzed). 400 MHz $^1$H NMR (DMSO-$d_6$) δ: 12.1 (br. s, 1.81H), 8.6-8.4 (br. s, 1H), 8.4-7.9 (br s, 3.5H), 7.9-7.65 (br s, 1H), 7.65-7.2 (br s, 2H), 4.4-3.8 (br m, 4.2H), 2.8-2.6 (br s, 3H), 2.5-1.6 (br m, 15H), 1.3 (br s, 6H). The quantity of 2,2-dimethyl-3,4-dihydro-2H-benzo[h]chromene-5,6-dione conjugated to the polymeric vehicle may be determined as described in Example 11

Example 7b

Synthesis of 5-(acetyloxy)-2,2-dimethyl-3,4-dihydro-2H-benzo[h]chromen-6-yl glycinate γ-poly-L-glutamate

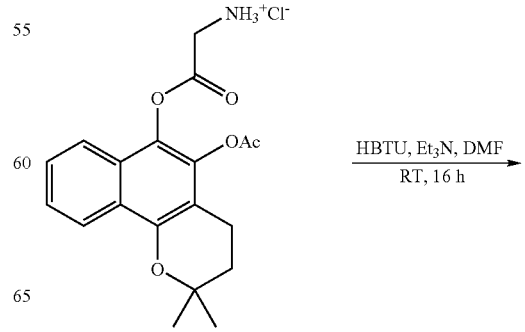

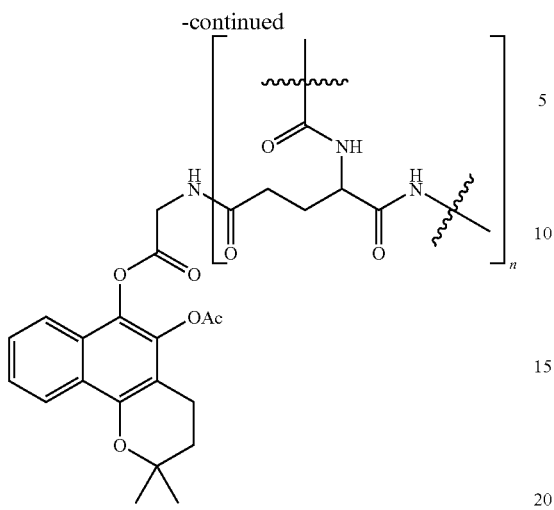

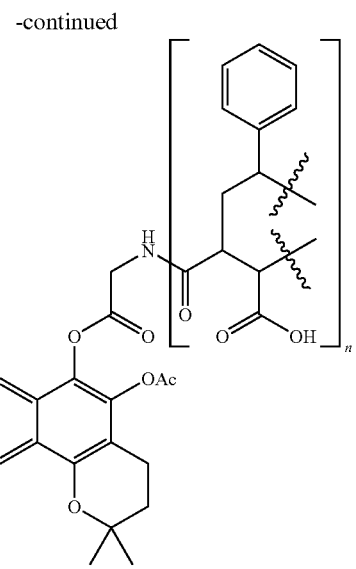

To poly-L-glutamic acid (average molecular weight: 47.9 kD by viscosity, 37.83 kD by GPC mALLS (multi-angle laser light scattering)) (1.0 g, 7.75 mmol) is added DMF (100 mL) and the suspension allowed to stir for 30 min. To the suspension is then added HBTU (0.7141 g, 1.88 mmol) and the reaction allowed to stir for 10 min. This is followed by the simultaneous addition of 5-(acetyloxy)-2,2-dimethyl-3,4-dihydro-2H-benzo[h]chromen-6-yl glycinate hydrochloride (2) (0.625 g, 1.64 mmol) and dimethylaminopyridine (0.20 g, 1.64 mmol); triethylamine (0.206 g, 2.04 mmol) is then added and the reaction is stirred for 16 hours. The solvent, including DMF, is then removed under reduced pressure to yield an oily residue, to which 1.0 N HCl (100 ml) is added resulting in a light yellow colored filament like solid separating out. The solid is collected by centrifugation and the supernatant discarded. The solid is washed 5 times with 1.0 N HCl (40 mL) and then washed 5 times with deionized water (40 mL) or until the pH of solution is between 4 and 4.5. The solid is frozen and lyophilized to dryness to yield a light yellow powder (1.12 g, 73%). Loading (18.6+/−2% by wt.) is calculated by releasing 2,2-dimethyl-3,4-dihydro-2H-benzo[h]chromene-5,6-dione from the conjugate by treatment with 0.01 N NaOH. 400 MHz $^1$H NMR (DMSO-$d_6$) δ: 12.1 (br. s, 2.3H), 8.6-8.4 (br. s, 0.5H), 8.3-7.9 (br s, 3.6H), 7.9-7.65 (br s, 1.4H), 7.65-7.2 (br s, 2.1H), 4.5-4.0 (br m, 5.2H), 2.7-2.5 (br s, 2.0H), 2.5-2.1 (br m, 9.2H), 2.1-1.6 (br m, 8.3H), 1.37 (br s, 6H). The quantity of 2,2-dimethyl-3,4-dihydro-2H-benzo[h]chromene-5,6-dione conjugated to the polymeric vehicle may be determined as described in Example 11

Example 8

Synthesis of 5-(acetyloxy)-2,2-dimethyl-3,4-dihydro-2H-benzo[h]chromen-6-yl glycinyl-poly(styrene-co-maleamide)

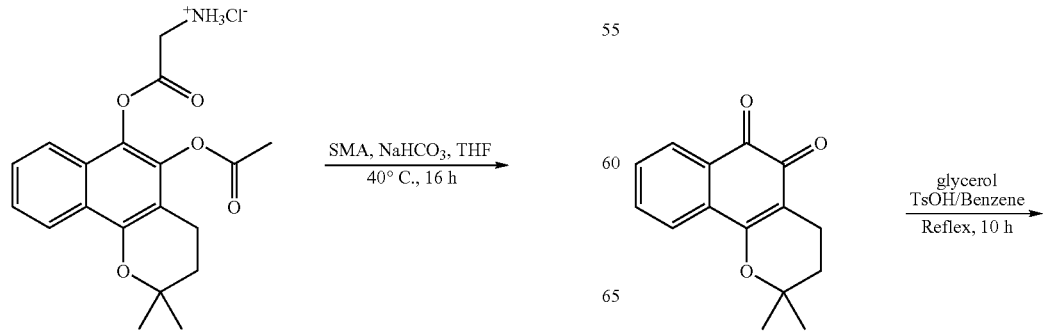

To a solution of styrene maleic anhydride (mol. wt. 1600 by GPC, 0.20 g, 0.86 mmol) in THF is added sodium bicarbonate (0.288 g, 3.42 mmol) followed by 5-(acetyloxy)-2,2-dimethyl-3,4-dihydro-2H-benzo[h]chromen-6-yl glycinate hydrochloride (0.423 g, 1.15 mmol). The reaction is allowed to stir for 16 hour at 40° C. The solvent is removed under reduced pressure to yield a residue, which is dissolved in dichloromethane (5 mL) and filtered through a plug of glass wool. To the clear dichloromethane filtrate is added diethyl ether (100 mL), which results in a light yellow solid separated out. The light yellow solid was filtered, washed with diethyl ether (50 mL), and dried under high vacuum to give the desired product (0.29 g, 52%). Loading (34-41% by wt.) is calculated by releasing 2,2-dimethyl-3,4-dihydro-2H-benzo[h]chromene-5,6-dione from the conjugate by treating it with 0.01 N NaOH. 400 MHz $^1$H NMR (DMSO-$d_6$) δ: 8.2-8.0 (br s, 1.2H), 8.0-7.7 (br s, 1H), 7.7-7.35 (br s, 1.56H), 7.3-6.4 (br s, 4.5H), 4.4-3.8 (br m, 1.76H), 2.8-2.0 (br m, 4.5H), 2.0-1.6 (br m, 2.9H), 1.5-1.1 (br m, 6H).

Example 9a

Preparation of 4'-(hydroxymethyl)-2,2-dimethyl-3,4-dihydro-2H,5H-spiro[benzo[h]chromene-6,2'-[1,3]dioxolan]-5-one -continued

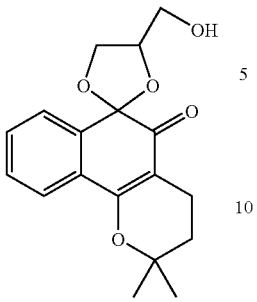

To a solution of 2,2-dimethyl-3,4-dihydro-2H-benzo[h]chromene-5,6-dione (1.21 g, 5 mmol) in benzene (12 ml) is added glycerol (0.92 g, 10 mmol) and p-toluenesulfonic acid monohydrate (0.28 g, 1.5 mmol). The resulting mixture is refluxed for 6 hours. After removal of the solvent, product is purified by column chromatography on silica gel eluting with 30% ethyl acetate in methylene chloride to provide 0.57 g (36% yield) as a light yellow solid, which is a mixture of diasteromers. M.p. 44-46° C.; 400 MHz $^1$H NMR (CDCl$_3$) δ: 1.41 (s, 6H), 1.73-1.82 (m, 2H), 2.36-2.42 (m, 1H), 2.48-2.54 (m, 1H), 3.72-3.78 (m, 1H), 4.18 (d, J=2.5 Hz, 1H), 4.20-4.29 (m, 1H), 4.40 (t, J=8.0 Hz, 1H), 4.71-4.74 (m, 1H), 4.85 (d, J=8.8 Hz, 1H), 7.38-7.44 (m, 2H), 7.54-7.56 (m, 1H), 7.75-7.78 (m, 1H); LCMS: Calc. for $C_{18}H_{21}O_5$: 217; Found 217.

Example 9b

Preparation of 4'-(azidomethyl)-2,2-dimethyl-3,4-dihydro-2H,5H-spiro[benzo[h]chromene-6,2'-[1,3]dioxolan]-5-one and its Conversion into 4'-(aminomethyl)-2,2-dimethyl-3,4-dihydro-2H,5H-spiro[benzo[h]chromene-6,2'-[1,3]dioxolan]-5-one Step 1. Synthesis of 4'-(azidomethyl)-2,2-dimethyl-3,4-dihydro-2H,5H-spiro[benzo[h]chromene-6,2'-[1,3]dioxolan]-5-one -continued

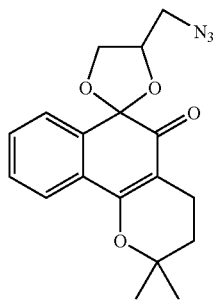

To a solution of 4'-(hydroxymethyl)-2,2-dimethyl-3,4-dihydro-2H,5H-spiro[benzo[h]chromene-6,2'-[1,3]dioxolan]-5-one (316 mg, 1.0 mmol) in dichloromethane (2 mL) is added methanesulfonyl chloride (0.095 mL, 1.3 mmol) and triethylamine (0.163 mL, 1.24 mmol). The mixture is stirred at room temperature for 2 hours. The reaction mixture is washed with water (2×1.0 mL), dried over sodium sulfate and concentrated to provide (2,2-dimethyl-5-oxo-3,4-dihydro-2H,5H-spiro[benzo[h]chromene-6,2'-[1,3]dioxolan]-4'-yl) methyl methanesulfonate as a white solid (99% by LC/MS, UV 254 nm). The (2,2-dimethyl-5-oxo-3,4-dihydro-2H,5H-spiro[benzo[h]chromene-6,2'-[1,3]dioxolan]-4'-yl)methyl methanesulfonate (197 mg, 0.5 mmol) is dissolved in DMF (2 mL) followed by the addition of sodium azide (97 mg, 1.5 mmol). The reaction is heated at 80° C. for 24 hour and 100° C. for 12 h. The mixture is diluted with CH$_2$Cl$_2$ (4 mL), washed with water (2 ml) and concentrated. The organic layer is dried with sodium sulfate, concentrated under reduced pressure and purified by flash column chromatography (SiO$_2$, 30% EtOAc in hexane) to provide 4'-(azidomethyl)-2,2-dimethyl-3,4-dihydro-2H,5H-spiro[benzo[h]chromene-6,2'-[1,3]dioxolan]-5-one (25 mg, 15%) as a white solid. 400 MHz $^1$H NMR (CDCl$_3$) δ: 7.78-7.56 (m, 1H), 7.60-7.57 (m, 1H), 7.44-7.40 (m, 2H), 4.68-4.62 (m, 1H), 4.46-4.42 (m, 1H), 4.23 (t, J=8 Hz, 1H). 3.96-3.91 (m, 1H), 3.54-3.49 (m, 1H), 2.48-2.42 (m, 2H), 1.79 (t, J=6.8 Hz, 2H), 1.42 (d, J=3.2 Hz, 6H); LCMS: 342 [M+H].

Step 2. Conversion of 4'-(azidomethyl)-2,2-dimethyl-3,4-dihydro-2H,5H-spiro[benzo[h]chromene-6,2'-[1,3]dioxolan]-5-one to 4'-(aminomethyl)-2,2-dimethyl-3,4-dihydro-2H,5H-spiro[benzo[h]chromene-6,2'-[1,3]dioxolan]-5-one

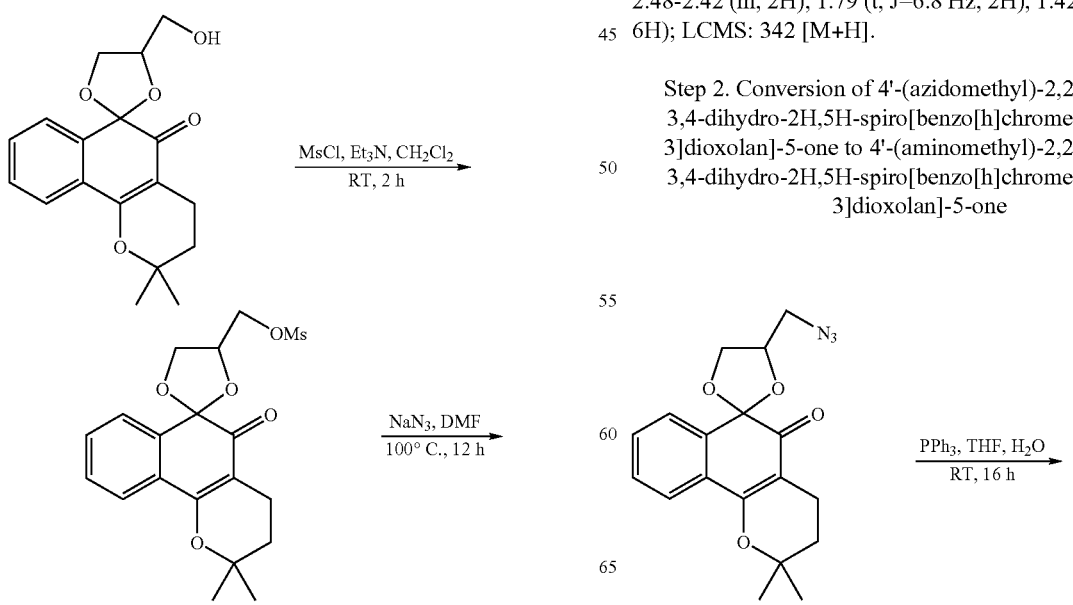

-continued

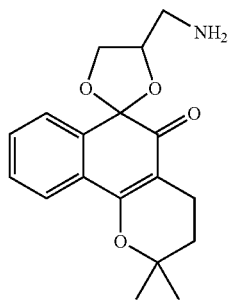

To a solution of 4'-(azidomethyl)-2,2-dimethyl-3,4-dihydro-2H,5H-spiro[benzo[h]chromene-6,2'-[1,3]dioxolan]-5-one (0.012 mg, 0.035 mmol) in THF (1.0 mL) is added triphenylphosphine (0.033 mg, 0.13 mmol). The mixture is stirred at room temperature for 3 hour followed by addition of water (50 μL). The reaction is then stirred for another 16 hour at room temperature and solvent is removed under reduce pressure to yield a reside of 4'-(aminomethyl)-2,2-dimethyl-3,4-dihydro-2H,5H-spiro[benzo[h]chromene-6,2'-[1,3]dioxolan]-5-one as confirmed by LC/MS, which indicates the product, which has a molecular weight of 315 Da, is present in the crude residue along with triphenylphosphine oxide (a side product from the triphenylphosphine).

Example 10

Preparation of (2,2-dimethyl-5-oxo-3,4-dihydro-2H,5H-spiro[benzo[h]chromene-6,2'-[1,3]dioxolan]-4'-yl)methyl γ-poly-L-glutamate sodium 0.20 mmol), 1,3-dicyclohexylcarbodiimide (144 mg, 0.70 mmol), and 4-dimethylaminopyridine (5 mg, 0.04 mmol). The mixture is stirred at room temperature overnight. The progress of the reaction may be monitored by HPLC for disappearance of the ketal linker conjugate. Typical HPLC conditions employ an Aligent Zorbax SB-C8 rapid resolution cartridge (30×4.6 mm, 3.5 μm) fitted with a Phenomenex C8 (Octyl, MOS) guard column (4.00×3.00 mm cartridge) with UV detection at 254 nm. The column is equilibrated at a flow rate of 3 ml/min in a mixture of 95% solvent A (water with 0.1% TFA) and 5% solvent B (acetonitrile with 0.1% TFA), after sample application, the solvent is changed to 5% solvent A and 95% solvent B at 0.25 minutes, after 4.1 minutes the column is returned to equilibration buffer (95% solvent A and 5% solvent B) for 4.8 minutes. When the ketal linker conjugate has been consumed, the resulting mixture is diluted with chloroform (10 ml) and a solution of 0.5 M sodium bicarbonate (15 ml) is added. The mixture is shaken well and subject to centrifugation. The chloroform layer is removed and the water layer is washed three times with 5 ml of chloroform in each wash. The resulting aqueous solution is dialyzed employing a 6000-8000 molecular weight cut-off dialysis membrane against deionized water. Dialysis employed six changes deionized water replaced at 4 hours intervals over 24 h. Lyophilization of the aqueous solution yielded 170 mg of product as a white soft solid. M.p. 265-268° C.

The quantity of ketal linked 2,2-dimethyl-3,4-dihydro-2H-benzo[h]chromene-5,6-dione (β-lapachone) associated with polyglutamic acid is determined by hydrolysis of the compound from the polymer followed by quantitation. To a solution of conjugate (1.4 mg) in water (0.3 ml) is added 50% NaOH (100 μl). The mixture is sonicated at room temperature for 5 minutes.

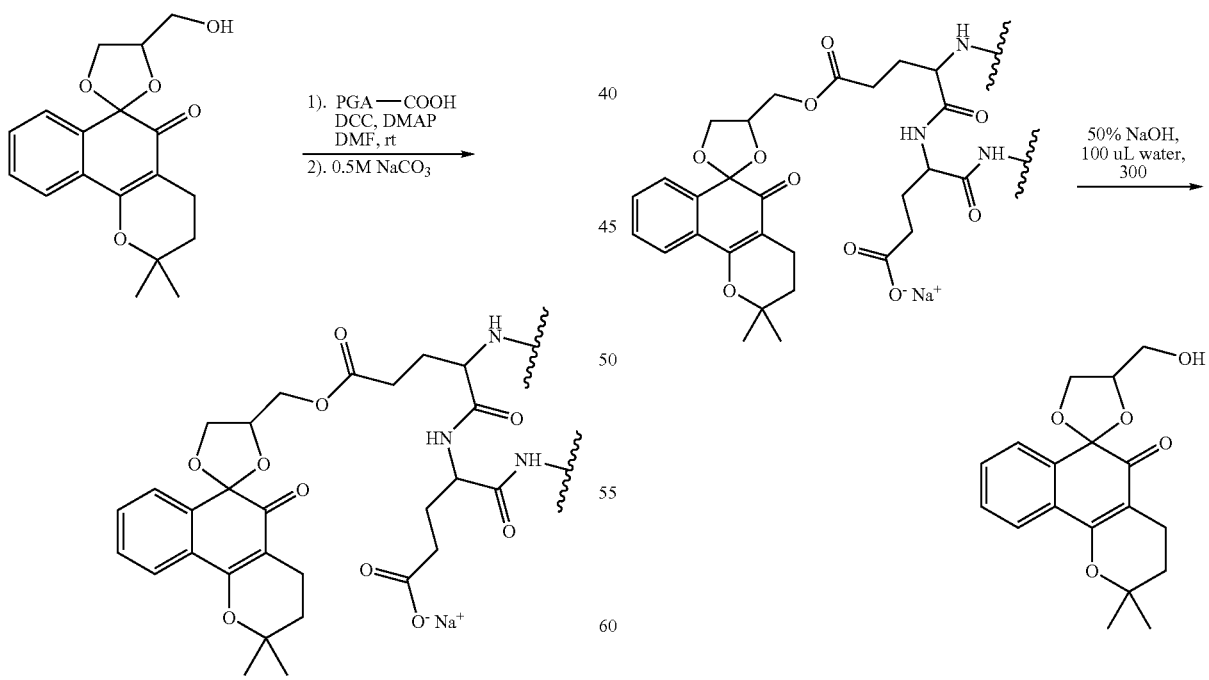

To a solution of poly-L-glutamic acid (Mw approximately 17,000 Da) (170 mg) in DMF (5 ml) is added the ketal linker conjugated 2,2-dimethyl-3,4-dihydro-2H-benzo[h]chromene-5,6-dione product prepared in Example 9a (63 mg, Product is extracted with ethyl acetate (1.0 ml×3). Organic extracts are combined and solvent is removed. The residue is dissolve in 1.0 ml DMSO. Released ketal linker conjugated therapeutic agent is determined by HPLC as described above. The quantity of 2,2-dimethyl-3,4-dihydro-2H-benzo[h]

chromene-5,6-dione bound to the polymer is calculated to be 18.5% by weight based upon the weight of the polymer conjugate hydrolyzed.

Alternatively, 2,2-dimethyl-3,4-dihydro-2H-benzo[h]chromene-5,6-dione (β-lapachone) is released from the PGA ketal conjugate in 1N HCl at 37° C.,

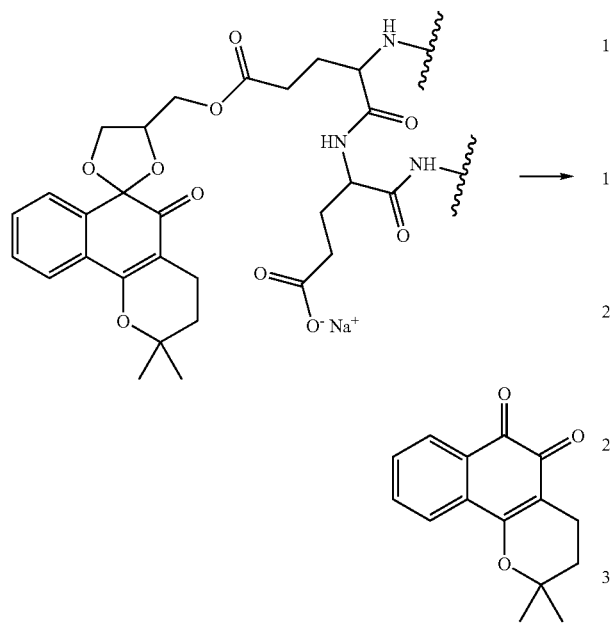

and the β-lapachone extracted with ethyl acetate. The ethyl acetate extracts are dried and the content of β-lapachone quantitated by HPLC as described above.

Alternative means of determining the quantity of ketal conjugated to polymeric vehicles is described in Example 11.

Example 11

Determination of the Quantity of 2,2-dimethyl-3,4-dihydro-2H-benzo[h]chromene-5,6-dione that is Conjugated to poly-L-glutamic acid Example 11(a)

5-(acetyloxy)-2,2-dimethyl-3,4-dihydro-2H-benzo[h]chromen-6-yl glycinate γ-poly-L-glutamate conjugate The conjugate is dissolved in a phosphate buffer adjusted to the final pH of 9.6 at a concentration of about 0.1 mg/ml. The complete release of 2,2-dimethyl-3,4-dihydro-2H-benzo[h]chromene-5,6-dione from the conjugate is achieved within 2-3 days as monitored by HPLC. In addition to the 2,2-dimethyl-3,4-dihydro-2H-benzo[h]chromene-5,6-dione peak, two additional peaks are detected in the HPLC chromatogram. These peaks are believed to be products of the degradation of 2,2-dimethyl-3,4-dihydro-2H-benzo[h]chromene-5,6-dione and an alternate hydrolysis product of conjugate. The concentration of released 2,2-dimethyl-3,4-dihydro-2H-benzo[h]chromene-5,6-dione is calculated by comparing the peak areas with the previously obtained calibration curve of 2,2-dimethyl-3,4-dihydro-2H-benzo[h]chromene-5,6-dione standard. The concentration of the 2,2-dimethyl-3,4-dihydro-2H-benzo[h]chromene-5,6-dione is then corrected for the degradation by taking into account the peak areas of the two degradation products (assuming they have identical extinction coefficients). Loading on the polymer is then calculated as follows:

% loading=mg of (2,2-dimethyl-3,4-dihydro-2H-benzo[h]chromene-5,6-dione)/mg of conjugate×100

Hydrolysis of the 2,2-dimethyl-3,4-dihydro-2H-benzo[h]chromene-5,6-dione from the conjugate proceeds faster at higher pH (20 min. at pH 11.4). However at this pH the degradation and the alternate hydrolysis products are generated at higher levels, which underestimates the actual loading on the conjugate Direct UV method Conjugates are dissolved in DMSO at a concentration of 0.1 mg/ml. The absorption of aliquots (250 μl) of the solution are analyzed for the absorbance at 305 nm with a Spectra MAX, 96 well plate UV spectrometer (Molecular Devices). The amount of (5-(acetyloxy)-2,2-dimethyl-3,4-dihydro-2H-benzo[h]chromen-6-yl glycinate hydrochloride) loaded on the polymer is determined from a calibration curve of (5-(acetyloxy)-2,2-dimethyl-3,4-dihydro-2H-benzo[h]chromen-6-yl glycinate hydrochloride) dissolved in DMSO. Both free and polymer bound 2,2-dimethyl-3,4-dihydro-2H-benzo[h]chromene-5,6-dione display an absorbance maximum at 305 nm. The loadings obtained from the direct UV method correlated well with those determined by hydrolysis conduted at pH=9.6.

Example 11(b)

N-{2-[(4-{[(6Z)-2,2-dimethyl-5-oxo-3,4-dihydro-2H-benzo[h]-chromen-6 (5H)-ylidene]amino}benzoyl)oxy]ethyl} γ-poly-L-glutamate The conjugate is dissolved in water at a concentration of about 0.3 mg/ml and sonicated to facilitate dissolution. Ten-fold dilution into 1 M HCl solution almost instantly facilitates the hydrolysis of 2,2-dimethyl-3,4-dihydro-2H-benzo[h]chromene-5,6-dione from the conjugate (~4 min treatment time). The concentration of released 2,2-dimethyl-3,4-dihydro-2H-benzo[h]chromene-5,6-dione is determined by HPLC and the quantity calculated by comparing the peak areas with a previously obtained calibration curve of 2,2-dimethyl-3,4-dihydro-2H-benzo[h]chromene-5,6-dione standard, as described above in Example 10. No additional degradation peaks were observed in the HPLC chromatogram and the loading on the polymer was then calculated as above.

Example 11(c)

(2,2-dimethyl-5-oxo-3,4-dihydro-2H,5H-spiro[benzo[h]chromene-6,2'-[1,3]dioxolan]-4'-yl)methyl γ-poly-L-glutamate sodium The conjugate is dissolved in 0.1 M NaOH solution at a concentration of about 1 mg/ml. Base treatment releases the 4'-(hydroxymethyl)-2,2-dimethyl-3,4-dihydro-2H,5H-spiro[benzo[h]chromene-6,2'-[1,3]dioxolan]-5-one (A) from the conjugate in about 20 min as determined by HPLC. The concentration of released 4'-(hydroxymethyl)-2,2-dimethyl-3,4-dihydro-2H,5H-spiro[benzo[h]chromene-6,2'-[1,3]dioxolan]-5-one (A) is calculated by comparing the peak areas with the previously obtained calibration curve of 4'-(hydroxymethyl)-2,2-dimethyl-3,4-dihydro-2H,5H-spiro[benzo[h]chromene-6,2'-[1,3]dioxolan]-5-one (A) standard. The loading is expressed in 2,2-dimethyl-3,4-dihydro-2H- benzo[h]chromene-5,6-dione (B) equivalents by factoring in the molecular weight difference:

mg of $B$ = mg of $A$ × (Mw of $B$)/(Mw of $A$)

% loading = mg of $B$/mg of conjugate × 100

Example 12

Cell Based Assays

Cell viability is determined by measuring the activity of dehydrogenase enzymes in metabolically active cells using a tetrazolium compound, MTS. The assay is performed as described in Promega Technical Bulletin No. 169 (CellTiter 96 Aqueous Non-Radioactive Cell Proliferation Assay). Two cell lines, DLD-1 and NCM-460 are assayed (see, e.g., Table 2). Cells are maintained at 37° C., 5% $CO_2$. Adherent cells are maintained DMEM media (4.5 g/L glucose) supplemented with 15% heat-inactivated FBS, 10 mM L-glutamine, and 10 mM Hepes pH 7.5. Suspension cells are maintained in RPMI 1640 media, supplemented with 10% heat-inactivated FBS and 10 mM Hepes pH 7.5. Briefly, cells are seeded in 96-well plates and incubated for 16-24 hours. Candidate compounds, including the polymer-modified therapeutics to be tested, are serially diluted in the indicated solvents are, further diluted in cell culture media, and then added to cells. Cells are incubated in the presence of candidate compound for 20 hours or 72 hours, as indicated. MTS stock solution (MTS 2 gm/L, PMS 46.6 mg/ml in PBS) is added to the cells (final concentration MTS 2 gm/L and PMS 7.67 mg/L) and incubated for 4 hours. SDS is added to a final concentration of 1.4% and absorbance at 490 nM is measured within two hours using a plate reader. The $IC_{50}$ is defined as the concentration of compound that results in a 50% reduction in the number of viable cells as compared to control wells treated with DMSO only (0.33%) and 0.3% SDS, and is calculated using non-linear regression analysis. The data is represented graphically in FIG. 1: Panels A-D, and the $IC_{50}$ values are given in Table 2.

TABLE 2

| COMPOUND (SOLVENT) | POLYMER MW (Da) LOADING (Weight %) | INCU-BATION TIME (Hours) | DLD-1 CELLS $IC_{50}$ (μM) | NCM-460 CELLS $IC_{50}$ (μM) |
|---|---|---|---|---|
| 2,2-dimethyl-3,4-dihydro-2H-benzo[h]chromene-5,6-dione (DMSO) | N.A. | 20 | 3.13 | 8.19 |
| 5-(acetyloxy)-2,2-dimethyl-3,4-dihydro-2H-benzo[h]chromen-6-yl glycinate γ-poly-L-glutamate (PEG/water) | 17,100 18.6 ± 0.6 | 20 | 4.42 | 8.12 |
| (2,2-dimethyl-5-oxo-3,4-dihydro-2H,5H-spiro[benzo[h]chromene-6,2'-[1,3]dioxolan]-4'-yl)methyl γ-poly-L-glutamate sodium (water) | 17,100 16.2 ± 0.1 | 20 | >100 | >100 |
| 2,2-dimethyl-3,4-dihydro-2H-benzo[h]chromene-5,6-dione (DMSO) | N.A. | 72 | 1.71 | 3.25 |
| 5-(acetyloxy)-2,2-dimethyl-3,4-dihydro-2H-benzo[h]chromen-6-yl glycinate γ-poly-L-glutamate (PEG/water) | 17,100 18.6 ± 0.6 | 72 | 1.39 | 3.66 |
| (2,2-dimethyl-5-oxo-3,4-dihydro-2H,5H-spiro[benzo[h]chromene-6,2'-[1,3]dioxolan]-4'-yl)methyl γ-poly-L-glutamate sodium (water) | 17,100 16.2 ± 0.1 | 72 | >100 | >100 |

N.A.: Not Applicable
PEG/water: is 20% polyethylene glycol 300 Mw and 80% water.

Example 13

Analyitical Determination of β-Lapachone Levels in Plasma

Chromatographic analysis of plasma samples to determine plasma β-Lapachone levels is conducted employing a Zorbax SB C8 HPLC column (2.1×30 mm, 5μ particle size). The chromatographic system employs a CTC PAL Leap autoinjector (Leap Technologies, Carrboro, N.C.) with an Agilent (Agilent Technologies, Palo Alto, Calif.) 1100 HPLC system interfaced to a Micromass Quattro Ultima (Waters Corporation, Milford, Mass., USA) triple quadrapole mass spectrometer is employed to analyze samples. Chromatographic separations were conducted employing a gradient formed from mobile phase A (0.1% formic acid (FA) in water) and mobile phase B (0.1% FA in acetonitrile). The gradient program employed for the chromatographic separation is described in Table 3. The injection volume employed is 10 μL. The mass spectrometer is operated using ESI (electrospray ionization) positive in MRM (multiple reaction monitoring) mode. Mass transitions are monitored, respectively, for β-lapachone–D6 (Internal Standard, IS)=249>159, β-lapachone=243>159, and β-lapachone–ketal=317>243. Argon is used as the collision gas and Nitrogen is used as the desolvation gas. The collision cell gas pressure is $1.7 \times 10^{-3}$ mbar. The cone gas flow is 108 L/h and the desolvation gas flow is 537 L/h. The source temperature is set to 110° C. and the desolvation temperature is 400° C. The capillary voltage is set to 3.9 kV, the cone voltage is set to 25 V, and the collision energy is 30 V. Data is processed using QuanLynx with MassLynx version 4.0 software.

TABLE 3

| Gradient HPLC parameters | | |
|---|---|---|
| Time (min) | % B | Flow (mL/min) |
| 0 | 40 | 0.3 |
| 0.3 | 40 | 0.3 |
| 2.75 | 95 | 0.3 |
| 3.25 | 95 | 0.3 |
| 3.26 | 40 | 0.6 |
| 3.50 | 40 | 0.6 |
| 3.75 | 40 | 0.3 |

Standard stock solution of β-lapachone is prepared by dissolving 2-3 mg into an equivalent volume of DMSO to yield a 1 mg/mL stock solution. Spiking Solutions at 20,000 ng/mL are prepared by taking 20 μL of the 1 mg/mL stock and combining them with 980 μL of water. Internal standard (IS) stock solution of β-lapachone-D6 is prepared by dissolving 1 mg of β-lapachone-D6 into 2 mL of DMSO. An IS working solution at a concentration of 300 ng/mL is prepared from the 1 mg/mL IS stock by dilution with acetonitrile. Standard solutions for calibration are prepared by dilution of the appropriate Spiking Solution with blank Ncr NU/NU mouse plasma (Bioreclamation, Inc., East Meadow, N.Y.).

Example 14

In Vitro Release of Therapeutic Agents from Polymer Conjugates in Murine Plasma

Standard stock solutions of polymer-modified β-lapachone conjugates are prepared by dissolving 16.6 mg of Sample A, 5.45 mg of Sample B, 5.9 mg of Sample D, and 6.39 mg of Sample J (Table 1), respectively into 1 mL of 40 mM phosphate buffer pH 7.4 for Samples A, B and D, and 1 mL of water for Sample J. Based on loading factors these solutions should yield ~1 mg/mL equivalents of β-lapachone upon hydrolysis. A 20,000 ng/mL (β-lapachone equivalents) Spiking Solution of each is prepared by taking 20 μL aliquots of the respective stock solution and combining it with 980 μL of its respective diluent. A β-lapachone standard is prepared at 2000 ng/ml (a single point calibrant) by making a 1 to 10 dilution of the appropriate 20,000 ng/mL Spiking Solution in blank Ncr NU/NU mouse plasma (Bioreclamation, Inc., East Meadow, N.Y.); for calibration 50 μL of the standard (single point calibrant) is combined with 50 μL of water mixed and 200 μL of the IS working solution is added. This solution is mixed and then centrifuged at 13,000 rpm for 10 minutes. The supernatant is transferred to a HPLC vial for analysis. For plasma stability measurements, 50 μL of 0, 1, 2, and 5 hour of each plasma time point sample (2000 ng/mL polymer-modified β-lapachone conjugate in plasma) is combined with 100 μL of IS working solution, mixed and centrifuged at 13,000 rpm for 10 minutes. Control samples of polymer-modified β-lapachone conjugates are prepared at 2000 ng/mL (β-lapachone equivalents) by making a 1 to 10 dilution of the appropriate 20,000 ng/mL spiking solution in the appropriate diluent (either water or phosphate buffer). Control samples (2000 ng/mL) are combined with 50 uL diluent and then 200 μL of the IS working solution is added. The samples are mixed and then centrifuged at 13,000 rpm for 10 minutes. The supernatant is transferred to a HPLC vial for analysis.

Example 15

Tumor and Plasma Levels of Free and Total β-Lapachone in Ncr NU/NU Mice

Figure 4:
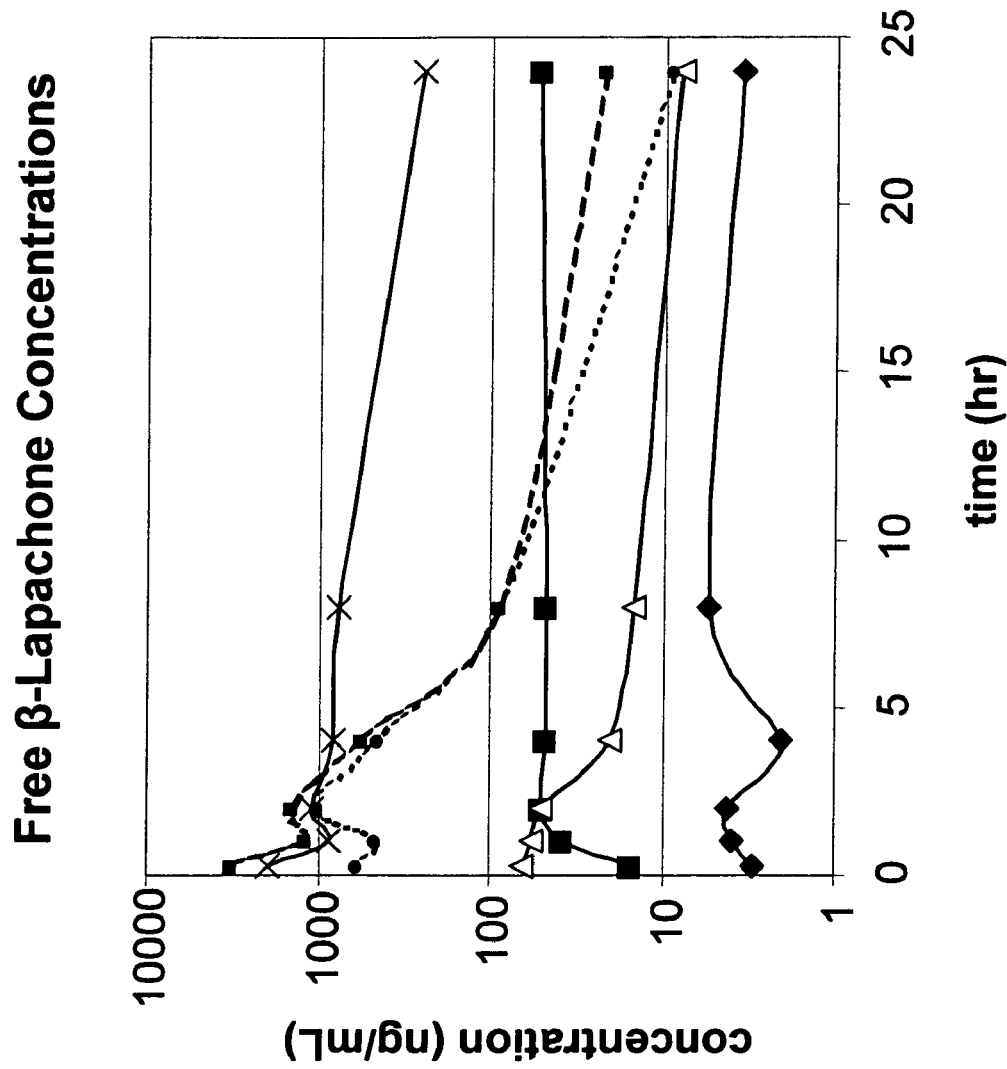
FIG. 4 sets forth a time course of tumor and plasma levels (concentration given in ng/ml) of: β-lapachone following administration of: β-lapachone (reference) by intraperitoneal administration (ip) (60 mg/kg) or (2,2-dimethyl-5-oxo-3,4-dihydro-2H,5H-spiro[benzo[h]chromene-6,2'-[1,3]dioxolan]-4'-yl)methyl γ-poly-L-glutamate sodium (Table 1: Sample J) by intravenous (iv) administration (60 mg/kg equivalents of β-lapachone, 370 mg/kg of the polymer conjugate having 16.2% β-lapachone by weight) to Ncr NU/NU tumor bearing mice. Free β-lapachone tumors (♦) free ketal (i.e. 4'-(hydroxymethyl)-2,2-dimethyl-3,4-dihydro-2H,5H-spiro[benzo[h]chromene-6,2'-[1,3]dioxolan]-5-one) in tumor (■) (β-lapachone equivalents); free β-lapachone in plasma (Δ); free ketal in plasma (X) (β-lapachone equivalents); β-lapachone reference plasma (--■--); and β-lapachone reference tumor (•••●•••). Experimental details are set forth in Example 13 and 15.

Female Ncr NU/NU mice (8 weeks of age) (Charles River Laboratories) were implanted subcutaneously with 5 million HT29 human colon cancer cells by subcutaneous injection in the flank. (HT-29 cells are grown in Dulbecco's Modified Eagle Medium (DMEM) supplemented with 10% fetal bovine serum (FBS) and 1% penicillin/streptomycin (PS) (Roche) in a in a humidified 5% $CO_2$ atmosphere at 37° C.). Seven days following HT29 cell implantation all mice are weighed prior to dosing with polymer-modified β-lapachone conjugates: Sample B, 14.5 mg/ml PEG 400: 50 mM phosphate buffer pH 9.0, 139 mg/kg (26 mg/kg β-lapachone equivalents), FIG. 3; Sample J, 74 mg/ml PEG 400: 50 mM phosphate buffer pH 9.0, 370 mg/kg (60 mg/kg β-lapachone equivalents), FIG. 4; Sample B, 14.5 mg/ml PEG 400: 50 mM phosphate buffer pH 9.0, 72.5 mg/kg (14 mg/kg β-lapachone equivalents) and Sample D, 15.1 mg/ml PEG 400: 50 mM phosphate buffer pH 9.0, 75.3 mg/kg (14 mg/kg β-lapachone equivalents) FIGS. 5A and 5B; by iv bolus administration (dose volume 5 ml/kg) and β-lapachone in 40% hydroxypropyl-β-cyclodextrin (60 mg/kg) by ip administration. Blood and is collected at the following time points post dosing: 0.25, 1, 2, 4, 8, and 24 hours. For blood draws, the dead volume of 1 cc syringe fitted with 27 gauge needle is filled with EDTA solution (1.5% w/v in 0.9% saline); total volume of EDTA solution ~80 μl per syringe. Cardiac puncture is then performed yielding approximately 500 μl of blood from each mouse. Blood samples are immediately placed on ice and centrifuged at 4° C. Plasma samples are flash frozen on dry ice and stored at −80° C. Following blood sampling, tumor samples are harvested and flash frozen on dry ice then stored at −80° C.

A calibration curve is prepared in the range of 1 to 2000 ng/mL (1, 3, 6, 10, 30, 60, 100, 300, 600, 1000, and 2000 ng/mL) by performing serial dilutions of a 2000 ng/mL standard prepared in Ncr NU/NU mouse plasma (Bioreclamation, Inc., East Meadow, N.Y.). 50 μL of each calibration standard is combined with 100 uL of the IS working solution, mixed and centrifuged at 13,000 rpm for 10 minutes. The supernatant is transferred to a HPLC vial for analysis. For tumor pharmacokinetic (PK) studies the calibration standards are prepared in the same fashion as the plasma calibration standard with the exception that blank tumor homogenate (see sample preparation section, below) is used as the diluent.

To determine free β-lapachone plasma levels 50 μL of each plasma sample is combined with 100 μL of IS working solution, mixed, and then centrifuged at 13,000 rpm for 10 minutes. The supernatant is transferred to a HPLC vial for analysis. Where required, plasma samples are diluted either 1 to 10 or 1 to 100 in blank plasma. To determine free β-lapachone in tumor samples, each sample (including blank tumors for calibration curve preparation) is homogenized (1 mg tissue to 10 μL buffer) in 10 mM ammonium acetate buffer pH 7.3 using a 2 mL hand operated dounce homogenizer. The tumor PK samples are then prepared for analysis in the same manner as described for the plasma samples (i.e., 50 μL samples are added to 100 μL IS working solution).

To determine total β-lapachone in plasma and tumor, samples are hydrolyzed by combining 50 μL of the sample with 50 μL of either 1 N HCl (for Sample A) or 0.1 N NaOH (for Samples B, D, and J). After allowing the hydrolysis samples to stand for an appropriate interval of time, 50 μL of each hydrolyzed sample is combined with 100 μL of IS working solution, mixed, and then centrifuged at 13,000 rpm for 10 minutes. The supernatant is transferred to a HPLC vial for analysis.

What is claimed is:

1. A composition comprising B-lapachone attached to a carboxyl-containing polymer, wherein said carboxyl-containing polymer is a polyglutamic acid (PGA) polymer, and wherein said PGA polymer and β-lapachone form a composition comprising one or more residues of the form:

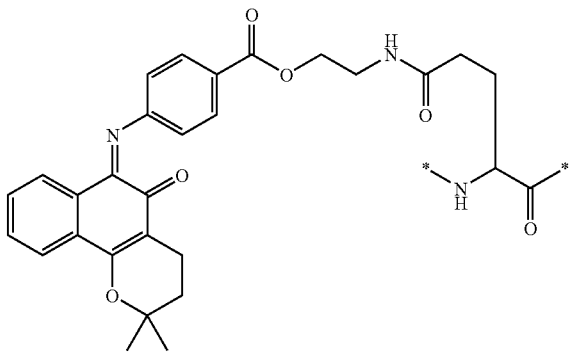

where "*" indicates the points of attachment to other residues of said PGA polymer.

2. A pharmaceutical composition comprising said composition of claim 1, wherein said pharmaceutical composition is a formulation for oral, parenteral, or intravenous administration.

* * * * *

UNITED STATES PATENT AND TRADEMARK OFFICE
CERTIFICATE OF CORRECTION

PATENT NO.        : 7,812,051 B2                                     Page 1 of 1
APPLICATION NO.   : 11/201097
DATED             : October 12, 2010
INVENTOR(S)       : Mark A. Ashwell It is certified that error appears in the above-identified patent and that said Letters Patent is hereby corrected as shown below:

Col. 92, line 49, claim 1, the word "B-lapachone" should be corrected to "β-lapachone"

Signed and Sealed this

Twenty-third Day of November, 2010

David J. Kappos
*Director of the United States Patent and Trademark Office*